US009458198B1

(12) United States Patent
Osterkamp et al.

(10) Patent No.: US 9,458,198 B1
(45) Date of Patent: Oct. 4, 2016

(54) CYCLIC PEPTIDE-BASED NPR-B AGONISTS

(71) Applicant: Shire Orphan Therapies GmbH, Berlin (DE)

(72) Inventors: Frank Osterkamp, Berlin (DE); Heiko Hawlisch, Berlin (DE); Gerd Hummel, Berlin (DE); Tobias Knaute, Berlin (DE); Ulf Reimer, Berlin (DE); Ulrich Reineke, Berlin (DE); Bernadett Simon, Bonn (DE); Uwe Richter, Berlin (DE); Edgar Specker, Berlin (DE); Markus Woischnik, Berlin (DE); Mark R. Hellberg, Arlington, TX (US)

(73) Assignee: Shire Orphan Therapies GmbH, Berlin (DE)

( * ) Notice: Subject to any disclaimer, the term of this patent is extended or adjusted under 35 U.S.C. 154(b) by 245 days.

(21) Appl. No.: 13/916,019

(22) Filed: Jun. 12, 2013

Related U.S. Application Data

(63) Continuation of application No. 12/825,139, filed on Jun. 28, 2010, now abandoned.

(60) Provisional application No. 61/220,697, filed on Jun. 26, 2009.

(51) Int. Cl.
| | |
|---|---|
| *C07K 7/64* | (2006.01) |
| *A61K 38/00* | (2006.01) |
| *A61K 38/12* | (2006.01) |
| *C07K 7/08* | (2006.01) |
| *C07K 7/02* | (2006.01) |

(52) U.S. Cl.
CPC ............... *C07K 7/08* (2013.01); *A61K 38/00* (2013.01); *C07K 7/02* (2013.01); *C07K 7/64* (2013.01)

(58) Field of Classification Search
None
See application file for complete search history.

(56) References Cited

U.S. PATENT DOCUMENTS

| | | | |
|---|---|---|---|
| 6,995,186 | B2 | 2/2006 | Castillo et al. |
| 7,297,709 | B2 | 11/2007 | Dai et al. |
| 2003/0055102 | A1 | 3/2003 | Castillo et al. |
| 2005/0158387 | A1 | 7/2005 | Castillo et al. |
| 2006/0189608 | A1 | 8/2006 | Bingaman |
| 2007/0265206 | A1 | 11/2007 | Sharma et al. ................. 514/15 |
| 2011/0282030 | A1 | 11/2011 | Dickey et al. ................ 530/324 |

OTHER PUBLICATIONS

Langenickel et al; "Cardiac hypertrophy in transgenic rats expressing a dominant-negative mutant of the natriuretic peptid receptor B" PNAS; vol. 103; No. 12; pp. 4735-4740 (Mar. 21, 2006).
Ohbayashi et al; "Compared effects of natriuretic peptides on ovalbumin-induced asthmatic model"; European Journal of Pharmacology; vol. 346; pp. 55-64 (1998).
Obata et al; "CNP infusion attenuates cardiac dysfunction and inflammation in myocarditis"; Biochemical and Biophysical Research Communications; vol. 356; pp. 60-66 (2007).

(Continued)

*Primary Examiner* — Kevin S Orwig
(74) *Attorney, Agent, or Firm* — Proskauer Rose LLP; Fangli Chen

(57) ABSTRACT

Disclosed are cyclic, peptide-based novel compounds having NPR-B agonistic activity. Preferred compounds are cyclic peptides containing conventional or non-conventional L- or D-amino acid residues connected to one another via peptide bonds. In some embodiments, provided herein are a cyclic peptide compound with a ring size that is significantly reduced as compared to known NPR-B agonists, such as CNP.

20 Claims, 3 Drawing Sheets

ANP BNP CNP

(56) References Cited

OTHER PUBLICATIONS

Leske; "Open-angle glaucoma—an epidemiologic overview"; Ophthalmic Epidemiology; Reviews; vol. 14; pp. 166-172 (2007).
Minamino et al; "Characterization of immunoreactive human c-type natriuretic peptide in brain and heart"; Biochemical and Biophysical Research Communications; vol. 179; No. 1; pp. 535-542 (Aug. 30, 1991).
Millar et al; "Atriopeptin lowers aqueous humor formation and intraocular pressure and elevates ciliary cyclic GMP but lacks uveal vascular effects in the bovine perfused eye"; Journal of Ocular Pharmacology and Therapeutics; vol. 13; No. 1; pp. 1-11 (1997).
Makino et al; "Transgenic overxpression of brain natriuretic peptide prevents the progression of diabetic nephropathy in mice"; Diabetologia; vol. 49; pp. 2514-2524 (2006).
Lohe et al; "Natriuretic peptide B receptor and c-type natriuretic peptide in the rat kidney"; J Am. Soc. Nephrol; vol. 6; pp. 1552-1558 (1995).
Itoh et al; "Expression of biologically active receptors for natriuretic peptides in the human uterus during pregnancy"; Biochemical and Biophysical Research Communications; vol. 203; No. 1; pp. 602-607 (Aug. 30, 1994).
Kyriakides et al; "Atrial natriuretic peptide augments coronary collateral blood flow: a study during coronary angioplasty"; Clin. Cardiol. vol. 21; pp. 737-742 (1998).
Horl; Natriuretic peptides in acute and chronic kidney disease and during renal replacement therapy"; Journal of Investigative Medicine"; vol. 53; No. 7; pp. 366-370 (Nov. 2005).
Canaan-Huhl et al; "C-type natriuretic peptide inhibits mesangial cell proliferation and matrix accumulation in vivo"; Kidney International; vol. 53; pp. 1143-1151 (1998).
Mattingly et al; "Presence of c-type natriuretic peptide in human kidney and urine"; Kidney International; vol. 46; pp. 744-747 (1994).
Korenfeld and Becker; Atrial natriuretic peptides; effects on intraocular pressure; cGMP, and aqueous flow; Investigative Ophthalmology & Visual Science; vol. 30; No. 11; pp. 2385-2392 (Nov. 1989).
Komeichi et al; "Blunted natriuresis and abnormal systemic hemodynamic responses to c-type and brain natriuretic peptides in rats with cirrhosis"; Journal of Hepatology; vol. 22; pp. 319-325 (1995).
Hosang and Heinz-Scheit; "cDNA cloning identified a calmodulin-binding protein in bovine seminal plasma and bovine c-type natriuretic peptide"; DNA and Cell Biology; vol. 13; No. 4; pp. 409-417 (1994).
Huang et al; Isolation, mapping, and regulated expression of the gene encoding mouse c-type natriuretic peptide; American Physiological Society; vol. 271; pp. H1565-H1575 (1996).
Marumo et al; "Natriuretic peptide-augmented induction of nitric oxide synthase through cyclic guanosine 3',5'-monophosphate elevation in vascular smooth muscle cells"; Endocrinology; vol. 136; No. 5; pp. 2135-2142 (1995).
Mantyh, et al; "Localization of specific binding sites for atrial natriuretic factor in peripheral tissues of the guinea pig, rat, and human"; Hypertension; vol. 8; pp. 712-721 (1986).
Khurana and Padney; "Receptor-mediated stimulatory effect of atrial natriuretic factor, brain natriuretic peptide, and c-type natriuretic peptide on testosterone production in purified mouse leydig cells: activation of cholesterol side-chain cleavage enzyme"; Endocrinology; vol. 133; No. 5; pp. 2141-2149 (1993).
Noubani et al.; "B-type natriuretic peptide receptor expression and activity are hormonally rgulated in rat ovarian cells"; Endocrinology; vol. 141; No. 2; pp. 551-559 (2000).
Kim et al; "Presence and biological activity of c-type natriuretic peptide-dependent guanylate cyclase-coupled receptor in the penile corpus cavernosum"; The Journal of Urology; vol. 159; pp. 1741-1746 (May 1998).
Hutchinson, et al. "Mechanisms of natriuretic-peptide-induced growth inhibition of vascular smooth muscle cells"; Cardiovascular Research; vol. 35; pp. 158-167 (1997).
Krejci, et al.; "Interaction of fibroblast growth factor and C-natriuretic peptide signaling in regulation of chondrocyte proliferation and extracellular matrix homeostatis"; Journal of Cell Science; vol. 118; pp. 5089-5100 (2005).
Murthy and Makhlouf; "Identification of the G protein-activating domain of the natriuretic peptide clearance receptor (NPR-C)"; The Journal of Biological Chemistry; vol. 274; No. 25; pp. 17587-17592 (Jun. 18, 1999).
Itoh et al.; "C-type natriuretic peptide ameliorates monocrotaline-induced pulmonary hypertension in rats"; Am. J. Respir. Crit. Care Med.; vol. 170; pp. 1204-1211 (2004).
Moffatt et al.; "Osteocrin is a specific ligand ofthe natriuretic peptide clearance receptor that modulates bone growth"; The Journal of Biological Chemistry; vol. 282; No. 5; pp. 36454-36462 (Dec. 14, 2007).
Miyazawa, et al.; "Cyclic GMP-dependent protein kinase II plays a critical role in c-type natriuretic peptide-mediated endochondral ossification"; Endocrinology; vol. 143; No. 9; pp. 3604-3610 (2002).
Grower et al.; "Four peptides decrease human colon adenocarcinoma cell number and DNA synthesis via cyclic GMP"; International Journal of Gastrointestional Cancer; vol. 36; No. 2; pp. 77-88 (2005).
Middendorff; "Natriuretic peptides in the human testis: evidence for a potential role of c-type natriuretic peptide in leydig cells"; Journal of Clinical Endocrinology and Metabolism; vol. 81; No. 12; pp. 4324-4328 (1996).
Ikeda, et al; "Natriuretic peptide family as a novel antimigration factor of vascular smooth muscle cells"; Arterioscler Thromb Vasc. Biol.; vol. 17; pp. 731-736 (1997).
Maack et al.; "Physiological role of silent receptors of atrial natriuretic factor"; Science; vol. 238; pp. 675-678 (Oct. 30, 1987).
Koller, et al.; "Selective activation of the B natriuretic peptide receptor by c-type natriuretic peptide (CNP)"; Science; vol. 252; pp. 120-123 (Apr. 5, 1991).
Marton, et al; "NEP inhibitors enhance c-type natriuretic peptide-induced relaxation in porcine isolated coronary artery"; Vascular Pharmacology; vol. 43; pp. 207-212 (2005).
Morishige, et al; "Local adenovirus-mediated transfer of c-type natriuretic peptide suppresses vascular remodeling in porcine coronary arteries in vivo"; Journal of American College of Cardiology; vol. 35; No. 4; pp. 1040-1047 (2000).
Misono, et al; "Structural studies of the natriuretic peptide receptor: a novel hormone-induced rotation mechanism for transmembrane signal transduction"; Peptides; vol. 26; pp. 957-968 (2005).
Madhani et al; "Vascular natriuretic peptide receptor-linked particulate guanylate cyclases are modulated by nitric oxide-cyclic GMP signalling"; British Journal of Pharmacology; vol. 139; pp. 1289-1296 (2003).
Horio et al; "Gene expression, secretion, and autocrine action of c-type natriuretic peptide in cultured adult rat cardiac fibroblasts"; Endocrinology; vol. 144; No. 6; pp. 2279-2284 (2003).
Gulberg, et al; "Increased renal production of c-type natriuretic peptide (CNP) in patients with cirrhosis and functional renal failure"; Gut.; vol. 47; pp. 852-857 (2000).
Gilkes, et al; "Characterization of natriuretic peptide receptor subtypes in the AtT-20 pituitary tumour cell line"; Biochem. J.; vol. 299; pp. 481-487 (1994).
Fuller et al; "Atrial natriuretic peptide clearance receptor"; The Journal of Biological Chemistry; vol. 263; No. 19; pp. 9395-9401 (Jul. 5, 1988).
Furuya et al. "C-type natriuretic peptide is a growth inhibitor of rat vascular smooth muscle cells"; Biochemical and Biophysical Research Communications; vol. 177; No. 3; pp. 927-931 (Jun. 28, 1991).
Shinomiya, et al; "C-type natriuretic peptide inhibits intimal thickening of rabbit carotid artery after balloon catheter injury"; Biochemical and Biophysical Research Commuonications; vol. 205; No. 2; pp. 1051-1056 (Dec. 15, 1994).

(56) References Cited

OTHER PUBLICATIONS

Gaspari et al; "Type-C natriuretic peptide prevents development of experimental atherosclerosis in rabbits"; Clinical and Experimental Pharmacology and Physiology; vol. 27; pp. 653-655 (2000).
Furuya et al; "C-type natriuretic peptide inhibits intimal thickening after vascular injury"; Ann NY Acad. Sci. vol. 748; pp. 517-523 (1995).
Foresta, et al; "Stimulatory effects of a-hANP on testosterone secretion in man"; Journal of Clinical Endocrinology and Metabolism; vol. 2; No. 2; pp. 392-295 (1991).
Foster et al; "The prevalence of glaucoma in Chinese residents of Singapore"; Epidemiology and Biostatistics; vol. 18; pp. 1105-1111 (Aug. 2000).
Fenrick et al; Cloning and functional expression of the bovine natriuretic peptide receptor-B (Natriuretic factor R1c subtype); Molecular and Cellular Biochemistry; vol. 137; pp. 173-182 (1994).
Fluge, et al; "Bronchodilating effects of natriuretic and vasorelaxant peptides compared to salbutamol in asthmatics"; Regulatory Peptides; vol. 59; pp. 357-370 (1995).
Fernandez-Durango et al; "Type B and type C natriuretic peptide receptors modulate intraocular pressure in the rabbit eye"; European Journal of Pharmacology; vol. 364; pp. 107-113 (1999).
Dos Reis, et al; "Characterization and distribution of natriuretic peptide receptors in the rat uterus"; Endocrinology; vol. 136; No. 10; pp. 4247-4253 (1995).
Beltowski and Wojcicka; "Regulation of renal tubular sodium transport by cardiac natriuretic peptides: two decades of research"; Med. Sci. Monit; vol. 8; No. 2; pp. RA39-RA52 (2002).
Del Ry, et al; "C-type natriuretic peptide plasma levels increase in patients with chronic heart failure as a function of clinical severity"; The European Journal of Heart Failure; vol. 7; pp. 1145-1148 (2005).
Barber et al; "Atrial natriuretic peptide preserves endothelial function during intimal hyperplasia"; Vascular Research; vol. 42; pp. 101-110 (2005).
Ding and Abdel-Latif; "Actions of c-type natriuretic peptide and sodium nitroprusside on carbachol-stimulated inositol phosphate format and contraction in ciliary and iris sphincter smooth muscles"; Investigative Ophthalmology and Visual Science; vol. 38; No. 12; pp. 2629-2638 (1997).
Del Ry, et al; "Increased levels of c-type natriuretic peptide in patients with idiopathic left ventricular dysfunction"; Peptides; vol. 28; pp. 1068-1073 (2007).
Ozasa, et al; "Complementary antagonistic actions between C-type natriuretic peptide and the MAPK pathway through FGFR-3 in ATDC5 cells"; Bone; vol. 36; pp. 1056-1064 (2005).
Bianciotti, et al; "Centrally applied atrial natriuretic factor diminishes bile secretion in the rat"; Regulatory Peptides; vol. 102; pp. 127-133 (2001).
Becker; "Topical 8-bromo-cyclic GMP lowers intraocular pressure in rabbits"; Investigative Ophthalmology & Visual Science; vol. 31; No. 8; pp. 1647-1649 (Aug. 1990).
Bartels et al; "Mutations in the transmembrane natriuretic peptide receptor NPR-B impair skeletal growth and cause acromesomelic dysplasia, type maroteaux"; Am. J. Hum. Genet.; vol. 75; pp. 27-34 (2004).
Anand-Srivastava; "Natriuretic peptide receptor-C signaling and regulation"; Peptides; vol. 26; pp. 1044-1059 (2005).
Abdelalim et al; "Distribution of natriuretic peptide receptor-C immunoreactivity in the rat brainstem and its relationship to cholinergic and catecholaminergic neurons"; Neuroscience; vol. 155; pp. 192-202 (2008).
Mukoyama et al; "Brain natriuretic peptide as a novel cardiac hormone in humans"; J. Clin. Invest.; vol. 87; pp. 1402-1412 (Apr. 1991).
Kuthe et al; "Expression of guanylyl cyclase B in the human corpus cavernosum penis and the possible involvement of it ligand c-type natriuretic polypeptide in the induction of penile erection"; Journal of Urology; vol. 169; Issue 5; pp. 1918-1922 (May 2003).
Murakami et al; "C-type natriuretic peptide attenuates bleomycin-induced pulmonary fibrosis in mice"; Am. J. Physiol Lung Cell Mol. Physiol; vol. 287; pp. L1172-L1177 (2004).
Mattingly et al; "Presence of c-type natriuretic peptide in human kidney and urine"; Kidney International; vol. 46. pp. 744-747 (1994).
Buschhausen et al; "Regulation of mesangial cell function by vasodilatory signaling molecules"; Cardiovascular Research; vol. 51; pp. 463-469 (2001).
Vlachopoulos et al; "Amino-terminal pro-c-type natriuretic peptide is associated with the presence, severity, and duration of vasculogenic erectile dysfunction"; European Association of Urology; vol. 56; pp. 552-558 (2009).
Yoder et al; "Reduced ability of c-type natriuretic peptide (CNP) to activate natriuretic peptide receptor B (NPR-B) causes dwarfism in Ibab −/−mice"; Peptides; vol. 29; pp. 1575-1581 (2008).
Yasoda et al; "Overexpression of CNP in chondrocytes rescues achondroplasia through a MAPK-dependent pathway"; Nature Medicine; vol. 10; No. 1; pp. 80-86 (Jan. 2004).
Yamashita et al; "Opposite regulation of gax homeobox expression by angiotensin II and c-type natriuretic peptide"; Hypertension; Journal of the American Hearth Association; vol. 29; pp. 381-385 (1997).
Wright et al; "Amino-terminal pro-c-type natriuretic peptide in heart failure"; Hypertension; Journal of the American Heart Association; vol. 43; pp. 94-100 (2004).
Woods and Jones; "Atrial, b-type and c-type natriuretic peptides cause mesenteric vasoconstriction in conscious dogs"; Am. J. Physiol.; vol. 276 (regulatoary Integrative Comp. Physiol; pp. R1443-R1452 (1999).
Tsuki et al; "Hypomorphic mutation in mouse Nppc gene causes retarded bone growth due to impaired endochondral ossification"; Biochemical and Biophysical Research Communications; vol. 376; pp. 186-190 (2008).
Suga et al; "Characterization of natriuretic peptide receptors in cultured cells"; Hypertension; vol. 19; pp. 762-765 (1992).
Suga et al; "Phenotype-related alteration in expression of natriuretic peptide receptors in aortic smooth muscle cells"; Circulation Research; vol. 71; pp. 34-39 (1992).
Shahidullah and Wilson; "Atriopeptin, sodium azide and cyclic GMP reduce secretion of aqueous humour and inhibit intracellular calcium release in bovine cultured ciliary epithelium"; British Journal of Pharmacology; vol. 127; pp. 1438-1446 (1999).
Quigley; "European glaucoma prevention study"; Ophthalmology; vol. 112; No. 9; pp. 1642-1643 (Sep. 2005).
Qian et al; "Local expression of c-type natriuretic peptide suppresses inflammation, eliminates shear stress-induced thrombosis, and prevents neointima formation through enhanced nitric oxide production in rabbit injured carotid arteries"; Circulation Research; vol. 91; pp. 1063-1069 (2002).
Pfeifer et al; "Intestinal secretory defects and dwarfism in mice lacking cGMP-dependent protein kinase II"; Science; vol. 274; pp. 2082-2086 (Dec. 20, 1996).
Olney; "C-type natriuretic peptide in growth: A new paradigm"; Growth Hormone & IGF Research; vol. 16; pp. S6-S14 (2006).
Ohno et al; "Accelerated reendothelialization with suppressed thrombogenic property and neointimal hyperplasia of rabbit jugular vein grafts by adenovirus-mediated gene transfer of c-type natriuretic peptide"; Circulation; vol. 105; pp. 1623-1626 (2002).
Nakamura et al; "vasodilatory effects of c-type natriuretic peptide on forearm resistance vessels are distinct form those of artial natriuretic peptide in chronic heart failure"; Circulation; vol. 90; pp. 1210-1214 (1994).
Ahluwalia et al; "Vascular actions of natriuretic peptides" Basic Res. Cardiol; vol. 99; pp. 83-89 (2004).
Ardaillou et al; "Mesangial cells from diabetic NOD mice constitutively express increased density of atrial natriuretic peptice C receptors"; Kidney International; vol. 55; pp. 1293-1302 (1999).
Beaulieu et al; "Positive chronotropic and inotropic effects of c-type natriuretic peptide in dogs"; Am. J. Physiol; vol. 73; pp. H1933-H1940 (1997).

(56) References Cited

OTHER PUBLICATIONS

Brenard et al; "Hemodynamic and sympathetic responses to human atrial natriuretic peptide infusion in patients with cirrhosis"; Journal of Hepatology; vol. 14; pp. 347-356 (1992).
Cataliotti et al; "CNP production in the kidney and effects of protein intake restriction in nephrotic syndrome"; Am. J. Physiol. Renal Physiol.; vol. 283; pp. F464-F472 (2002).
Chang et al; "Differential activation by atrial and brain natriuretic peptides of two different receptor guanylate cyclases"; Letters to Nature; Nature; vol. 341; pp. 68-72 (Sep. 7, 1989).
Chen and Burnett; "C-type natriuretic peptide: The endothelial component of the natriuretic peptide system"; Journal of Cardiovascular Pharmacology; vol. 32 (Suppl. 3); pp. S23-S28 (1998).
Chinkers et al; "A membrane form of guanylate cyclase is an atrial natriuretic peptide receptor"; Letters to Nature; Nature: vol. 338; pp. 78-83 (Mar. 2, 1989).
Cho et al; "Natriuretic peptides and their therapeutic potential"; Natriuretic Peptides, Heart Disease; vol. 5; pp. 305-328 (1999).
Chrisman et al; "Seminal plasma factors that cause large elevations in cellular cyclic GMP are c-type natriuretic peptides"; The Journal of Biological Chemistry; vol. 268; No. 5; pp. 3698-3703 (Feb. 15, 1993).
Chrisman and Garbers; "Reciprocal antagonism coordinates c-type natriuretic peptide and mitogen-signaling pathways in fibroblasts"; The Journal of Biological Chemistry; vol. 274; No. 7; pp. 4293-4299 (Feb. 12, 2999).
Chusho et al; "Dwarfism and early death in mice lacking c-type natriuretic peptide"; PNAS; vol. 98; No. 7; pp. 4016-4021 (Mar. 27, 2001).
Collin et al; "Atrial natriuretic peptide, brain natriuretic peptide and c-type natriuretic peptide: effects on testicular microcirculation and immunohistochemical localization"; International Journal of Andrology; vol. 20; pp. 55-60 (1997).
Debold et al; "A rapid and potent natriuretic response to intravenous injection of atrial myocardial extract in rats"; Life Sciences; vol. 28; pp. 89-94 (1981).
Dean et al; "Synthesis and localization of c-type natriuretic peptide in mammalian kidney"; Am. J. Phuysiol; 266; F491-F496 (1994).
Yang et al; "An experimental study on effect of atrial natriuretic peptide on intraocular pressure of white rabbits"; Chinese Journal of Ophthalmology; vol. 33; pp. 149-151 (1997) [Abstract in English].
Dickey et al; "Diferential regulation of membrane guanylyl cyclases in congestive heart failure: Natriuretic peptide re ceptor (NPR)-B, not NPR-A, is the predominant natriuretic peptide receptor in the failing heart"; Endocrinology; vol. 148; No. 7; pp. 3518-3522 (2007).
Diestelhorst and Krieglstein; "The intraocular pressure response of human atrial natriuretic factor in glaucoma"; International Ophthalmology; vol. 13; pp. 99-101 (1989).
Drewett et al; "Natriuretic peptide receptor-B (guanylyl cyclase-B) mediates c-type natriuretic peptide relaxation of precontracted rat aorta"; The Journal of Biology Chemistry; vol. 270; No. 9; pp. 4668-4674 (Mar. 3, 1995).
Eguchi et al; "Effects of three distinct natriuretic peptides on receptor binding and guanylate cyclase activities in rat glioma cells"; European Journal of Pharmacology—Molecular Pharmacology Section; vol. 225; pp. 79-82 (1992).
Endlich et al; "Natriuretic peptide receptors mediate different responses in rat renal microvessels"; Kidney International; vol. 52; pp. 202-207 (1997).
Takashima et al; "Ocular hypotensive mechanism of intravitreally injected brain natariuretic peptide in rabbit"; Investigative Ophthalmology & Visual Science; vol. 37; No. 13; pp. 2671-2677 (1996).
Nathanson; "Atriopeptin-activated guanylate cyclase in the anterior segment"; Invest. Ophthalmol. Vis Sci; vol. 28 pp. 1357-1364; (1987).
Nathanson; "Nitrovasodilators as a new class of ocular hypotensive agents"; The Journal of Pharmacology and Experimental Therapeutics; vol. 260; No. 3; pp. 956-965 (1992).

Nathanson; "Direct application of a guanylate cyclase activator lowers intraocular pressure"; Eukropean Journal of Pharmacology; vol. 147; pp. 155-156 (1988).
Osawa et al; "C-type natriuretic peptide inhibits proliferation and monocyte chemoattractant protein-1 secretion in cultured human mesangial cells"; Nephron; vol. 86; pp. 467-472 (2000).
Pandey; "Biology of natriuretic peptides and their receptors"; Peptides; vol. 26; pp. 901-932 (2005).
Pang et al; "Presence of functional type B natriuretic peptide receptor in human ocular cells"; Investigative Ophthalmology and Visual Science; vol. 37; No. 9; pp. 1724-1731 (1996).
Pelisek et al; "C-type natriuretic peptide for reduction of restenosis: gene transfer is superior over single peptide administration"; The Journal of Gene Medicine; vol. 8; pp. 835-944 (2006).
Potter and Garbers; "Dephosphorylation of the guanylyl cyclase-A receptor causes desensitization"; The Journal of Biological Chemistry; vol. 267; No. 21; pp. 14531-14534 (Jul. 25, 1992).
Puurunen and Ruskoaho; "Vagal-dependent stimulation of gastric acid secretion by intracerebroventricularly administered atrial natriuretic peptide in anaesthetized rats"; European Journal of Pharmacology; vol. 141; pp. 493-495 (1987).
Quigley and Proman; "The number of people with glaucoma worldwide in 2010"; Br. J. Ophthalmol; vol. 90; pp. 262-267 (2006).
Resnik et al; "Evaluation of b-type natriuretic peptide (BNP) levels in normal and preeclamptic women"; American Journal of Obstertrics & Gynecology; vol. 193; pp. 450-454 (2005).
Rosenkranz et al; Antihypertrophic actions of the natriuretic peptides in adult rat cardiomyocytes: importance of cyclic GMP; Cardiovascular Research; vol. 57; pp. 515-522 (2003).
Sabbatini et al; "C-type natriuretic peptide applied to the brain enhances exocrine pancreatic secretion through a vagal pathway"; European Journal of Pharmacology; vol. 524; pp. 67-74 (2005).
Sabbatini et al; "C-type natriuretic peptide stimulates pancreatic exocrine secretion in the rat: role of vagal afferent and efferent pathways"; European Journal of Pharmacology; vol. 577; pp. 192-202 (2007).
Schulz; "C-type natriuretic peptide and guanylyl cyclase B receptor"; Peptides; vol. 26; pp. 1024-1034 (2005).
Scotland et al; "C-type natriuretic peptide inhibits leukocyte recruitment and platelet-leukocyte interactions via suppression of P-selectin expression"; PNAS; vol. 102; No. 40; pp. 14452-14457 (Oct. 4, 2005).
Shin et al; "Increased c-type natriuretic peptice mRNA expression in the kidney of diabetic rats"; Journal of Endocrinology; vol. 158; pp. 35-42 (1998).
Soeki et al; "C-type natriuretic peptide, a novel antifibrotic and antihypertrophic agent, prevents cardiac remodeling after myocardial infarction"; Journal of the American College of Cardiology; vol. 45; No. 4; pp. 608-616 (2005).
Stein and Clack; "Topical application of a cyclic GMP analog lowers IOP in normal and ocular hypertensive rabbits"; Investigative Ophthalmology & Visual Science; vol. 35; No. 6; pp. 2765-2768 (1994).
Stepan et al; "Gestational regulation of the gene expression of c-type natriuretic peptide in mouse reproductive and embryonic tissue"; Regulatory Peptides; vol. 102; pp. 9-13 (2001).
Stepan et al; "Expression of c-type natriuretic peptide in human placenta and myometrium in normal pregnancies complicateed by intrauterine growth retardation"; Ftal Diagnosis Therapy; vol. 17; pp. 37-41 (2002).
Stingo et al; "Presence of c-type natriuretic peptide in cultured human endothelial cells and plasma"; Am. J. Physiol; vol. 263; pp. H1318-H-1321 (1992).
Stoupakis and Klapholz; "Natriuretic peptides: biochemistry, physiology, and therapeutic role in heart failure"; Heart Disease; vol. 5; No. 3; pp. 215-223 (2003).
Stumpff and Wiederholt; "Regulation of trabecular meshwork contractility"; Ophthalmologica; vol. 214; pp. 33-53 (2000).
Suda et al; "Skeletal overgrowth in transgenic mice that overexpress brain natriuretic peptide"; Proc. Natl. Acad. Sci.; vol. 95; pp. 2337-2342 (Mar. 1998) Cell Biology.
Sudoh et al; "A new natriuretic peptide in porcine brain"; Letters to Nature; Nature; vol. 332; pp. 78-81 (Mar. 3, 1988).

(56) References Cited

OTHER PUBLICATIONS

Sudoh et al; "C-type natriuretic peptide (CNP): A new member of natriuretic peptide family identified in porcine brain"; Biochemical and Biophysical Research Communications; vol. 168; No. 2; pp. 863-870 (Apr. 30, 1990).
Suganami et al; "Overexpression of brain natriuretic peptide in mice ameliorates immune-mediated renal injury"; J. Am. Soc. Nephrol; vol. 12; pp. 2652-2663 (2001).
Sugrue and Viader; "Synthetic atrial natriuretic rfactor lowers rabbit intraocular pressure"; european Journal of Pharmacology; vol. 130; pp. 349-350 (1986).
Takashima et al; "Ocular hypotension induced by intravitreally injected c-type natriuretic peptide"; Exp. Eye Research; vol. 66; pp. 89-96 (1998).
Tamura et al; "Cardiac fibrosis in mice lacking brain natriuretic peptide"; PNAS; vol. 97; No. 8; pp. 4239-4244 (Apr. 11, 2000).
Tamura et al; "Critical roles of the guanylyl cyclase B receptor in endochondral ossification and development of female reproductive organs"; PNAS; vol. 101; No. 49; pp. 17300-17305 (Dec. 7, 2004).
Tao, et al. "Biological effects of c-type natriuretic peptide in human myofibroblastic hepatic stellate cells"; Journal of Biological Chemistry; vol. 274; No. 34; pp. 23761-23769 (Aug. 20, 1999).
Mittag et al; "Atrial natriuretic peptide (ANP), guanylate cyclase, and intraocular pressure in the rabbit eye"; Current Eye Research; vol. 6; No. 10; pp. 1189-1196 (1987).
Terada et al; "PCR localization of c-type natriuretic peptide and b-type receptor mRNAs in rat nephron segments"; Am. J. Physiol; vol. 267; pp. F215-F222 (1994).
Thomas et al; "Osteocrin, a novel bone-specific secreted protein that modulates the osteoblast phenotype"; The Journal of Biological Chemistry; vol. 278; No. 50; pp. 50563-50571 (Dec. 12, 2003).
Thylefors and Negrel; The global impact of glaucoma; Clin. Chem.; vol. 38; No. 10; pp. 2136-2139 (1992).
Togashi et al; "Concentrations and molecular forms of c-type natriuretic peptide in brain and cerebrospinal fluid"; Clin. Chem.; vol. 38; No. 10; pp. 2136-2139 (1992).
Tokudome et al; "Inhibitory effect of c-type natriuretic peptide (CNP) on cultured cardiac myocyte hypertrophy: interference between CNP and endothelin-1 signaling pathways"; Endocrinology; vol. 145; pp. 2131-2140 (2004).
Totsune et al; "C-type natriuretic peptide in the human central nervous system: distribution and molecular form"; Peptides; vol. 15; No. 1; pp. 37-40 (1994).
Tsukahara et al; "Effect of alpha-human atrial natriuretic peptides on intraocular pressure in normal albino rabbits"; Ophthalmologica; vol. 197; pp. 104-109 (1988).
Ueno et al; "Local expression of c-type natriuretic peptide markedly suppresses neointimal formation in rat injured arteries through an autocrine/paracrine loop"; Circulation; vol. 96; pp. 2272-2279 (1997).
Van Den Akker; "Structural insights into the ligand binding domains of membrane bound guanylyl cyclases and natriuretic peptide receptors"; J. Mol. Biol.; vol. 311; pp. 923-937 (2001).
Royen et al; "Stimulation of arteriogenesis; a new concept for the treatment of arterial occlusive disease"; Cardiovascular Research; vol. 49; pp. 543-553 (2001).
Vesely et al; "Novel therapeutic approach for cancer using four cardiovascular hormones"; European Journal of Clinical Investigation; vol. 34; pp. 674-682 (2004).
Vesely et al; "Five cardiac hormones decrease the number of human small-cell lung cancer cells"; European Journal of Clinical Investigation; vol. 35; pp. 388-398 (2005).
Vesely et al; "Urodilatin and four cardiac hormones decrease human renal carcinoma cell numbers"; European Journal of Clinical Investigation; vol. 36; pp. 810-819 (2006).
Vollmar et al; "Differential gene expression of the three natriuretic peptides and natriuretic peptide receptor subtypes in human liver"; Gut; vol. 40; pp. 145-150; (1997).
Waldman et al; "Differential effects of natriuretic peptide stimulation on tissue-engineered cartilage"; Tissue Engineering; vol. 14; No. 3; pp. 441-449 (2008).
Walther et al; "Opposite regulation of brain and c-type natriuretic peptides in the streptozotocin-diabetic cardiopathy"; Journal of Molecular Endocrinology; vol. 24; pp. 391-395 (2000).
Wang et al; "Cardiomyocyte-restricted over-expression of c-type natriuretic peptide prevents cardiac hypertrophy induced by myocardial infarction in mice"; European Journal of Heart Failure; vol. 9; pp. 548-557 (2007).
Wei et al; "Action of c-type natriuretic peptide in isolated canine arteries and veins"; Am. J. Physiol.; vol. 264; pp. H71-H73 (1993).
Yan et al; Corin, a transmembrane cardiac serine protease, acts as a pro-atrial natriuretic peptide-converting enzyme; PNAS; vol. 97; No. 15; pp. 8525-8529 (Jul. 18, 2000).
Yasoda et al; "Natriuretic peptide regulation of endochondral ossification"; The Journal of Biological Chemistry; vol. 273; No. 19; pp. 11695-11700 (May 8, 1998).
Zhao et al; "Characterization of c-type natriuretic peptide receptors in human mesangial cells"; Kidney International; vol. 46; pp. 717-725 (1994).
Friedman, Scott, Seminars in medicine of the Beth Israel Hospital, Boston: The cellular basis of hepatic fibrosis—mechanisms and treatment strategies, The New England Journal of Medicine; vol. 328; No. 24 1828-835 [Ovid: Seminars in medicine of the Beth Israel Hospital, Boston; https://ovidsp.tx.ovid.com/sp-3.2.4b/ovidweb.cgi; p. 1-24], Jun. 24, 1993.
Kuhn, Michaela, Structure, regulation, and function of mammalian membrane guanylyl cyclase receptors, with a focus on guanylyl cyclase-a, Review; Circulation Research; DOI: 10.1161/01.RES.0000094745.28948.4D: 700-709, Oct. 17, 2003.

CYCLIC PEPTIDE-BASED NPR-B AGONISTS

This application is a continuation of U.S. application Ser. No. 12/825,139 filed Jun. 28, 2010, which claims priority under 35 U.S.C. §119 to U.S. Provisional Patent Application No. 61/220,697 filed Jun. 26, 2009, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 18, 2016, is named 2006685-0607_SL and is 48,052 bytes in size.

FIELD OF THE INVENTION

The present invention generally relates to compounds which are useful in the treatment and prevention of disorders mediated by natriuretic peptides or proteins. More particularly, the present invention relates to methods of treating or preventing glaucoma, ocular hypertension, and optic neuropathies with pharmaceutical compositions comprising one or more novel peptides described herein.

BACKGROUND OF THE INVENTION

Description of Related Art

The natriuretic peptides (NP's) are a family of cyclic peptide hormones that have first been described by their involvement in the regulation of natriuresis, diuresis and blood pressure control. To date, four natriuretic peptides have been discovered in man, i.e. atrial natriuretic peptide (ANP), B-type or brain natriuretic peptide (BNP), C-type natriuretic peptide (CNP) and urodilatin (see FIG. 1; and Cho et al., 1999, *Heart Dis.* 1:305-328). All NP's are synthesized as prepro-hormones which are activated by proteolytic cleavage before their release into the circulation. The NP's bind to natriuretic peptide receptors (NPR), a group of 3 different membrane bound receptors with guanylyl cyclase activity (Pandey 2005, *Peptides* 26:901-932).

ANP was first discovered as a blood pressure decreasing factor in rat atrial homogenates in 1981 (de Bold 1981, *Life Sci* 28:89-94). Human pre-pro-ANP contains 151 amino acids and is stored after N-terminal cleavage as 126 amino acid pro-ANP, predominantly in atrial granules. Cardiac stretch, due to systemic volume overload induces the rapid release of ANP from these stores. Upon secretion into the circulation, the C-terminal part of pro-ANP is cleaved by the atrial peptidase corin to the biologically active 28 amino acid form of ANP (Yan 2000, *Proc Natl Acad Sci* 97:8525-8529). The remaining N-terminal part can be further cleaved into 3 different hormones. i.e. Long Acting Natriuretic Peptide (LANP, amino acids 1-30), Vessel Dilator (VSDL, amino acids 31-67) and Kaliuretic Peptide (KP, amino acids 79-98) (Vesely 2004, *Eur J Clin Invest* 34:674-682).

After BNP was discovered in porcine brain as a factor that showed smooth muscle relaxing activity (Sudoh T, 1988, *Nature* 332:78), a much greater tissue expression was found in preparations of cardiac ventricles (Mukoyama 1991, *J Clin Invest* 87:1402-1412), which led to the conclusion that BNP is, similarly to ANP, a cardiac peptide hormone. Although BNP can be found in storage granules in the atria, the expression in ventricles is transcriptionally regulated (Tamura 2000, *Proc Natl Acad Sci* 93:4239-4244). Synthesis of prepro-BNP is induced through cardiac wall stretch and leads to a 134 amino acid long peptide which is further cleaved by an unknown protease to yield the 108 amino acid long pro-BNP. Additional cleavage liberates the active 32 amino acid C-terminal fragment of BNP and the inactive 76 amino acid N-terminal fragment also referred to as NT-pro-BNP. To date, no known splice variants of human BNP exists.

CNP was first isolated from porcine brain almost 10 years after the discovery of ANP (Sudoh 1990, *Biochem Biophys Res Comm* 168:863-870). It is primarily expressed in the central nervous system and endothelial cells. Unlike other NP's, CNP is nearly not present in cardiac tissue, which suggest a more paracrine function on vascular tone and muscle cell growth. The 126 amino acid precursor molecule pro-CNP is processed by the intracellular endoprotease furin into the mature 53 amino acid peptide CNP-53, which is the most abundant form in the brain (Totsune 1994, *Peptides* 15:37-40), endothelial cells (Stingo, 1992, *Am J Phys* 263: H1318-H1321) and the heart (Minamino 1991, *Biochem Biophys Res Comm* 179:535-542). In both, cerebral spinal fluid (Togashi 1992, *Clin Chem* 38:2136-2139) and human plasma (Stingo 1992, *Am J Phys* 263:H1318-H1321) the most common form is CNP-22, which is generated from CNP-53 by an unknown extracellular protease. Unlike the other NP's CNP-22 lacks the C-terminal extension of the 17 amino acid ring (see FIG. 1).

ANP, BNP and CNP show a highly conserved amino acid sequence among different vertebrate species (see FIG. 1; and Cho 1999, *Heart Dis.* 1:305-328). The NP's are inactivated by two distinct mechanisms, i.e. enzymatic cleavage through neutral endopeptidases and binding to the NP clearance receptor (NPR-C), which is followed by internalization and intracellular degradation of the NP (Stoupakis 2003, *Heart Dis.* 5:215-223).

The discovery of the natriuretic peptides ANP, BNP and CNP was followed by the description and cloning of their specific receptors, natriuretic peptide receptor-A, -B and -C (NPR-A, -B, -C) (Fuller 1988, *J Biol Chem.* 263:9395-9401; Chang 1989 *Nature* 341:68-72; Chinkers 1989, *Nature* 338: 78-83). NPR-A preferentially binds ANP and BNP, while NPR-B is most specific for CNP and NPR-C binds all natriuretic peptides (Koller 1991, *Science* 252:120-123).

The primary structure of NPR-A and -B contain an extracellular ligand binding domain, transmembrane domain, intracellular kinase homology domain containing phosphorylation sites and a C-terminal guanylate cyclase domain (reviewed in Misono 2005, *Peptides* 26:957-68). The latter classifies NPR-A and -B as particulate guanylate cyclases, also known as GC-A and GC-B (E.C.4.6.1.2). In contrast, NPR—C is lacking intracellular homology domains, but evidence is increasing for NPR-C's role not only as a scavenger receptor for natriuretic peptides, but for its' functional coupling to inhibitory G-proteins and phosphoinositide turnover (Maack 1987, *Science* 238:675-678; Murthy and Makhlouf 1999, *J Biol Chem* 274:17587-17592; Anand-Srivastava 2005, *Peptides* 26:1044-1059). Reflecting the grade of sequence homology in natriuretic peptides, natriuretic peptide receptors show a high degree of homology in their extracellular ligand binding domains, with the calculated similarities being 41% between NPR-A and NPR—B and 29% between NPR-A and NPR-C (van den Akker 2001, *J Mol Biol.* 311:923-937).

Ligand binding to NPRs requires a dimer of glycosylated receptor subunits (Fenrick et al. 1994, *Mol Cell Biochem.* 137:173-182; Kuhn 2003, *Circ Res.* 93:700-709) and is followed by a conformational change leading to activation of the guanylate cyclase domains. Subsequently, activity of particulate guanylate cyclases is regulated through phosphorylation (reviewed in Kuhn 2003, *Circ Res.* 93:700-709). Phosphorylation of NPRs is maximal in the basal state, while ligand binding is followed by dephosphorylation and subsequent desensitization of the receptor.

Natriuretic receptors are expressed in many tissues throughout the organism. NPR-A, -B and -C are present in the cardiovascular system and the kidney, with NPR-C being the most abundant receptor subtype accounting for 80% of NPR-expression in some tissues. NPR-B is present in a particularly high level in rat pineal gland, testis and ovaries. NPR-A and -B ligands both induce endothelium-independent vasorelaxation, where ANP and BNP mainly act on arterial vasculature. In contrast, CNP mainly targets the venous system, with the exception of coronary arteries, that relax in response to CNP stimulation (Marton et al. 2005, *Vascul Pharmacol* 43:207-212). Importantly, induction of hypotension via NPR-B activation requires 10-fold higher concentrations of ligand compared to blood pressure reduction in response to NPR-A activation (Wei et al. 1993, *Am J Physiol.* 264:H71-H73; Woods and Jones 1999, *Am J Physiol.* 276:R1443-R1452). Relaxation of smooth muscle by activation of NPR-B has been shown in a variety of tissues, including blood vessels, seminiferous tubules and uterus. Also contraction of the ocular trabecular meshwork tissue is reduced by activation of natriuretic peptide receptors, confirming functional similarities of trabecular meshwork and smooth muscle cells (Stumpff and Wiederholt 2000, *Ophthalmologica* 214:33-53).

Another main target organ of natriuretic peptides is the kidney. Ligands of NPR-A induce natriuresis and diuresis by a dual mechanism (reviewed in Beltowski and Wojcicka 2002, *Med Sci Monit.* 8:RA39-RA52): (1) increased excretion of sodium by a reduced re-uptake of sodium ions in the distal tubulus, subsequently leading also to higher retention of water in the final urine; and (2) dilation of the affluent and concomitant contraction of the effluent glomerular capillary, increasing glomerular filtration rate, at the cost of reduction of renal perfusion (Endlich and Steinhausen 1997, *Kidney Int.* 52:202-207). In contrast to NPR-A-specific ligands, NPR-B-specific ligands do not induce significant natri- and diuresis, and in addition, show a peculiarity regarding glomerular flow regulation: CNP was shown to dilate both affluent and effluent capillaries in the glomerulus, thus increasing renal blood flow, but not glomerular filtration (Endlich and Steinhausen 1997, *Kidney Int.* 52:202-207).

In addition to effects of NP-receptor (NPR) activation on blood pressure and kidney function, powerful effects of natriuretic peptides on proliferative processes in a variety of cell types have been documented in the literature. Antiproliferative properties of NPR activation are documented for vascular smooth muscle cells, fibroblasts of different origins, mesangial cells, cancer cells and chondrocytes (reviewed in Schulz 2005, *Peptides* 26:1024-1034). At least for VSMC, evidence for the involvement of the transcription factor GAX in the regulation of proliferation has given an indication as to which intracellular mechanisms might be involved in growth regulation through NPR (Yamashita et al. 1997, *Hypertension* 29:381-387). Though tissue growth is mainly regulated by proliferative activity, some organs feature variations in cell size to influence tissue mass. This might be a physiological process, as during endochondral ossification, when chondrocytes mature by undergoing hypertrophy, or a pathological event, as in cardiac hypertrophy, which often precedes chronic heart failure. Both of the above-mentioned events of hypertrophy are regulated by NPR-B. NPR-B deficiency causes dwarfism due to abnormal endochondral ossification, characterized by size reduction of the hypertrophic zone of the epiphyseal growth plate (Bartels et al. 2004, *Am J Hum Genet.* 75:27-34; Tamura et al. 2004, *Proc Natl Acad Sci.* 101:17300-17305).

Quite different, a partial knock out of NPR-B in rats promoted cardiac hypertrophy, i.e. hypertrophy of cardiomyocytes (Langenickel et al. 2006, *Proc Natl Acad Sci.* 103:4735-4740).

Natriuretic peptides, having activity at the natriuretic receptors, were later discovered in various tissues, as well. For example, atrial natriuretic peptide (ANP) was discovered in the early 1980s as an endogenous diuretic and vasorelaxant peptide, whose principle circulating form consists of 28 amino acids (SEQ ID NO:1). Subsequently, other natriuretic peptides, such as brain natriuretic peptide (BNP; SEQ ID NO:2) and C-type natriuretic peptide (CNP; SEQ ID NO:3), were discovered. The presence of natriuretic peptides and their receptors in ocular tissues, especially those involved in the regulation of IOP, have been demonstrated. For example, in rat and rabbit eyes, ANP, BNP, and CNP, as well as NPR-A, -B, and -C mRNA were found in the ciliary processes, retina, and choroid (Mittag et al. 1987, *Curr Eye Res.* 6:1189-1196; Nathanson 1987, *Invest Ophthalmol Vis Sci.* 28:1357-1364; Fernandez-Durango et al. 1995, *Exp Eye Res.* 61:723-729). Similar results were found in bovine ciliary processes and cultured bovine ciliary epithelial cells. (Millar et al. 1997, *J Ocul Pharmacol Ther.* 13:1-11; Shahidullah and Wilson 1999, *Br J Pharmacol.* 127:1438-1446). The presence of the peptides and their receptors in the ciliary epithelium suggests that they may play a role in the production of aqueous humor.

In addition to the ciliary processes, natriuretic peptide receptors were also found in tissues associated with the outflow of aqueous humor. ANP binding sites were localized in the longitudinal ciliary muscle of the guinea pig. (Mantyh et al. 1986, *Hypertension.* 8:712-721). In cultured human TM and ciliary muscle cells, CNP is the most potent and efficacious in stimulating the production of cyclic GMP, indicating the presence of functional NPR-B. Activation of this receptor reduces carbachol-induced calcium influx. (Pang et al. 1996, *Invest Ophthalmol Vis Sci.* 37:1724-1731). This result predicts that activation of NPR-B should cause relaxation of these tissues. Indeed, CNP significantly decreases the carbachol-induced contraction of monkey and human ciliary muscles. (Ding and Abdel-Latif, 1997, *Invest Ophthalmol Vis Sci.* 38:2629-2638). Change in contractility in TM and ciliary muscle may affect the outflow facility of aqueous humor.

Cyclic GMP and compounds that increase cyclic GMP in ocular tissues, such as nitric oxide donors, have been shown to lower IOP. (Nathanson 1988, *Eur J Pharmacol.* 147:155-156; Becker 1990, *Invest Ophthalmol Vis Sci.* 31:1647-1649; Nathanson 1992, *J Pharmacol Exp Ther.* 260:956-965; Stein and Clack 1994, *Invest Ophthalmol Vis Sci.* 35:2765-2768). Since natriuretic peptides potently increase cyclic GMP production, they were predicted to lower IOP, too. In the past 20 years, the natriuretic peptides have been shown to be highly effective as IOP-lowering agents. For example, various researchers have independently shown that intravitreal injection of ANP in rabbits consistently and significantly lowers IOP. This effect lasts for many hours. (Sugrue and Viader, 1986, *Eur J Pharmacol.* 130:349-350; Mittag et al. 1987, *Curr Eye Res.* 6:1189-1196; Nathanson 1987 *Invest Ophthalmol Vis Sci.* 28:1357-1364; Korenfeld and Becker 1989, *Invest Ophthalmol Vis Sci.* 30:2385-2392; Takashima et al. 1996, *Invest Ophthalmol Vis Sci.* 37:2671-2677). The IOP effect of ANP correlates with an increase in cyclic GMP production in the iris-ciliary body. (Korenfeld and Becker 1989, *Invest Ophthalmol Vis Sci.* 30:2385-2392). Intravitreal injection of BNP (Takashima et al. 1996, *Invest Ophthalmol Vis Sci.* 37:2671-2677) or CNP (Takashima et al. 1998, *Exp Eye Res.* 66:89-96) is also highly efficacious in lowering IOP. In addition to intravitreal injection, subconjunctival (Yang et al. 1997, *Chin J Ophthalmol.* 33:149-151) or intracameral (Sugrue and Viader 1986, *Eur J Pharmacol.* 130:349-350; Fernandez-Durango et al. 1999, *Eur J Pharmacol.* 364:107-113) injection of the natriuretic peptides have been shown to be ocular hypotensive as well. Systemic administration of ANP in the rabbit, (Tsukahara et al. 1988, *Ophthalmologica.* 197:104-109) or human (Diestelhorst and Krieglstein 1989, *Int Ophthalmol.* 13:99-101) also lowers IOP. Unfortunately, it has not been possible to deliver these peptides topically due to their inability to penetrate the cornea. Therefore, these potent and efficacious TOP-lowering compounds have not been developed for such use.

There is a need for novel NPR-B agonists having improved bioavailability, as compared to isolated or synthesized natriuretic peptides, that can be used in the treatment of natriuretic peptide-mediated disorders, such as ocular disorders, diabetes-related disorders, vascular disorders, cardiac and cardiovascular pathologies, inflammation and other disorders described herein. The novel NPR-B agonists, compositions and methods of the present invention meet these needs.

SUMMARY OF THE INVENTION

The present invention provides novel NPR-B agonists, also referred to herein as natriuretic peptide mimics or similars, that are therapeutically useful for lowering intraocular pressure (TOP) and treating other disorders where activation of the type B natriuretic peptide receptor will be beneficial. Specifically, the invention provides novel NPR-B agonists that activate the type B natriuretic peptide receptor (NPR-B). The invention further provides ophthalmic compositions containing such novel NPR-B agonists, and methods of treating or preventing particular ophthalmic diseases such as glaucoma, preferably by lowering intraocular pressure, using such novel NPR-B agonists. The invention is in part based on the inventors' finding that the novel NPR-B agonists described herein can provide improved bioavailability, increased chemical stability, and increased metabolic stability in body fluids or tissues, due to their significantly reduced molecular size as compared to the known natriuretic peptides. Certain embodiments of the present application generally pertain to novel peptides containing modified amino acids and that bind to and activate NPR-B with high specificity, as described in more detail herein.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

As used herein, the term "NPR-B agonist" refers to the novel molecules described herein that activate the NPR-B with high potency.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention is in part based on the finding that novel NPR-B agonists having improved bioavailability as compared to known natriuretic peptides are useful for lowering elevated intraocular pressure and treating glaucoma. Thus, the present invention is generally directed to novel NPR-B agonists and their use in methods of treating or preventing ophthalmic diseases such as glaucoma, preferably by lowering the elevated intraocular pressure often associated with glaucoma, using a pharmaceutical composition that comprises one or more novel NPR-B agonists, as described herein.

Figure 1:
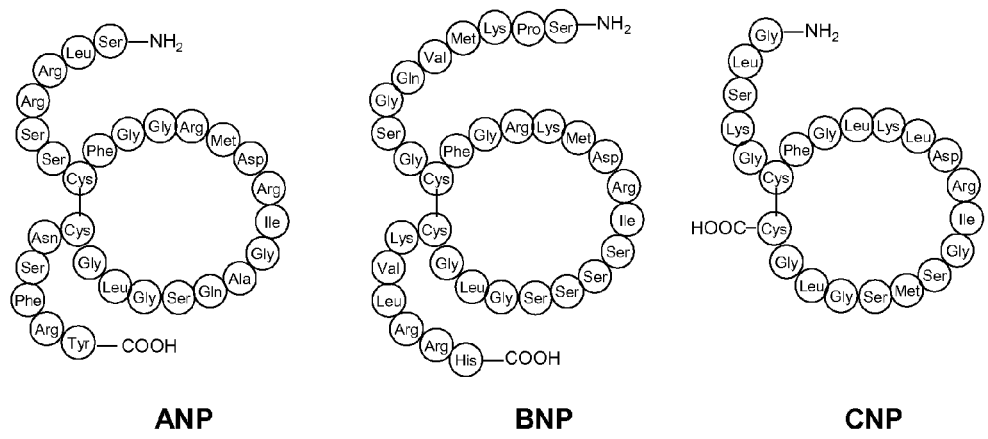
FIG. 1. Illustrates the amino acid sequence of ANP (SEQ ID NO:1), BNP (SEQ ID NO:2) and CNP (SEQ ID NO:3).
Figure 2:
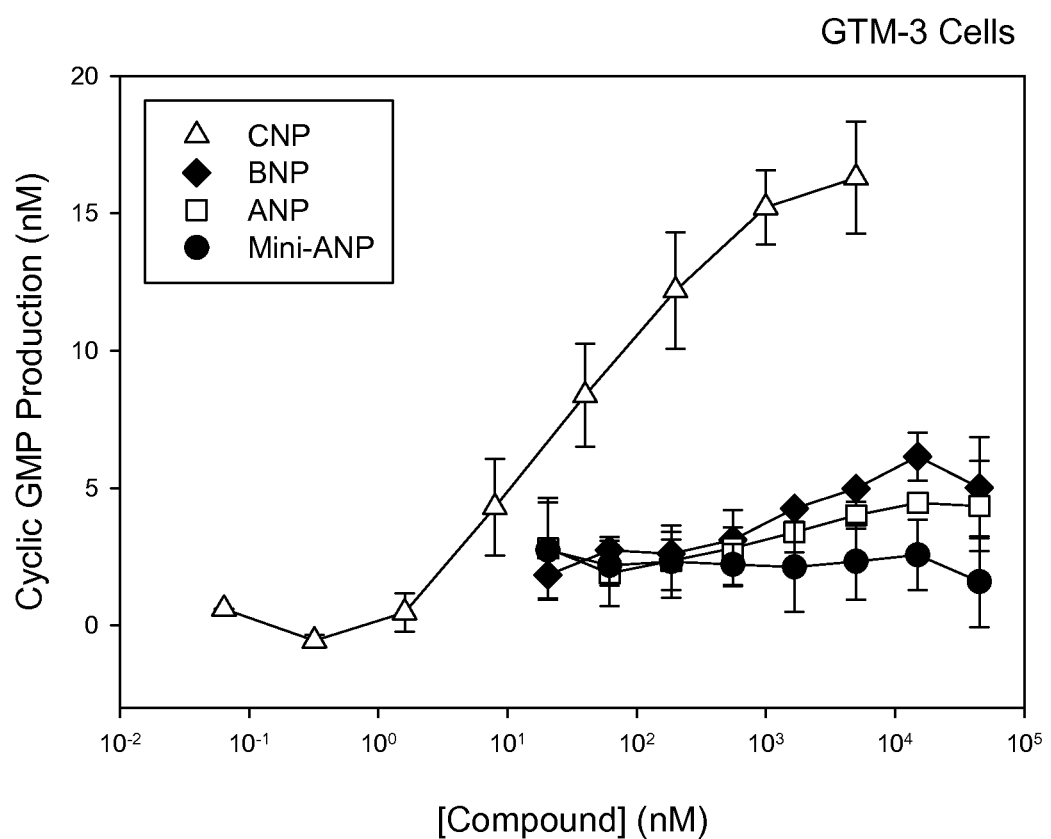
FIG. 2. Illustrates the effects of CNP, ANP, BNP and mini-ANP on cyclic GMP production in GTM-3 cells. GTM-3 cells have been shown to express NPR-B (Pang et al. 1996, *Invest Ophthalmol Vis Sci.* 37:1724-1731). The cells were treated with CNP (triangles), ANP (squares), BNP (diamonds) and mini-ANP (circles). The symbols represent mean values and standard deviations. The highest concentration of compounds used was 45 µM for ANP, BNP and mini-ANP and 5 µM for CNP. $EC_{50}$ values were determined using the 4-Parameter Logistic Equation. CNP $EC_{50}$=38.8 nM, ANP $EC_{50}$=1.63 µM, BNP $EC_{50}$=1.18 µM, mini-ANP $EC_{50}$>45 µM. The Emax (maximum activation) of each compound was determined relative to the maximum activation of CNP, i.e. CNP Emax=100%, ANP Emax=15%, BNP Emax=20% and mini-ANP Emax=0%.
Figure 3:
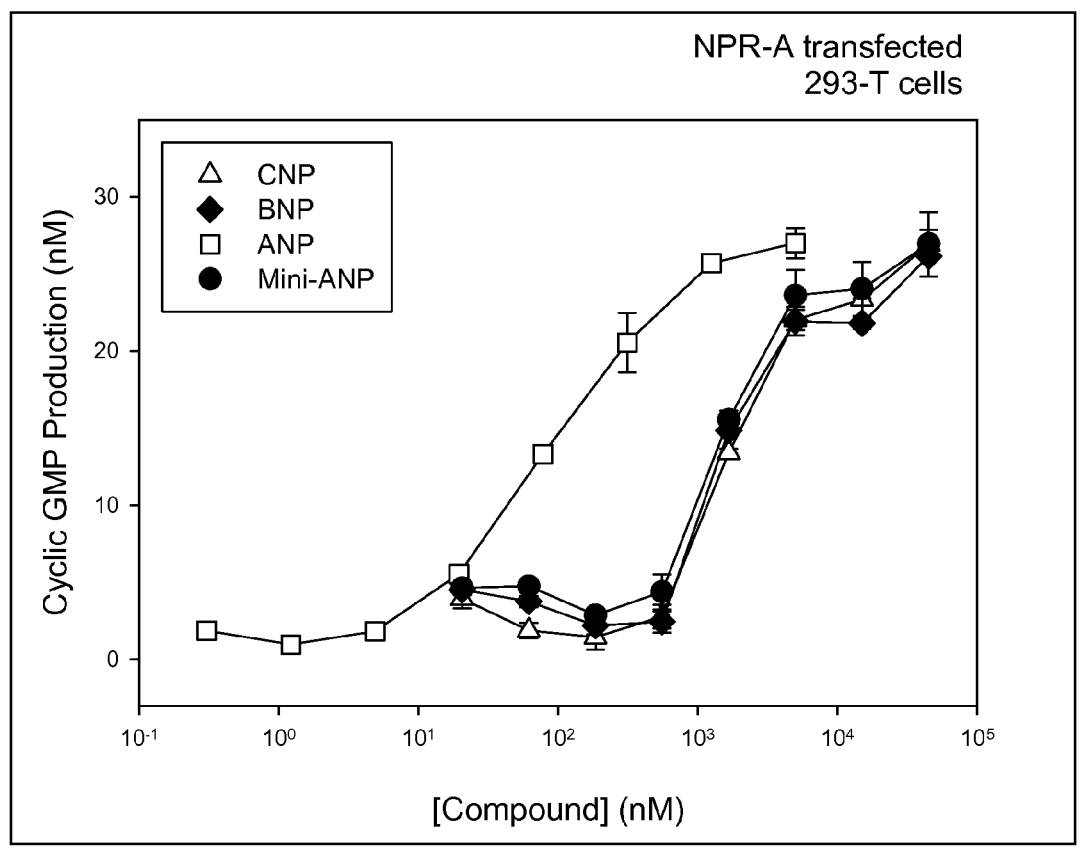
FIG. 3. Illustrates the effects of CNP, ANP, BNP and mini-ANP on cyclic GMP production in NPR-A transfected 293-T cells. NPR-A transfected 293-T cells were treated with CNP (triangles), ANP (squares), BNP (diamonds), and mini-ANP (circles). The symbols represent mean values and standard deviations. $EC_{50}$ was determined using the 4-Parameter Logistic Equation. $EC_{50}$ of ANP=73.0 nM, $EC_{50}$ of CNP=1.60 µM, $EC_{50}$ of BNP=1.85 µM, $EC_{50}$ of mini-ANP=1.54 µM.

The hallmark feature of all known NP's is the 17 amino acid ring which is formed by an intramolecular cysteine bridge (see FIG. 1). The integrity of the cyclic structure of NP's is believed to be critical for the functional activity, i.e. NP receptor transduced cGMP production. All novel NPR-B agonists described herein have a cyclic structure with a ring size that is significantly reduced as compared to known NPR-B agonists, such as CNP. It is believed that this significantly reduced ring size contributes to the increased chemical and metabolic stability and the improved bioavailability of the novel NPR-B agonists described herein.

A. NOVEL PEPTIDES

The present invention provides novel NPR-B agonists having biological activity that is improved in certain aspects as compared to that of the known natriuretic peptides. The novel peptides of the invention include conventional and non-conventional amino acids. Conventional amino acids are identified according to their standard, three-letter codes, as set forth in Table 1, below.

TABLE 1

For conventional amino acids the 3-letter codes were used:

| 3-letter codes | Amino acids | 3-letter codes | Amino acids |
| --- | --- | --- | --- |
| Ala | Alanine | Met | Methionine |
| Cys | Cysteine | Asn | Asparagine |
| Asp | Aspartic acid | Pro | Proline |
| Glu | Glutamic acid | Gln | Glutamine |
| Phe | Phenylalanine | Arg | Arginine |
| Gly | Glycine | Ser | Serine |
| His | Histidine | Thr | Threonine |
| Ile | Isoleucine | Val | Valine |
| Lys | Lysine | Trp | Tryptophane |
| Leu | Leucine | Tyr | Tyrosine |

Non-conventional amino acids are identified according to a three-letter code, or other abbreviation, when present in the novel NPR-B agonists of the invention. Table 2, below, provides the full name, three-letter code or abbreviation, and structure of each non-conventional amino acid appearing in the sequences of the novel peptides described herein.

TABLE 2

List of abbreviations of non-conventional amino acids and other chemical structures.

| Name | Abbreviation | Structure |
| --- | --- | --- |
| (R)-2-Amino-butyric acid | abu | 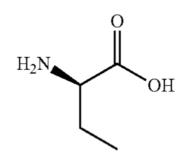 |
| 2-Amino-isobutyric acid | Aib | 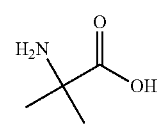 |
| (R)-α-Methyl-proline | Amp | 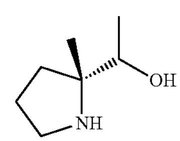 |
| (2S,4S)-4-Amino-pyrrolidine-2-carboxylic acid | Apr | 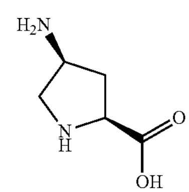 |
| (S)-2-Amino-3-(4-carbamimidoyl-phenyl)-propionic acid | Aof | 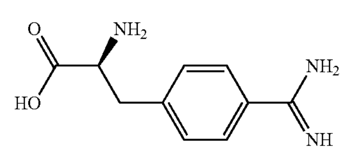 [SMILES: N=C(N)c1ccc(C[C@H](N)C(=O)O)cc1] |

TABLE 2-continued

List of abbreviations of non-conventional amino acids and other chemical structures.

| Name | Abbreviation | Structure |
| --- | --- | --- |
| 4-Amino-tetrahydro-pyran-4-carboxylic acid | Atp | 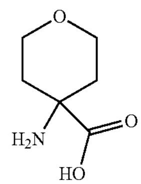 |
| 4-Amino-tetrahydro-thiopyran-4-carboxylic acid | Att | 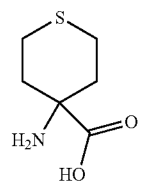 |
| Azetidine-3-carboxylic acid | Az3 | 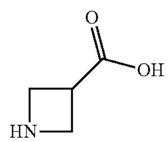 |
| (S)-Azetidine-2-carboxylic acid | Aze | 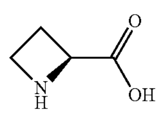 |
| (R)-Azetidine-2-carboxylic acid | aze | 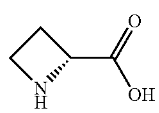 |
| β-Alanine | Bal | 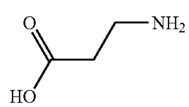 |
| 1-Amino-cyclohexane acetic acid | Bca | 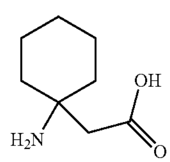 [SMILES: NC1(CC(=O)O)CCCCC1] |
| (S)-2-Amino-5-(N'-dimethyl-guanidino)-pentanoic acid | Bmr | 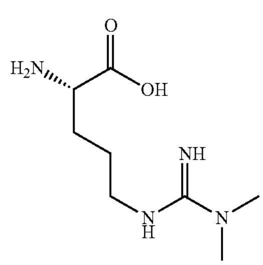 |
| Butane-1-sulfonic acid | ButSO2 | 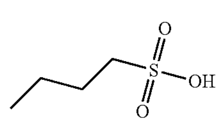 |
| 2-Aminoethanethiol | Cea | 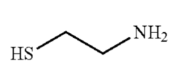 |

TABLE 2-continued

List of abbreviations of non-conventional amino acids and other chemical structures.

| Name | Abbreviation | Structure |
|---|---|---|
| (S)-Cyclohexylalanine | Cha | 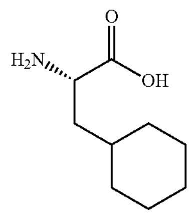 [SMILES: N[C@@H](CC1CCCCC1)C(=O)O] |
| (2S,4S)-4-Hydroxy-pyrrolidine-2-carboxylic acid | Chy | 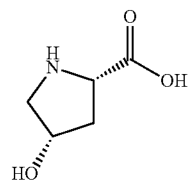 |
| (S)-Cyclohexylglycine | Chg | 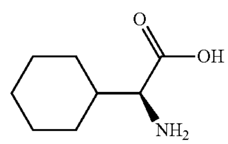 |
| (R)-Cysteic acid | Cya | 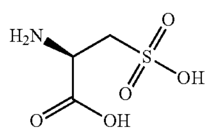 |
| (S)-2-Amino-5-(4,5-dihydro-1H-imidazol-2-ylamino)-pentanoic acid | Cyr | 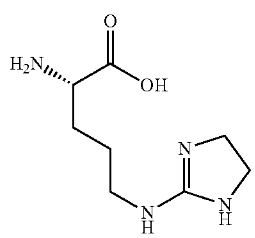 [SMILES: N[C@@H](CCCNC1=NCCN1)C(=O)O] |
| (S)-2,4-Diaminobutyric acid | Dab | 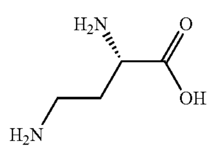 |
| (S)-2-Amino-3-dimethylamino-propionic acid | Dap(Me2) | 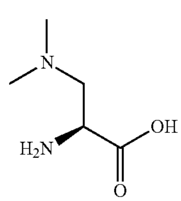 |
| (R)-2-Amino-3-dimethylamino-propionic acid | dap(Me2) | 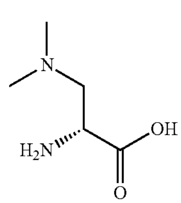 |

TABLE 2-continued

List of abbreviations of non-conventional amino acids and other chemical structures.

| Name | Abbreviation | Structure |
| --- | --- | --- |
| 2-Amino-2-ethyl-butyric acid | Deg | 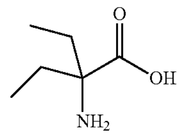 |
| (S)-2-Amino-5-(N',N'-dimethyl-guanidino)-pentanoic acid | Dmr | 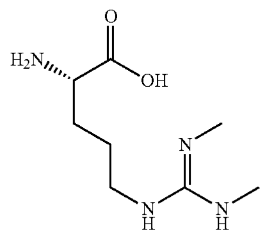 |
| (R)-Thiazolidine-4-carboxylic acid | Eaz | 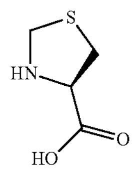 |
| 1-Amino-cyclopropane carboxylic acid | Ebc | 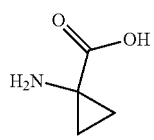 |
| 1-Amino-cyclopentane carboxylic acid | Eca | 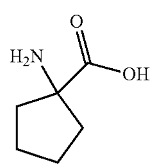 |
| 1-Amino-cyclohexane carboxylic acid | Ecb | 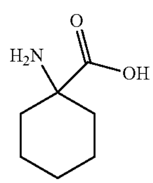 |
| (S)-meta-Nitro-phenylalanine | Egz | 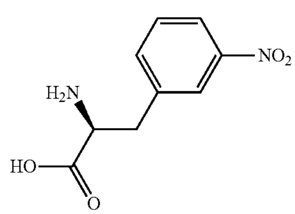 [SMILES: N[C@@H](Cc1cccc([N+](=O)[O-])c1)C(=O)O] |
| Propionic acid | EtCO | 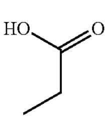 |
| (S)-2-Amino-(4-N-piperidinyl)-acetic acid | Fhz | 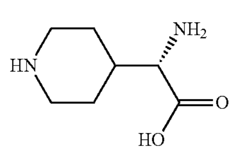 [SMILES: N[C@H](C(=O)O)C1CCNCC1] |

TABLE 2-continued

List of abbreviations of non-conventional amino acids and other chemical structures.

| Name | Abbreviation | Structure |
|---|---|---|
| 4-Amino-butyric acid | Gab | 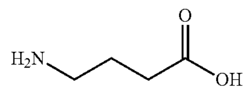 |
| (S)-4-Guanidine-phenylalanine | Guf | 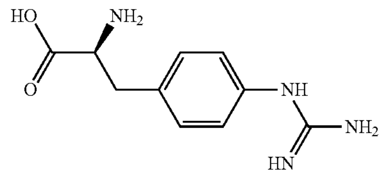 [SMILES: N=C(N)Nc1ccc(C[C@H](N)C(=O)O)cc1] |
| (S)-Homo-arginine | Har | 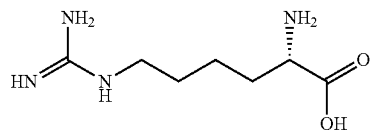 [SMILES: N=C(N)NCCCC[C@H](N)C(=O)O] |
| (S)-Homo-cysteine | Hcy | 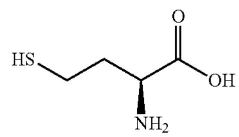 |
| Hexanoic acid | Hex | 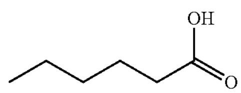 |
| (S)-2-Amino-octanoic acid | Hgl | 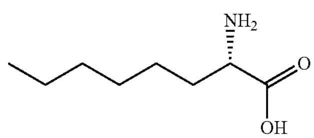 |
| (R)-2-Amino-octanoic acid | hgl | 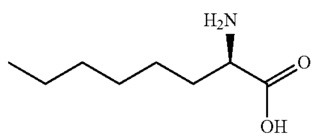 |
| (S)-2-Amino-5-methyl-hexanoic acid | Hle | 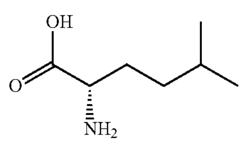 |
| (S)-Homo-lysine | Hly | 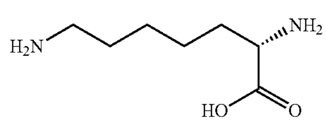 [SMILES: NCCCCC[C@H](N)C(=O)O] |
| (S)-2-Amino-4-(N-piperidin-4-yl)-butyric acid | Hpa | 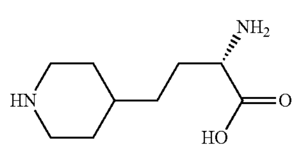 [SMILES: N[C@@H](CCC1CCNCC1)C(=O)O] |
| (2S,3S)-3-Hydroxy-pyrrolidine-2-carboxylic acid | Hpr | 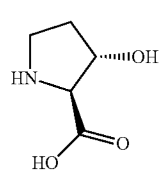 |

TABLE 2-continued

List of abbreviations of non-conventional amino acids and other chemical structures.

| Name | Abbreviation | Structure |
| --- | --- | --- |
| (2S,4R)-4-Hydroxy-pyrrolidine-2-carboxylic acid | Hyp | 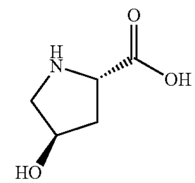 |
| 3-Methyl-butyric acid | iPrCH2CO | 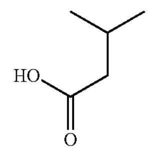 |
| 4-Methyl-pentanoic acid | iPrEtCO | 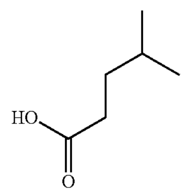 |
| 5-Methyl-hexanoic acid | iPrPrCO | 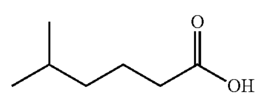 |
| (S)-meta-Bromo-phenylalanine | Mbf | 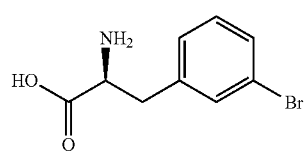 [SMILES: N[C@@H](Cc1cccc(Br)c1)C(=O)O] |
| (S)-meta-Chloro-phenylalanine | Mcf | 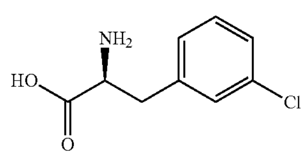 [SMILES: N[C@@H](Cc1cccc(Cl)c1)C(=O)O] |
| (S)-meta-Cyano-phenylalanine | Mcn | 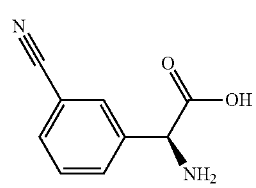 [SMILES: N#Cc1cccc([C@H](N)C(=O)O)c1] |
| (S)-meta-Fluoro-phenylalanine | Mff | 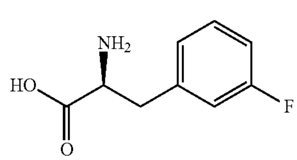 [SMILES: N[C@@H](Cc1cccc(F)c1)C(=O)O] |
| (S)-meta-Methyl-phenylalanine | Mmf | 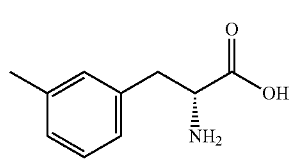 |

TABLE 2-continued

List of abbreviations of non-conventional amino acids and other chemical structures.

| Name | Abbreviation | Structure |
|---|---|---|
| (S)-2-Amino-5-(N'-methyl-guanidino)-pentanoic acid | Mmr | 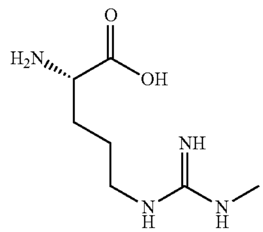 |
| (S)-meta-Methoxy-phenylalanine | Mmy | 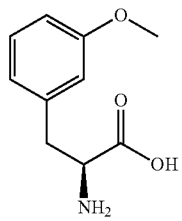 |
| (S)-meta-Trifluoromethyl-phenylalanine | Mtf | 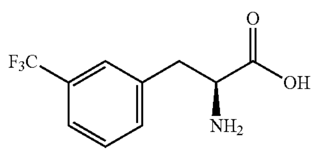 [SMILES: N[C@@H](Cc1cccc(C(F)(F)F)c1)C(=O)O] |
| (S)-2-Amino-4-guanidino-butyric acid | Nar | 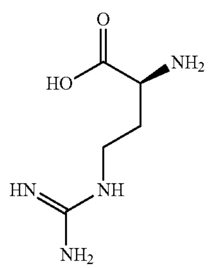 [SMILES: N=C(N)NCC[C@H](N)C(=O)O] |
| (S)-Norleucine | Nle | 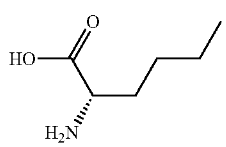 |
| (R)-Norleucine | nle | 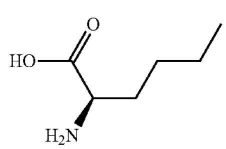 |
| (S)-N-Methyl-isoleucine | Nmi | 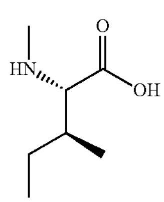 |
| (S)-N-Methyl-lysine | Nmk | 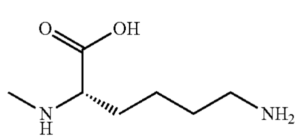 |

TABLE 2-continued

List of abbreviations of non-conventional amino acids and other chemical structures.

| Name | Abbreviation | Structure |
| --- | --- | --- |
| (S)-N-Methyl-leucine | Nml | 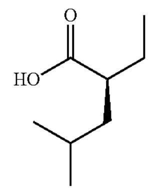 |
| (S)-N-Methyl-arginine | Nmr | 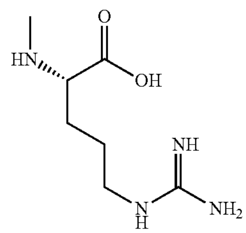 |
| (S)-2-Amino-4,4-dimethyl-pentanoic acid | Npg | 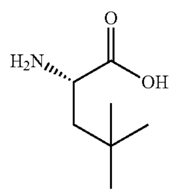 |
| (S)-2-Amino-pentanoic acid | Nva | 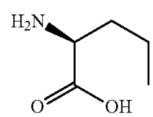 |
| Octanoic acid | Occ | 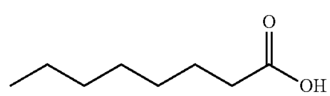 |
| (S)-ortho-Chloro-phenylalanine | Ocf | 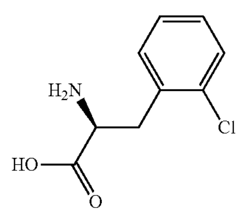 [SMILES: N[C@@H](Cc1ccccc1Cl)C(=O)O] |
| (S)-2-Amino-5-(pyridin-2-ylamino)-pentanoic acid | Opy | 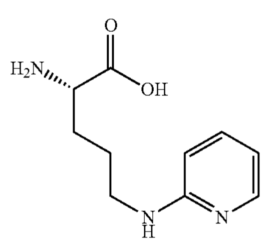 [SMILES: N[C@@H](CCCNc1ccccn1)C(=O)O] |
| (S)-Ornithine | Orn | 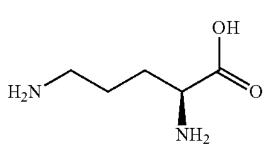 |

TABLE 2-continued

List of abbreviations of non-conventional amino acids and other chemical structures.

| Name | Abbreviation | Structure |
|---|---|---|
| (S)-para-Bromo-phenylalanine | Pbf | 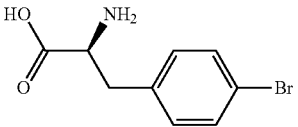 [SMILES: N[C@@H](Cc1ccc(Br)cc1)C(=O)O] |
| (S)-para-Chloro-phenylalanine | Pcf | 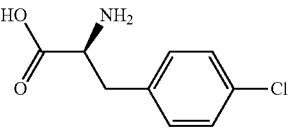 [SMILES: N[C@@H](Cc1ccc(Cl)cc1)C(=O)O] |
| Benzoic acid | PhCO | 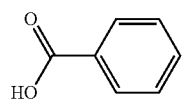 |
| (S)-para-Fluoro-phenylalanine | Pff | 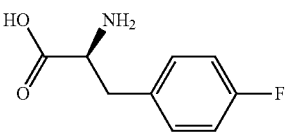 [SMILES: N[C@@H](Cc1ccc(F)cc1)C(=O)O] |
| 3-Phenyl-propionic acid | PhEtCO | 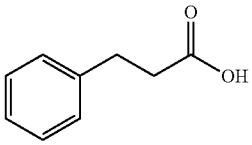 [SMILES: O=C(O)CCc1ccccc1] |
| Phenyl-acetic acid | PhCH2CO | 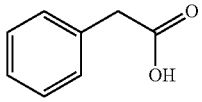 |
| (S)-Pipecolinic acid | Pip | 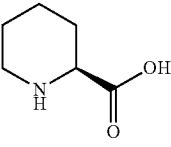 |
| (R)-Pipecolinic acid | pip | 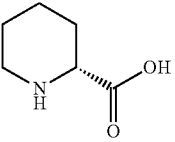 |
| 4-Phenyl-butyric acid | PhPrCO | 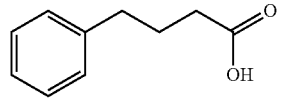 [SMILES: O=C(O)CCCc1ccccc1] |
| (S)-2-Amino-4-(2-amino-pyrimidin-4-yl)-butyric acid | Rpy | 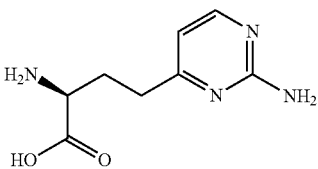 [SMILES: Nc1nccc(CC[C@H](N)C(=O)O)n1] |

TABLE 2-continued

List of abbreviations of non-conventional amino acids and other chemical structures.

| Name | Abbreviation | Structure |
|---|---|---|
| (S)-Nipecotic acid | Sni | 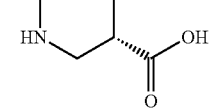 |
| (2S,4R)-4-Amino-pyrrolidine-2-carboxylic acid | Tap | 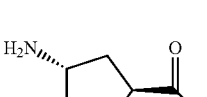 |
| (S)-α-tert-Butylglycine | Tbg | 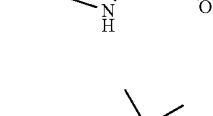 |
| (2S,4R)-4-Fluoro-pyrrolidine-2-carboxylic acid | Tfp | 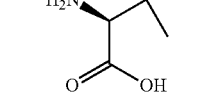 |
| (R)-2-Thienyl-alanine | Thi | 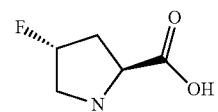 |
| (S)-Thiazolidine-4-carboxylic acid | Thz | 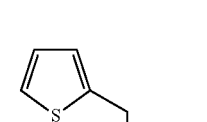 |

The novel NPR-B agonists of the invention comprise the general amino acid sequence of Formula I:

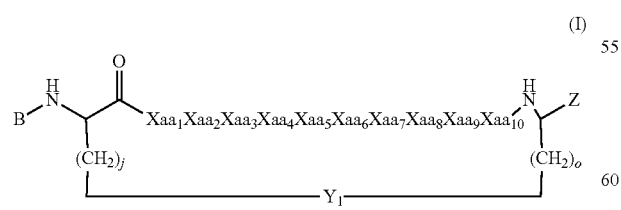

wherein $Xaa_1$ is selected from the group consisting of a conventional amino acid; a non-conventional α-amino acid; a β-amino acid; and a γ-amino acid;

$Xaa_2$ is an amino acid residue of Formula II:

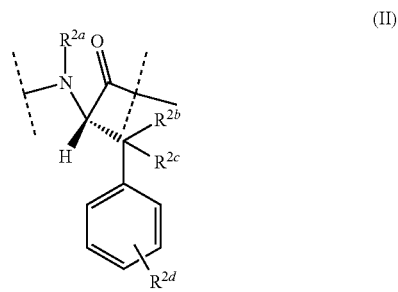

wherein $R^{2a}$ is selected from the group consisting of H, methyl, ethyl, propyl, and isopropyl;

$R^{2b}$ and $R^{2c}$ are, independently, selected from the group consisting of H, methyl, ethyl, propyl; and isopropyl, with the proviso that at least one of $R^{2b}$ and $R^{2c}$ is H;

$R^{2d}$ represents from 0 to 3 substituents, each such substituent being, independently, selected from the group consisting of H, Cl, F, Br, $NO_2$, CN, $CF_3$, and $C_1$-$C_4$ alkyl;

$R^{2a}$ and $R^{2b}$ or $R^{2a}$ and $R^{2c}$ may form a heterocyclic ring; and Xaa$_3$ is selected from the group consisting of Gly, a conventional D-α-amino acid, a non-conventional D-α-amino acid, and an amino acid residue of Formula III:

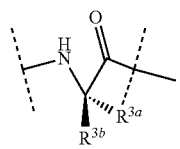

(III)

wherein $R^{4a}$ and $R^{3b}$ are, independently, selected from the group consisting of H and $C_{1-4}$alkyl;

wherein $R^{3a}$ and $R^{3b}$ can form a cyclic structure;

or $R^{3a}$ and $R^{3b}$ can be linked with a heteroatom selected from the group consisting of N, O, and S, to form a heterocyclic structure; and Xaa$_4$ is an amino acid residue of Formula IV:

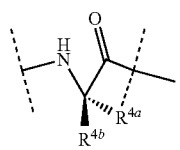

(IV)

wherein $R^{4a}$ is selected from the group consisting of H, unbranched $C_{1-8}$alkyl, and branched $C_{1-8}$alkyl, wherein said branched or unbranched $C_{1-8}$alkyl may be substituted with a moiety selected from the group consisting of OH, $CO_2R^{4c}$, $C(=O)$—$NH_2$, a 5-6 membered heteroaryl, $C_1$-$C_{10}$alkyl, alkylcycloalkyl, and $C_{5-8}$cycloalkyl;

$R^{4b}$ is selected from the group consisting of H and methyl;

$R^{4c}$ is selected from the group consisting of H, and $C_{1-3}$alkyl; and

Xaa$_5$ is an amino acid residue of Formula V:

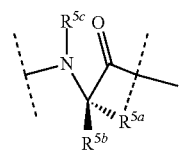

(V)

wherein $R^{5a}$ is $(CH_2)_nX^{5a}$;

n is 2-6;

$X^{5a}$ is selected from the group consisting of H, $NH_2$, and a $C_{4-7}$ nitrogen-containing aliphatic heterocyclic ring;

$R^{5b}$ is selected from the group consisting of H and methyl;

$R^{5c}$ is selected from the group consisting of H and methyl; and wherein $R^{5c}$ and $R^{5a}$ can combine to form a heterocyclic ring of Formula VI:

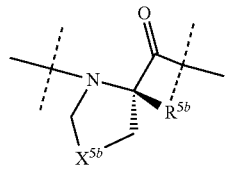

(VI)

wherein $X^{5b}$ is selected from the group consisting of a direct bond, $(CH_2)_p$, $(CH_2)_qS$, and $S(CH_2)_q$;

p=1-4;

q=0-2;

and wherein said heterocyclic ring may be substituted with a moiety selected from the group consisting of OH, F, and $NH_2$; and Xaa$_6$ is an amino acid residue of Formula VII:

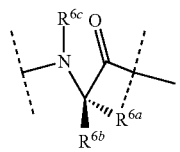

(VII)

wherein $R^{6a}$ is selected from the group consisting of $C_{1-8}$alkyl, and $C_4$-7cycloalkyl, wherein said $C_{1-8}$alkyl and $C_{4-7}$cycloalkyl may be substituted with a moiety selected from the group consisting of OH, $O(C_{1-4}$ alkyl), $S(C_{2-4}$alkyl), and $NR^{6d}R^{6e}$;

$R^{6b}$ is H;

$R^{6c}$ is selected from the group consisting of H, and methyl;

$R^{6d}$, and $R^{6e}$ are, independently, selected from the group consisting of H, and $C_{1-4}$ alkyl; and Xaa$_7$ is an amino acid residue of Formula VIII:

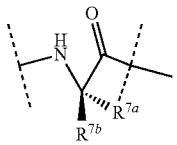

(VIII)

wherein $R^{7a}$ is selected from the group consisting of $C_{3-5}$ cycloalkyl, $(CH_2)X^7$, $C_{1-4}$alkyl, and $C_{1-4}$alkyl substituted with OH;

$R^{7b}$ is H;

$X^7$ is selected from the group consisting of $C(=O)OR^{7c}$, $C(=O)NH_2$, $S(=O)_2OH$, $OS(=O)_2OH$, $B(OH)_2$, $P(=O)(OH)_2$, and $OP(=O)(OH)_2$;

$R^{7c}$ is selected from the group consisting of H, and $C_{1-3}$ alkyl; and

Xaa$_8$ is an amino acid residue of Formula IX:

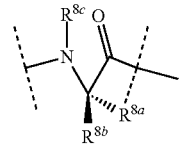

(IX)

wherein $R^{8a}$ is selected from the group consisting of $(CH_2)X^{8a}$, $(CH_2)_mX^{8b}$, and a $C_{4-7}$ nitrogen-containing aliphatic heterocyclic ring;

m=1-5;

$X^{8a}$ is selected from the group consisting of H, 3-imidazo, 4-(benzenecarboximidamide), and 3-(benzenecarboximidamide);

$X^{8b}$ is selected from the group consisting of $NH_2$, 4-(2-aminopyrimidyl), 2-aminopyridine, and $N(R^{8d})C(=X^{8c})NR^{8e}R^{8f}$; $X^{8c}$ is selected from the group consisting of O, and $NR^{8g}$;

$R^{8c}$, $R^{8d}$, $R^{8e}$, $R^{8f}$, and $R^{8g}$ are, independently, selected from the group consisting of H, and $C_{1-3}$ alkyl, wherein when any one or more of $R^{8e}$, $R^{8f}$, and $R^{8g}$ is $C_{1-3}$alkyl, $R^{8g}$ can combine with either of $R^{8e}$ or $R^{8f}$ to form a cyclic structure;

$R^{8b}$ is H;

$R^{8a}$ and $R^{8e}$ can form a cyclic structure; and $Xaa_9$ is an amino acid residue of Formula X:

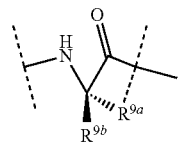 (X)

wherein $R^{9a}$ is selected from the group consisting of unbranched $C_{2-5}$alkyl, branched $C_{2-5}$alkyl, and $C_{4-7}$ cycloalkyl;

$R^{9b}$ is selected from the group consisting of H, and $C_{2-5}$ alkyl;

and wherein $R^{9a}$ and $R^{9b}$ can form a 5-7 membered cycloalkyl, or 5-7 membered aliphatic heterocyclic ring containing either O or S; and $Xaa_{10}$ is an amino acid residue of Formula XI:

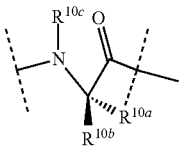 (XI)

wherein $R^{10a}$ is selected from the group consisting of H, and $(CH_2)OH$;

$R^{10b}$ is H; H and $R^{10c}$ is selected from the group consisting of H, and $C_{1-3}$alkyl; and wherein

represents a peptide bond connecting an amino acid residue to the amino acid residues at the position immediately preceding and immediately succeeding said amino acid residue;

$Y_1$ is selected from the group consisting of —S—, —O—, —S—S—, —CO—NH—, and —NH—CO—; and j and o are, independently, 1 or 2;

B is at least one moiety selected from the group consisting of H, a conventional amino acid; a non-conventional amino acid; $C_{1-10}$alkyl; alkanoyl; sulfanoyl; alkylcycloalkyl; aralkyl; a protein; an antibody; a polymer consisting of up to about 50 monomers selected from the group consisting of ethylene, propylene, an ester-, an ether- and a thioester; and a peptide consisting of from 2 to 30 amino acids selected from the group consisting of conventional α-amino acids, non-conventional α-amino acids, and β-amino acids; and Z is at least one moiety selected from the group consisting of H, —$CH_2$—OH, and —C(=O)—$X^{11}$, wherein $X^{11}$ is selected from the group consisting of OH, —$NR^{11}R^{13}$, —$OR^{14}$, a conventional α-amino acid, a non-conventional α-amino acid, a β-amino acid; and a peptide consisting of from 2 to 30 amino acids selected from the group consisting of conventional α-amino acids, non-conventional α-amino acids, and β-amino acids;

wherein $R^{11}$ and $R^{13}$ are, independently, selected from the group consisting of H and $C_{1-6}$alkyl;

$R^{14}$ is selected from the group consisting of H, $C_{1-10}$alkyl, and alkylcycloalkyl.

The present inventors do not intend that the compound of Formula I, as described above, encompass mini-ANP (SEQ ID N0:4). To the extent that any embodiment of Formula I, as described herein, encompasses mini-ANP, that embodiment is hereby disclaimed.

In certain preferred embodiments of the present invention, the novel NPR-B agonists of the invention comprise the general amino acid sequence of Formula XII:

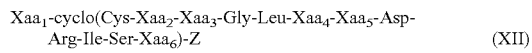 (XII)

wherein $Xaa_1$ is selected from the group consisting of Met, Hex, iPrEtCO$_3$ iPrPrCO, Occ, PhEtCO$_3$ and PhPrCO, provided that when $Xaa_1$ is iPrEtCO$_3$ iPrPrCO, Occ, PhEtCO$_3$ or PhPrCO then $Xaa_2$ is ala, $Xaa_3$ is Phe, $Xaa_4$ is Lys, $Xaa_5$ is Leu, $Xaa_6$ is Cys, and Z is $NH_2$;

$Xaa_2$ is selected from the group consisting of ala, aze, thz, pip and pro, provided that when $Xaa_2$ is aze, thz, pip or pro then $Xaa_1$ is Hex;

$Xaa_3$ is selected from the group consisting of Phe, Mcf and Mmf, provided that when $Xaa_3$ is Mcf or Mmf then $Xaa_1$ is Hex;

$Xaa_4$ is selected from the group consisting of Pro, Lys, Hpa and Hpr, provided that when $Xaa_4$ is Hpa or Hpr then $Xaa_1$ is Hex;

$Xaa_5$ is selected from the group consisting of Leu, Ile, Nle, and Npg, provided that when $Xaa_5$ is Nle or Npg then $Xaa_1$ is Hex;

$Xaa_6$ is selected from the group consisting of Cys and Cea, provided that when $Xaa_6$ is Cea then $Xaa_1$ is Met or Hex and Z is H; and Z is selected from the group consisting of $NH_2$ and H.

In certain preferred embodiments of the present invention, the novel NPR-B agonists of the invention comprise the general amino acid sequence of Formula XIII:

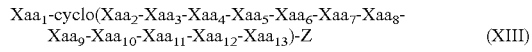 (XIII)

wherein $Xaa_1$ is selected from the group consisting of Met, met, Hex, Nle, EtCO, iPrCH$_2$CO, PhCO, PhCH$_2$CO, and ButSO$_2$, provided that when $Xaa_1$ is Nle then $Xaa_3$ is Gly, and when $Xaa_1$ is EtCO, iPrCH$_2$CO, PhCO, PhCH$_2$CO or ButSO$_2$ then $Xaa_2$ is Cys, $Xaa_3$ is ala, $Xaa_4$ is Phe, $Xaa_5$ is Gly, $Xaa_6$ is Leu, $Xaa_7$ is Lys, $Xaa_8$ is Leu, $Xaa_9$ is Asp, $Xaa_{10}$ is Arg, $Xaa_{11}$ is Ile, $Xaa_{12}$ is Ser, and $Xaa_{13}$ is Cys;

$Xaa_2$ is selected from the group consisting of Cys and Hcy, provided that when $Xaa_2$ is Hcy then $Xaa_1$ is Met;

Xaa₃ is selected from the group consisting of ala, Ala, His, his, Gly, Ser, ser, Bal, pro, asn and thi, provided that when Xaa₃ is Ala, Gly, Ser, Bal, pro, ser, asn or thi then Xaa₁ is Met, and when Xaa₃ is Gly then Xaa₁ is Nle or Met and Xaa₅ is ala or Gly;

Xaa₄ is selected from the group consisting of Phe, Ocf, Eau, Mff, Mch, Egz and Mmy, provided that when Xaa₄ is Ocf, Eau, Mff, Mch, Egz or Mmy then Xaa₁ is Hex;

Xaa₅ is selected from the group consisting of Gly, ala and Aib, provided that when Xaa₅ is Aib then Xaa₃ is his and Xaa₁ is Met, and when Xaa₅ is ala then Xaa₁ is Met;

Xaa₆ is selected from the group consisting of Leu, Asp, His, Thr, Ala, and Gly, provided that when Xaa₆ is Asp or His then Xaa₁ is Met, and when Xaa₆ is Thr, Ala or Gly then Xaa₁ is Hex;

Xaa₇ is selected from the group consisting of Lys, Pro, Aze, Amp, Arg, Nmk, Dab, Orn, and Hly, provided that when Xaa₇ is Aze then Xaa₁ is Hex, and when Xaa₇ is Amp, Arg, Nmk, Dab, Orn or Hly then Xaa₁ is Met;

Xaa₈ is selected from the group consisting of Leu, Nml, Val, Tbg, and Chg, provided that when Xaa₈ is Val, Tbg or Chg then Xaa₁ is Hex, and when Xaa₈ is Nml then Xaa₁ is Met;

Xaa₉ is selected from the group consisting of Asp and Cya, provided that when Xaa₉ is Cya then Xaa₁ is Met;

Xaa₁₀ is selected from the group consisting of Arg, Nmr, Har, Orn, Cyr, Mmr, Dmr, Opy, Fhz and Rpy, provided that when Xaa₁₀ is Har, Orn, Cyr, Mmr, Dmr, Opy or Rpy then B is Hex, and when Xaa₁ is Nmr then Xaa₁ is Met, and when Xaa₁₀ is Fhz then Xaa₂ is Pro and Xaa₁ is Hex;

Xaa₁₁ is selected from the group consisting of Ile, Tbg, Leu, Val, Eca, Ecb, Bca and Chg, provided that when Xaa₁₁ is Tbg, Lue or Val then Xaa₁ is Met, and when Xaa₁₁ is Eca, Ecb, Bca or Chg then Xaa₁ is Hex;

Xaa₁₂ is selected from the group consisting of Ser and Bal, provided that when Xaa₁₂ is Bal then Xaa₁ is Met;

Xaa₁₃ is selected from the group consisting of Cys and Hcy, provided that when Xaa₁₃ is Hcy then Xaa₂ is Hcy and Xaa₁ is Met; and Z is selected from the group consisting of NH₂, Tyr-Arg-NH₂, Tyr-NH₂, Asn-Arg-NH₂, Leu-Arg-NH₂, Ser-Arg-NH₂, Tyr-Asn-NH₂, and Tyr-His-NH₂, provided that when Z is anything other than NH₂ then Xaa₁ is Met, Xaa₂ is Cys, Xaa₃ is His, Xaa₄ is Phe, Xaa₅ is Gly, Xaa₆ is Leu, Xaa₇ is Lys, Xaa₈ is Leu, Xaa₉ is Asp, Xaa₁₀ is Arg, Xaa₁₁ is Ile, Xaa₁₂ is Ser, and Xaa₁₃ is Cys.

In certain preferred embodiments of the present invention, the novel NPR-B agonists of the invention comprise the general amino acid sequence of Formula XIV:

Xaa₁-cyclo(Cys-Xaa₂-Xaa₃-Gly-Xaa₄-Lys-Leu-Asp-Xaa₅-Xaa₆-Ser-Cys)-Z    (XIV)

wherein

Xaa₁ is selected from the group consisting of Met, Hex, Nle and H, provided that when Xaa₁ is Nle then Xaa₂ is His, Xaa₃ is Phe, Xaa₄ is Leu, Xaa₅ is Arg, Xaa₆ is Ile, and Z is NH₂, and when Xaa₁ is H, then Xaa₂ is ala, Xaa₃ is Phe, Xaa₄ is Leu, Xaa₅ is Arg, Xaa₆ is Ile, and Z is NH₂;

Xaa₂ is selected from the group consisting of His, Gab, phe and ala, provided that when Xaa₂ is Gab or phe then Xaa₁ is Met;

Xaa₃ is selected from the group consisting of Phe, Pcf, Pff, and Mtf, provided that when Xaa₃ is Pcf, or Pff then Xaa₁ is Met, and when Xaa₃ is Mtf then Xaa₁ is Hex;

Xaa₄ is selected from the group consisting of Leu and Ala, provided that when Xaa₄ is Ala then Xaa₁ is Met;

Xaa₅ is selected from the group consisting of Arg, Bmr, Aof, and Nar, provided that when Xaa₅ is Bmr, Aof or Nar then Xaa₁ is Hex, Xaa₂ is ala, Xaa₃ is Phe, Xaa₄ is Leu, Xaa₆ is Ile and Z is NH₂;

Xaa₆ is selected from the group consisting of Ile, Atp and Att, provided that when Xaa₆ is Atp or Att then Xaa₁ is Hex, Xaa₂ is ala, Xaa₃ is Phe, Xaa₄ is Leu, Xaa₅ is Arg and Z is NH₂; and Z is selected from the group consisting of NH₂, Trp-Arg-NH₂, His-Arg-NH₂; OH, and Tyr-Ser-NH₂, provided that when Z is anything other than NH₂ then Xaa₁ is Met, Xaa₂ is His, Xaa₃ is Phe, Xaa₄ is Leu, Xaa₅ is Arg, and Xaa₆ is Ile.

The sequences of the preferred novel NPR-B agonists of the invention are provided herein in typical peptide sequence format, as would be understood by the ordinary skilled artisan. For example, the three-letter code of a conventional amino acid, or the abbreviation for a non-conventional amino acid, indicates the presence of a particular amino acid in a specified position in the sequence of the molecule, each amino acid being connected to the next and/or previous amino acid by a hyphen. The hyphen, which represents a chemical bond, typically an amide bond, removes OH from the 1-carboxyl group of the amino acid when it is placed right of the abbreviation, and removes H from the 2-amino group (or the only present amino group in case of amino acids lacking a 2-amino group, e.g., Bal) of the amino acid when it is placed on the left of the abbreviation. It is understood that both modifications can apply to one amino acid.

In the case of additional functional groups in the side chains of conventional or non-conventional amino acids, only the 2-amino and/or the 1-carboxy group is used for the formation of peptide bonds.

The C-termini of the novel NPR-B agonists described herein are shown in explicit form by adding either OH, NH₂ or an abbreviation for a specific terminating amine separated by a hyphen on the right of the abbreviation of the C-terminal amino acid.

These specific terminating amines are provided in Table 2 as full formulas and similar conventions with regard to hyphens and its structure in a peptide context apply to them, e.g.,

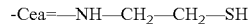

The N-termini of the novel peptides described herein are shown in explicit form by adding either H (for a free N-terminus), or an abbreviation for a specific terminating carboxylic acid or sulfonic acid in front of the symbol of the N-terminal amino acid (or in front of the prefix "cyclo," in the case of cyclic peptides), separated by an hyphen.

These specific terminating carboxylic acids or sulfonic acids are provided in Table 2 as full formulas and similar conventions with regard to hyphens and its structure in a peptide context apply to them, e.g., Hex=Hexanoic acid Hex-=Hexanoyl- For conventional amino acids, a 3-letter code was used where the first letter indicates the stereochemistry of the C-alpha-atom. For example, a capital first letter indicates that the L-form of the amino acid is present in the peptide sequence, while a lower case first letter indicates that the D-form of the correspondent amino acid is present in the peptide sequence.

In preferred embodiments of the present invention, the novel NPR-B agonist is a 12 amino acid cyclic peptide having a sequence as set forth in Table 3. The phrase "12 amino acid cyclic peptide" refers to a peptide having a bond between two amino acids to create a cyclic structure having 12 amino acids within the cyclic portion of the peptide. It is contemplated that additional amino acids may be present either before or after the cyclic portion of the peptide. As can be seen in the sequences set forth in Table 3, in many instances, the 12 amino acid cyclic peptide may be preceded or followed by additional amino acids to form a peptide having from 12 to 15 amino acids. In preferred aspects, the 12 amino acid cyclic peptide is preceded by a single amino acid, creating a 13 amino acid peptide having a cyclic structure created by a bond between the amino acid at position 2 and the amino acid at position 13. The agonistic activity of the preferred compounds is also provided in Table 3 and was categorized based upon the following conventions:

| NPR-B activation (assayed with GTM-3 Cells) | | |
|---|---|---|
| $EC_{50}$ | Emax (CNP = 100%) | Group |
| ≤1 μM | >50% | A |
| ≤5 μM | >20% | B |
| ≤15 μM | >10% | C |

The agonistic activity data of each compound was checked first to determine whether it fulfills the criteria for the activity group A. If it did not fulfill the criteria for activity group A, it was checked for group B criteria. If it did not fulfill the criteria for activity group A or activity group B, it was finally checked for group C criteria. If it did not fulfill the criteria for activity group C, it was not included in Table 3.

All examples in Table 3 are cyclic peptides written in three letter code. The cyclized part of the peptide is highlighted in brackets and the prefix cyclo is used. The side chain of the residue following "cyclo(" is covalently bound to the sulfur atom which is part of the residue preceeding ")". This is a nomenclature which is commonly used and is known to experts in the field.

TABLE 3

Data for agonistic activity of selected compounds according to the present invention.

| Compound | SEQ ID NO: | $(M + H)^+$ in MS [amu] | Activity (group) |
|---|---|---|---|
| H-Met-cyclo(Cys-His-Phe-Gly-Leu-Lys-Leu-Asp-Arg-Ile-Ser-Cys)-Tyr-Arg-$NH_2$ | 5 | 1840 | B |
| H-Met-cyclo(Cys-His-Phe-Gly-Leu-Lys-Leu-Asp-Arg-Ile-Ser-Cys)-Tyr-$NH_2$ | 6 | 1684 | B |
| H-Met-cyclo(Cys-His-Phe-Gly-Leu-Lys-Leu-Asp-Arg-Ile-Ser-Cys)-$NH_2$ | 7 | 1520 | B |
| H-Met-cyclo(Cys-Ala-Phe-Gly-Leu-Lys-Leu-Asp-Arg-Ile-Ser-Cys)-$NH_2$ | 8 | 1455 | B |
| H-Met-cyclo(Cys-His-Phe-Gly-Ala-Lys-Leu-Asp-Arg-Ile-Ser-Cys)-$NH_2$ | 9 | 1479 | C |
| H-met-cyclo(Cys-His-Phe-Gly-Leu-Lys-Leu-Asp-Arg-Ile-Ser-Cys)-$NH_2$ | 10 | 1522 | B |
| H-Met-cyclo(cys-His-Phe-Gly-Leu-Lys-Leu-Asp-Arg-Ile-Ser-Cys)-$NH_2$ | 11 | 1522 | C |
| H-Met-cyclo(Cys-his-Phe-Gly-Leu-Lys-Leu-Asp-Arg-Ile-Ser-Cys)-$NH_2$ | 12 | 1522 | B |
| H-Met-cyclo(cys-His-Phe-Gly-Leu-Lys-Leu-Asp-Arg-Ile-Ser-cys)-$NH_2$ | 13 | 1522 | C |
| Ac-Met-cyclo(Cys-His-Phe-Gly-Leu-Lys-Leu-Asp-Arg-Ile-Ser-Cys)-$NH_2$ | 14 | 1563 | B |
| H-Met-cyclo(Cys-His-Phe-Gly-Leu-Lys-Leu-Asp-Arg-Ile-Ser-Cys)-OH | 15 | 1522 | C |
| H-Nle-cyclo(Cys-His-Phe-Gly-Leu-Lys-Leu-Asp-Arg-Ile-Ser-Cys)-$NH_2$ | 16 | 1503 | C |
| H-Met-cyclo(Cys-Gly-Phe-Gly-Leu-Lys-Leu-Asp-Arg-Ile-Ser-Cys)-$NH_2$ | 17 | 1441 | B |
| H-Met-cyclo(Cys-Ser-Phe-Gly-Leu-Lys-Leu-Asp-Arg-Ile-Ser-Cys)-$NH_2$ | 18 | 1471 | B |
| H-Met-cyclo(Cys-His-Phe-Gly-Asp-Lys-Leu-Asp-Arg-Ile-Ser-Cys)-$NH_2$ | 19 | 1524 | B |
| H-Met-cyclo(Cys-His-Phe-Gly-His-Lys-Leu-Asp-Arg-Ile-Ser-Cys)-$NH_2$ | 20 | 1546 | B |
| H-Met-cyclo(Cys-His-Phe-Gly-Leu-Lys-Leu-Asp-Arg-Ile-Ser-Cys)-Trp-Arg-$NH_2$ | 21 | 1863 | C |
| H-Met-cyclo(Cys-His-Phe-Gly-Leu-Lys-Leu-Asp-Arg-Ile-Ser-Cys)-Asn-Arg-$NH_2$ | 22 | 1791 | B |
| H-Met-cyclo(Cys-His-Phe-Gly-Leu-Lys-Leu-Asp-Arg-Ile-Ser-Cys)-Leu-Arg-$NH_2$ | 23 | 1790 | B |
| H-Met-cyclo(Cys-His-Phe-Gly-Leu-Lys-Leu-Asp-Arg-Ile-Ser-Cys)-Leu-Arg-$NH_2$ | 24 | 1764 | B |
| H-Met-cyclo(Cys-His-Phe-Gly-Leu-Lys-Leu-Asp-Arg-Ile-Ser-Cys)-His-Arg-$NH_2$ | 25 | 1814 | C |
| H-Met-cyclo(Cys-His-Phe-Gly-Leu-Lys-Leu-Asp-Arg-Ile-Ser-Cys)-Tyr-Ser-$NH_2$ | 26 | 1771 | C |
| H-Met-cyclo(Cys-His-Phe-Gly-Leu-Lys-Leu-Asp-Arg-Ile-Ser-Cys)-Tyr-Asn-$NH_2$ | 27 | 1798 | B |
| H-Met-cyclo(Cys-His-Phe-Gly-Leu-Lys-Leu-Asp-Arg-Ile-Ser-Cys)-Tyr-His-$NH_2$ | 28 | 1821 | B |
| H-Met-cyclo(Cys-His-Pcf-Gly-Leu-Lys-Leu-Asp-Arg-Ile-Ser-Cys)-$NH_2$ | 29 | 1555 | C |
| H-Met-cyclo(Cys-His-Pff-Gly-Leu-Lys-Leu-Asp-Arg-Ile-Ser-Cys)-$NH_2$ | 30 | 1538 | C |
| H-Met-cyclo(Cys-Bal-Phe-Gly-Leu-Lys-Leu-Asp-Arg-Ile-Ser-Cys)-$NH_2$ | 31 | 1454 | B |
| H-Met-cyclo(Cys-Gab-Phe-Gly-Leu-Lys-Leu-Asp-Arg-Ile-Ser-Cys)-$NH_2$ | 32 | 1468 | C |
| H-Nle-cyclo(Cys-Gly-Phe-Gly-Leu-Lys-Leu-Asp-Arg-Ile-Ser-Cys)-$NH_2$ | 33 | 1425 | B |
| H-Met-cyclo(Cys-Gly-Phe-ala-Leu-Lys-Leu-Asp-Arg-Ile-Ser-Cys)-$NH_2$ | 34 | 1456 | B |
| H-Met-cyclo(Cys-his-Phe-ala-Leu-Lys-Leu-Asp-Arg-Ile-Ser-Cys)-$NH_2$ | 35 | 1545 | B |
| H-Met-cyclo(Cys-his-Phe-Aib-Leu-Lys-Leu-Asp-Arg-Ile-Ser-Cys)-$NH_2$ | 36 | 1549 | B |
| H-Met-cyclo(Cys-pro-Phe-Gly-Leu-Lys-Leu-Asp-Arg-Ile-Ser-Cys)-$NH_2$ | 37 | 1482 | B |
| H-Met-cyclo(Cys-ala-Phe-Gly-Leu-Lys-Leu-Asp-Arg-Ile-Ser-Cys)-$NH_2$ | 38 | 1456 | B |
| H-Met-cyclo(Cys-ser-Phe-Gly-Leu-Lys-Leu-Asp-Arg-Ile-Ser-Cys)-$NH_2$ | 39 | 1472 | B |
| H-Met-cyclo(Cys-asn-Phe-Gly-Leu-Lys-Leu-Asp-Arg-Ile-Ser-Cys)-$NH_2$ | 40 | 1499 | B |
| H-Met-cyclo(Cys-his-Phe-Gly-Leu-Pro-Leu-Asp-Arg-Ile-Ser-Cys)-$NH_2$ | 41 | 1491 | B |
| H-Met-cyclo(Cys-his-Phe-Gly-Leu-Arg-Leu-Asp-Arg-Ile-Ser-Cys)-$NH_2$ | 42 | 1550 | B |
| H-Met-cyclo(Cys-his-Phe-Gly-Leu-Lys-Leu-Asp-Arg-Tbg-Ser-Cys)-$NH_2$ | 43 | 1521 | B |
| H-Met-cyclo(Cys-thi-Phe-Gly-Leu-Lys-Leu-Asp-Arg-Ile-Ser-Cys)-$NH_2$ | 44 | 1537 | B |
| H-Met-cyclo(Cys-phe-Phe-Gly-Leu-Lys-Leu-Asp-Arg-Ile-Ser-Cys)-$NH_2$ | 45 | 1531 | C |
| H-Met-cyclo(Cys-his-Phe-Gly-Leu-Nmk-Leu-Asp-Arg-Ile-Ser-Cys)-$NH_2$ | 46 | 1535 | B |
| H-Met-cyclo(Cys-his-Phe-Gly-Leu-Lys-Nml-Asp-Arg-Ile-Ser-Cys)-$NH_2$ | 47 | 1535 | B |
| H-Met-cyclo(Cys-his-Phe-Gly-Leu-Lys-Leu-Asp-Nmr-Ile-Ser-Cys)-$NH_2$ | 48 | 1535 | B |

TABLE 3-continued

Data for agonistic activity of selected compounds according to the present invention.

| Compound | SEQ ID NO: | (M + H)+ in MS [amu] | Activity (group) |
|---|---|---|---|
| H-Met-cyclo(Cys-ala-Phe-Gly-Leu-Pro-Leu-Asp-Arg-Ile-Ser-Cys)-NH2 | 49 | 1423 | A |
| H-Met-cyclo(Cys-ala-Phe-Gly-Leu-Dab-Leu-Asp-Arg-Ile-Ser-Cys)-NH2 | 50 | 1428 | B |
| H-Met-cyclo(Cys-ala-Phe-Gly-Leu-Orn-Leu-Asp-Arg-Ile-Ser-Cys)-NH2 | 51 | 1442 | B |
| H-Met-cyclo(Cys-ala-Phe-Gly-Leu-Hly-Leu-Asp-Arg-Ile-Ser-Cys)-NH2 | 52 | 1470 | B |
| H-Met-cyclo(Cys-ala-Phe-Gly-Leu-Lys-Ile-Asp-Arg-Ile-Ser-Cys)-NH2 | 53 | 1454 | A |
| H-Met-cyclo(Cys-ala-Phe-Gly-Leu-Lys-Val-Asp-Arg-Ile-Ser-Cys)-NH2 | 54 | 1442 | B |
| H-Met-cyclo(Cys-ala-Phe-Gly-Leu-Lys-Leu-Cya-Arg-Ile-Ser-Cys)-NH2 | 55 | 1491 | B |
| H-Met-cyclo(Cys-ala-Phe-Gly-Leu-Lys-Leu-Asp-Arg-Leu-Ser-Cys)-NH2 | 56 | 1455 | B |
| H-Met-cyclo(Cys-ala-Phe-Gly-Leu-Lys-Leu-Asp-Arg-Val-Ser-Cys)-NH2 | 57 | 1441 | B |
| H-Met-cyclo(Cys-ala-Phe-Gly-Leu-Lys-Leu-Asp-Arg-Ile-Bal-Cys)-NH2 | 58 | 1439 | B |
| H-Met-cyclo(Hcy-ala-Phe-Gly-Leu-Lys-Leu-Asp-Arg-Ile-Ser-Cys)-NH2 | 59 | 1470 | B |
| H-Met-cyclo(Hcy-ala-Phe-Gly-Leu-Lys-Leu-Asp-Arg-Ile-Ser-Hcy)-NH2 | 60 | 1484 | B |
| H-Met-cyclo(Cys-ala-Phe-Gly-Leu-Lys-Leu-Asp-Arg-Ile-Ser-Cea) | 61 | 1412 | A |
| EtCO-cyclo(Cys-ala-Phe-Gly-Leu-Lys-Leu-Asp-Arg-Ile-Ser-Cys)-NH2 | 62 | 1380 | B |
| iPrCH2CO-cyclo(Cys-ala-Phe-Gly-Leu-Lys-Leu-Asp-Arg-Ile-Ser-Cys)-NH2 | 63 | 1408 | B |
| iPrEtCO-cyclo(Cys-ala-Phe-Gly-Leu-Lys-Leu-Asp-Arg-Ile-Ser-Cys)-NH2 | 64 | 1422 | A |
| Hex-cyclo(Cys-ala-Phe-Gly-Leu-Lys-Leu-Asp-Arg-Ile-Ser-Cys)-NH2 | 65 | 1422 | A |
| PhCO-cyclo(Cys-ala-Phe-Gly-Leu-Lys-Leu-Asp-Arg-Ile-Ser-Cys)-NH2 | 66 | 1428 | B |
| iPrPrCO-cyclo(Cys-ala-Phe-Gly-Leu-Lys-Leu-Asp-Arg-Ile-Ser-Cys)-NH2 | 67 | 1436 | A |
| Occ-cyclo(Cys-ala-Phe-Gly-Leu-Lys-Leu-Asp-Arg-Ile-Ser-Cys)-NH2 | 68 | 1450 | A |
| PhCH2CO-cyclo(Cys-ala-Phe-Gly-Leu-Lys-Leu-Asp-Arg-Ile-Ser-Cys)-NH2 | 69 | 1442 | B |
| PhEtCO-cyclo(Cys-ala-Phe-Gly-Leu-Lys-Leu-Asp-Arg-Ile-Ser-Cys)-NH2 | 70 | 1456 | A |
| ButSO2-cyclo(Cys-ala-Phe-Gly-Leu-Lys-Leu-Asp-Arg-Ile-Ser-Cys)-NH2 | 71 | 1444 | B |
| PhPrCO-cyclo(Cys-ala-Phe-Gly-Leu-Lys-Leu-Asp-Arg-Ile-Ser-Cys)-NH2 | 72 | 1470 | A |
| H-cyclo(Cys-ala-Phe-Gly-Leu-Lys-Leu-Asp-Arg-Ile-Ser-Cys)-NH2 | 73 | 1323 | C |
| H-Met-cyclo(Cys-ala-Phe-Gly-Leu-Amp-Leu-Asp-Arg-Ile-Ser-Cys)-NH2 | 74 | 1436 | B |
| Hex-cyclo(Cys-ala-Phe-Gly-Leu-Aze-Leu-Asp-Arg-Ile-Ser-Cys)-NH2 | 75 | 1376 | B |
| Hex-cyclo(Cys-ala-Ocf-Gly-Leu-Lys-Leu-Asp-Arg-Ile-Ser-Cys)-NH2 | 76 | 1455 | B |
| Hex-cyclo(Cys-ala-Mcf-Gly-Leu-Lys-Leu-Asp-Arg-Ile-Ser-Cys)-NH2 | 77 | 1455 | A |
| Hex-cyclo(Cys-ala-Eau-Gly-Leu-Lys-Leu-Asp-Arg-Ile-Ser-Cys)-NH2 | 78 | 1433 | B |
| Hex-cyclo(Cys-aze-Phe-Gly-Leu-Lys-Leu-Asp-Arg-Ile-Ser-Cys)-NH2 | 79 | 1433 | A |
| Hex-cyclo(Cys-thz-Phe-Gly-Leu-Lys-Leu-Asp-Arg-Ile-Ser-Cys)-NH2 | 80 | 1465 | A |
| Hex-cyclo(Cys-pip-Phe-Gly-Leu-Lys-Leu-Asp-Arg-Ile-Ser-Cys)-NH2 | 81 | 1461 | A |
| Hex-cyclo(Cys-ala-Phe-Gly-Leu-Lys-Leu-Asp-Har-Ile-Ser-Cys)-NH2 | 82 | 1436 | B |
| Hex-cyclo(Cys-ala-Phe-Gly-Leu-Lys-Nle-Asp-Arg-Ile-Ser-Cys)-NH2 | 83 | 1421 | A |
| Hex-cyclo(Cys-ala-Phe-Gly-Leu-Lys-Tbg-Asp-Arg-Ile-Ser-Cys)-NH2 | 84 | 1422 | B |
| Hex-cyclo(Cys-ala-Phe-Gly-Leu-Hpa-Leu-Asp-Arg-Ile-Ser-Cys)-NH2 | 85 | 1462 | A |
| Hex-cyclo(Cys-ala-Phe-Gly-Leu-Hpr-Leu-Asp-Arg-Ile-Ser-Cys)-NH2 | 86 | 1407 | A |
| Hex-cyclo (Cys-LA-Phe-Gly-Leu-Pro-Ile-Asp-Arg-Ile-Ser-Cys) -NH2 | 87 | 1421 | A |
| Hex-cyclo (Cys-ala-Phe-Gly-Leu-Pro-Ile-Asp-Arg-Ile-Ser-Cys) -NH2 | 88 | 1390 | A |
| Hex-cyclo (Cys-pro-Phe-Gly-Leu-Pro-Ile-Asp-Arg-Ile-Ser-Cys) -NH2 | 89 | 1416 | A |
| Hex-cyclo (Cys-pro-Phe-Gly-Leu-Lys-Leu-Asp-Arg-Ile-Ser-Cys) -NH2 | 90 | 1447 | A |
| Hex-cyclo (Cys-pro-Phe-Gly-Leu-Pro-Leu-Asp-Arg-Ile-Ser-Cys) -NH2 | 91 | 1416 | A |
| Hex-cyclo (Cys-pro-Phe-Gly-Leu-Lys-Ile-Asp-Arg-Ile-Ser-Cys) -NH2 | 92 | 1447 | A |
| Hex-cyclo (Cys-ala-Phe-Gly-Leu-Pro-Leu-Asp-Arg-Ile-Ser-Cys) -NH2 | 93 | 1390 | A |
| Hex-cyclo (Cys-ala-Phe-Gly-Leu-Lys-Chg-Asp-Arg-Ile-Ser-Cys) -NH2 | 94 | 1447 | B |
| Hex-cyclo (Cys-ala-Phe-Gly-Leu-Lys-Npg-Asp-Arg-Ile-Ser-Cys) -NH2 | 95 | 1434 | A |
| Hex-cyclo (Cys-ala-Phe-Gly-Leu-Lys-Leu-Asp-Orn-Ile-Ser-Cys) -NH2 | 96 | 1379 | B |
| Hex-cyclo (Cys-ala-Phe-Gly-Leu-Lys-Leu-Asp-Cyr-Ile-Ser-Cys) -NH2 | 97 | 1447 | B |
| Hex-cyclo (Cys-ala-Phe-Gly-Leu-Lys-Leu-Asp-Mmr-Ile-Ser-Cys) -NH2 | 98 | 1435 | B |
| Hex-cyclo (Cys-ala-Phe-Gly-Leu-Lys-Leu-Asp-Dmr-Ile-Ser-Cys) -NH2 | 99 | 1449 | B |
| Hex-cyclo (Cys-ala-Phe-Gly-Thr-Lys-Leu-Asp-Arg-Ile-Ser-Cys) -NH2 | 100 | 1408 | B |
| Hex-cyclo (Cys-ala-Phe-Gly-Ala-Lys-Leu-Asp-Arg-Ile-Ser-Cys) -NH2 | 101 | 1378 | B |
| Hex-cyclo (Cys-ala-Phe-Gly-Leu-Gly-Lys-Asp-Arg-Ile-Ser-Cys) -NH2 | 102 | 1364 | B |
| Hex-cyclo (Cys-ala-Mff-Gly-Leu-Lys-Leu-Asp-Arg-Ile-Ser-Cys) -NH2 | 103 | 1438 | B |
| Hex-cyclo (Cys-ala-Mmf-Gly-Leu-Lys-Leu-Asp-Arg-Ile-Ser-Cys) -NH2 | 104 | 1434 | A |
| Hex-cyclo (Cys-ala-Mtf-Gly-Leu-Lys-Leu-Asp-Arg-Ile-Ser-Cys) -NH2 | 105 | 1488 | C |
| Hex-cyclo (Cys-ala-Mcn-Gly-Leu-Lys-Leu-Asp-Arg-Ile-Ser-Cys) -NH2 | 106 | 1445 | B |
| Hex-cyclo (Cys-ala-Egz-Gly-Leu-Lys-Leu-Asp-Arg-Ile-Ser-Cys) -NH2 | 107 | 1465 | B |
| Hex-cyclo (Cys-ala-Mmy-Gly-Leu-Lys-Leu-Asp-Arg-Ile-Ser-Cys) -NH2 | 108 | 1450 | B |
| Hex-cyclo (Cys-ala-Phe-Gly-Leu-Lys-Leu-Asp-Bmr-Ile-Ser-Cys) -NH2 | 109 | 1449 | C |
| Hex-cyclo (Cys-ala-Phe-Gly-Leu-Lys-Leu-Asp-Arg-Eca-Ser-Cys) -NH2 | 110 | 1419 | B |
| Hex-cyclo (Cys-ala-Phe-Gly-Leu-Lys-Leu-Asp-Opy-Ile-Ser-Cys) -NH2 | 111 | 1456 | B |
| Hex-cyclo (Cys-ala-Phe-Gly-Leu-Lys-Leu-Asp-Aof-Ile-Ser-Cys) -NH2 | 112 | 1454 | C |
| Hex-cyclo (Cys-ala-Phe-Gly-Leu-Pro-Leu-Asp-Fhz-Ile-Ser-Cys) -NH2 | 113 | 1374 | B |
| Hex-cyclo (Cys-ala-Phe-Gly-Leu-Lys-Leu-Asp-Nar-Ile-Ser-Cys) -NH2 | 114 | 1408 | C |
| Hex-cyclo (Cys-ala-Phe-Gly-Leu-Lys-Leu-Asp-Arg-Ecb-Ser-Cys) -NH2 | 115 | 1434 | B |
| Hex-cyclo (Cys-ala-Phe-Gly-Leu-Lys-Leu-Asp-Arg-Atp-Ser-Cys) -NH2 | 116 | 1436 | C |
| Hex-cyclo (Cys-ala-Phe-Gly-Leu-Lys-Leu-Asp-Arg-Att-Ser-Cys) -NH2 | 117 | 1452 | C |
| Hex-cyclo (Cys-ala-Phe-Gly-Leu-Lys-Leu-Asp-Arg-Bca-Ser-Cys) -NH2 | 118 | 1448 | B |
| Hex-cyclo (Cys-ala-Phe-Gly-Leu-Lys-Leu-Asp-Arg-Chg-Ser-Cys) -NH2 | 119 | 1447 | B |
| Hex-cyclo (Cys-ala-Phe-Gly-Leu-Lys-Leu-Asp-Arg-Ile-Ser-Cea) | 120 | 1378 | A |

TABLE 3-continued

Data for agonistic activity of selected compounds according to the present invention.

| Compound | SEQ ID NO: | (M + H)+ in MS [amu] | Activity (group) |
|---|---|---|---|
| Hex-cyclo (Cys-ala-Phe-Gly-Leu-Lys-Leu-Asp-Rpy-Ile-Ser-Cys) -NH$_2$ | 121 | 1443 | B |

B. DISEASES TO BE TREATED AND/OR PREVENTED

The present invention is also directed to methods of treating or preventing diseases in a subject that involve administering to the subject a therapeutically effective amount of a composition that includes one or more NPR-B agonists as described herein, wherein the disease is one of the following. The subject may be a mammal, such as a human, a primate, a cow, a horse, a dog, a cat, a mouse, or a rat. In particular embodiments, the subject is a human.

1. Definitions

"Treatment" and "treating" refer to administration or application of a drug to a subject or performance of a procedure or modality on a subject for the purpose of obtaining a therapeutic benefit of a disease or health-related condition. The term "therapeutic benefit" used throughout this application refers to anything that promotes or enhances the well-being of the subject with respect to the medical treatment of his condition. This includes, but is not limited to, a reduction in the frequency or severity of the signs or symptoms of a disease. Therapeutic benefit also includes reducing the signs or symptoms associated with glaucoma in a subject with glaucoma. For example, a therapeutic benefit in a patient with glaucoma is obtained where there is no further progression of visual field loss in the affected eye, or a slowing of the rate of progression of visual field loss in the affected eye, or an improvement in vision.

A "disease" or "health-related condition" can be any pathological condition of a body part, an organ, or a system resulting from any cause, such as infection, trauma, genetic defect, age-related deterioration of bodily functions, and/or environmental stress. The cause may or may not be known. Examples of diseases include glaucoma, retinopathies, ocular trauma, and optic neuropathies. Thus, one of skill in the art realizes that a treatment may improve the disease condition, but may not be a complete cure for the disease.

The terms "prevention" and "preventing" are used herein according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking or minimizing the onset of a disease or health-related condition. For example, an individual with an eye that is at risk of developing glaucoma (such as an individual with ocular hypertension) can be treated with a NPR-B agonist as set forth herein for the purpose of blocking or minimizing the onset of the signs or symptoms of glaucoma (i.e., prevention of glaucoma). In a specific embodiment, prevention pertains to lowering elevated intraocular pressure, blocking detectable optic nerve damage as a result of glaucoma in a subject, reducing the rate of vision loss in a subject, or halting loss of vision in a subject. The subject can be a subject who is known or suspected of being free of a particular disease or health-related condition at the time the relevant preventive agent is administered. The subject, for example, can be a subject with no known disease or health-related condition (i.e., a healthy subject). In some embodiments, the subject had a previous disease that has been treated in the past and is now known or suspected to be disease-free.

For those skilled in the art it is easy to understand, that different diseases are summarized under certain terms or generic terms. These summaries are no limitation and each disease can be viewed on its own and can be treated or prevented with the compounds according to the present invention.

2. Glaucoma and Ocular Hypertension

Glaucoma is the second leading cause of blindness worldwide (Thylefors and Negrel 1994, *Bull World Health Organ.* 72:323-326). Open-angle glaucoma (OAG) and angle closure glaucoma combined represent the second leading cause of blindness worldwide (Quigley and Broman, 2006 *Br J Ophthalmol.* 90:262-267). Angle-closure glaucoma is more common in the Asian population (Foster et al. 2000, *Arch Ophthalmol.* 118:1105-11), while open-angle glaucoma is more commonly found in black patients (Leske et al. 2007, *Ophthalmic Epidemiol.* 14:166-172). Glaucoma is a progressive disease in which the risk of vision loss increases with disease duration. In light of an aging population worldwide, the impact of this blinding disorder can be expected to increase in the future.

The disease state referred to as glaucoma is a family of diseases characterized by a permanent loss of visual function due to irreversible damage to the optic nerve. More specifically, glaucoma results in optic neuropathy leading to the loss of retinal ganglion cell (RGC) function followed by apoptotic cell death and a progressive increase in vision loss. Morphologically or functionally distinct types of glaucoma are typically characterized by elevated intraocular pressure (TOP), which is considered to be an important risk factor of the pathological course of the disease. Disruption of normal aqueous outflow leading to elevated IOP is integral to glaucoma pathophysiology. Ocular hypertension is a condition wherein IOP is elevated but no apparent loss of visual function has occurred; such patients are considered to be at high risk for the eventual development of the visual loss associated with glaucoma. Some patients with glaucomatous field loss have relatively low IOPs. These so called normotension or low tension glaucoma patients can also benefit from agents that lower and control IOP.

Glaucoma is typically identified by changes in IOP, visual field deficits and/or fundus changes at the optic disk. Elevated IOP, found in most glaucoma patients, is a result of morphological and biochemical changes in the trabecular meshwork (TM), an aqueous humor filtering tissue located at the iris-cornea angle of the eye. As glaucoma progresses, there is a loss of TM cells and a buildup of extracellular products which inhibit the normal aqueous humor outflow resulting in IOP elevation. In addition to elevated IOP, other factors, such as genetic defects, may lead to mechanical distortion of the optic nerve head (ONH) ultimately resulting in ONH cupping and loss of RGC and their axons. The exact mechanism of this pathological process is currently unknown. It has been suggested that lowering the IOP of patients diagnosed with glaucoma by at least 20-30% will decrease the progressive worsening of the disease by 50-60% (Quigley 2005 Ophthalmology 112:1642-1643). Without proper diagnosis and treatment, glaucoma can progress to total irreversible blindness.

Initially, most open-angle glaucoma patients are managed with one or more of a wide variety of topical ocular or oral hypotensive medications that act to increase aqueous fluid outflow and/or decrease aqueous fluid production, or with surgical procedures such as laser trabeculoplasty and filtration surgery. Treatment regimens currently available for patients exhibiting elevated IOP, regardless of cause, typically include the topical application, from once daily to multiple times per day, of one or multiple eyedrops or pills containing a small molecule IOP-lowering compound. Also, pills that decrease the amount of aqueous humor created can be given between two and four times daily. Glaucoma medications typically prescribed include cholinergic agonists, adrenergic agonists, beta adrenergic blockers, carbonic anhydrase inhibitors and prostaglandin analogs. Although these classes of medications are effective in controlling IOP, each of them has certain limitations in efficacy and untoward effects. For example, beta adrenergic blockers do not lower IOP at night; many glaucoma patients do not respond to a particular drug class; and a majority of glaucoma patients require the use of a combination of drugs. In addition, many of the drugs cause local irritation of the eye, such as burning, stinging, itching, tearing, conjunctival hyperemia, foreign body sensation, blurred vision, and eye pain. Some occasionally induce systemic side effects. Hence, there is a genuine and continuous need for novel and improved glaucoma medications.

"Glaucoma" and "glaucomatous optic neuropathy" and "glaucomatous retinopathy," as used herein, are interchangeable. Glaucoma refers to a disease characterized by the permanent loss of visual function due to irreversible damage to the retinal ganglion cells in the retina and optic nerve. The major risk factor for glaucoma and the related loss of visual function is elevated intraocular pressure. There are different types of glaucoma, including primary open angle glaucoma (POAG), angle closure glaucoma, and congenital/developmental glaucoma.

As used herein, the term "intraocular pressure" or "IOP" refers to the pressure of the content inside the eye. In a normal human eye, IOP is typically in the range of 10 to 21 mm Hg. IOP varies among individuals, for example, it may become elevated due to anatomical problems, inflammation of the eye, as a side-effect from medication or due to genetic factors. "Elevated" intraocular pressure is currently considered to be >21 mm Hg, which is also considered to be a major risk factor for the development of glaucoma.

However, some individuals with an elevated IOP may not develop glaucoma and are considered to have ocular hypertension. "Ocular hypertension" as used herein refers to a condition in which the intraocular pressure in the eye of a subject is higher than normal but the optic nerve and visual fields are within normal limits. These individuals may be susceptible to developing the loss of visual function that is typically associated with glaucoma. As used herein, the terms "susceptible," or "susceptibility" refers to an individual or subject that is or at risk of developing optic nerve damage or retinal damage that is associated with elevated intraocular pressure.

Thus, the present invention is directed to methods of treating or preventing an ophthalmic disease in a subject that involve administering to the subject a therapeutically effective amount of a composition that includes one or more NPR-B agonists as described herein, wherein the ophthalmic disease is glaucoma, elevated intraocular pressure or ocular hypertension. The subject may be a mammal, such as a human, a primate, a cow, a horse, a dog, a cat, a mouse, or a rat. In particular embodiments, the subject is a human.

In preferred aspects, the NPR-B agonists of the invention will lower intraocular pressure associated with glaucoma. The glaucoma may be any type of glaucoma, such as primary open angle glaucoma, angle closure glaucoma, normal tension glaucoma, congenital glaucoma, neovascular glaucoma, steroid-induced glaucoma, or glaucoma related to ocular trauma (e.g., ghost cell glaucoma or glaucoma related to choroidal detachment).

The present invention is also directed to methods of lowering intraocular pressure in a subject, comprising administering to the subject a pharmaceutically effective amount of a composition comprising a NPR-B agonist described herein, wherein intraocular pressed is lowered. In particular embodiments, the subject is a human. For example, in specific embodiments, the human is a patient with ocular hypertension or elevated IOP.

3. CNP Deficiencies as in Diabetes

Diabetic nephropathy is a progressive kidney disease, resulting from longstanding diabetes mellitus. Experimental evidence shows that natriuretic peptides play a pathophysiological role in the glomerular abnormalities seen in diabetes mellitus. BNP overexpression prevented diabetic nephropathy in a streptozotocin-induced mouse model of diabetes (Makino et al. 2006, *Diabetologia*. 49:2514-2524). In another study with streptozotocin-induced diabetic rats, cardiac CNP mRNA concentrations were decreased 2.6-fold (Walther et al. 2000, *J Mol Endocrinol*. 24:391-395). In a genetic model of diabetes, the non-obese diabetic mouse, mesangial cells derived from diabetic mice showed constitutive overexpression of NPR-C; this was associated with a reduced response of cGMP production to ANP or CNP treatment (Ardaillou et al. 1999, *Kidney Int* 55:1293-1302).

4. Conditions with Hyperproliferation of Vascular Smooth Muscle Cells

The abnormal growth of vascular smooth muscle cells (VSMC) is a common cause of many vascular diseases. A disturbance of the balance between growth inhibitors and growth promoters results in the hyperproliferation of those cells, and vasoactive substances, including natriuretic peptides, seem to play a major role in this process. Early experimental findings indicate that the guanylyl-cyclase-linked natriuretic peptide receptors mediate anti-proliferative activity of the natriuretic peptides on vascular smooth muscle cell growth (Hutchinson et al. 1997, *Cardiovasc Res*. 35:158-167). Ex vivo experiments showed a direct inhibition of growth in rat VSMCs by CNP (Furuya et al. 1991, *Biochem Biophys Res Commun*. 177:927-931). Furthermore, migration of rat VSMCs could be inhibited by CNP (Ikeda et al. 1997, *Arterioscler Thromb Vasc Biol*. 17:731-736). CNP gene transfer resulted in a reduction of the VSMC proliferation in pig femoral arteries in vivo, and the effect was even superior over CNP peptide application (Pelisek et al. 2006, *J Gene Med*. 8:835-844). In another report, CNP gene transfer resulted in the suppression of vascular remodelling in porcine coronary arteries in vivo (Morishige et al. 2000, *J Am Coll Cardiol*. 35:1040-1047), thus further strengthening the rationale of using CNP to offset the hyperproliferation of VSMCs.

5. Cardiac Pathologies, Especially Heart Failure and Hypertrophy

Considerable evidence supports a central pathophysiological role for natriuretic peptides in cardiovascular diseases, and in particular heart failure. The advantage of focusing on CNP in this indication is the unchanged reactivity of NPR-B, while NPR-A activity was shown to be reduced in this condition (Dickey et al. 2007, *Endocrinology.* 148:3518-3522, Nakamura et al. 1994, *Circulation.* 90:1210-1214). The fact that plasma CNP is elevated in heart failure patients (Del Ry et al. 2005, *Eur J Heart Fail.* 7:1145-1148, Del Ry et al. 2007, *Peptides.* 28:1068-1073) is interpreted as part of a compensatory vasodilating response in the peripheral vasculature (Del Ry et al. 2005, *Eur J Heart Fail.* 7:1145-1148, Wright et al. 2004, *Hypertension.* 43:94-100). Traditional treatment of heart failure aims at the support of cardiac function by preventing cardiomyocyte loss and hypertrophy. CNP is able to support cardiac function via a positive effect on the vitality of cardiomyocytes (Rosenkranz et al. 2003, *Cardiovasc Res.* 57:515-522, Tokudome et al. 2004, *Endocrinology.* 145:2131-2140). Also, CNP reduced cardiac fibrosis (Horio et al. 2003, *Endocrinology.* 144:2279-2284), the effect being stronger than that by ANP or BNP. Results from studies on dogs showed a potential inotropic effect of CNP (Beaulieu et al. 1997, *Am J Physiol.* 273:H1933-1940), supporting the potential of CNP to treat heart failure.

Hypertrophy of the heart is an enlargement of the organ, due to an increase in the volume of its muscular fibres. Experimental evidence suggests that CNP exhibits important autocrine and paracrine functions within the heart and the coronary circulation (D'Souza et al. 2004, *Pharmacol Ther.* 101:113-129). In vivo administration of CNP has been shown to improve cardiac function and attenuate cardiac remodelling after myocardial infarction in rats (Soeki et al. 2005, *J Am Coll Cardiol* 45:608-616). Another recent study shows that CNP is able to reduce reactive hypertrophy of cardiomyocytes after an experimental myocardial infarction in transgenic mice over-expressing CNP in cardiomyocytes (Wang et al. 2007, *Eur J Heart Fail.* 9:548-557).

6. Cardiovascular Pathologies, Especially Atherosclerosis, Hypertension, Endothelial Dysfunction and Thrombotic Events Atherosclerosis is a chronic inflammatory response in the walls of arterial blood vessels. In vitro evidence suggests that CNP has an inhibitory role in vascular smooth muscle cell proliferation and migration (Furuya et al. 1991, *Biochem Biophys Res Commun.* 177:927-931, Shinomiya et al. 1994, *Biochem Biophys Res Commun.* 205:1051-1056). Type-C natriuretic peptide inhibited neointimal thickening in injured arteries of rabbits and rats in vivo (Furuya et al. 1995, *Ann N Y Acad Sci.* 748:517-523, Ueno et al. 1997, *Circulation.* 96:2272-2279). In an experimental model of atherosclerosis in rabbits, local infusion of CNP resulted in the preservation of endothelial function and the prevention of neointimal thickening, which normally results from endothelial injury (Gaspari et al. 2000, *Clin Exp Pharmacol Physiol.* 27:653-655).

Pulmonary hypertension is a progressive disease, characterized by an elevated pressure in the pulmonary arterial system. Common treatment is the use of vasodilatory substances. The ability of CNP to relax arteries, possibly via direct interaction with the VSMCs, has been show before in isolated pig coronary arteries (Marton et al. 2005, *Vascul Pharmacol.* 43:207-212). More specifically, CNP was able to ameliorate monocrotaline-induced pulmonary hypertension in rats and improved survival (Itoh et al. 2004, *Am J Respir Grit Care Med.* 170:1204-1211), even if treatment with CNP started 3 weeks after the onset of symptoms.

Endothelial dysfunction plays a fundamental role in the development of atherosclerosis and restenosis. In a rabbit model with features similar to those of the early stage of atherosclerosis or restenosis, chronic peri-arterial administration of ANP or CNP prevented endothelial dysfunction and development of neointima (Gaspari et al. 2000, *Clin Exp Pharmacol Physiol.* 27:653-655, Barber et al. 2005, *J Vasc Res.* 42:101-110).

Prevention of thrombotic events is critical to the management of cardiovascular diseases. The anti-thrombotic effect of CNP is well known (Ahluwalia et al. 2004, *Basic Res Cardiol.* 99:83-89). Thrombus formation was significantly suppressed in the presence of CNP in antilogous rabbit jugular vein grafts (Ohno et al. 2002, *Circulation.* 105:1623-1626). In a model of balloon-injured rabbit carotid arteries CNP was shown to exert anti-thrombotic activity, probably via an increase in the NO production by enhancing the expression of inducible NO synthase (Qian et al. 2002, *Circ Res* 91:1063-1069).

7. Stimulation of Arteriogenesis

Arteriogenesis refers to the growth of collateral arterioles into functional collateral arteries, and is linked to elevated blood pressure, and elevated flow, causing shear stress against the wall of the arterioles. The stimulation of this event presents a strategy to treat arterial occlusive diseases (van Royen et al. 2001, *Cardiovasc Res.* 49:543-553). A beneficial effect of ANP on coronary collateral blood flow has been shown earlier (Kyriakides et al. 1998, *Clin Cardiol.* 21:737-742).

8. Inflammation, Especially Reduction of Inflammatory Mediators, e.g. TNF-Alpha, Other Cytokines or any Kind of Inflammatory Mediator Several publications suggest a role of CNP in the modulation of inflammatory responses: in a model of balloon-injured rabbit carotid arteries, in vivo expression of CNP lowered the expression of the inflammatory marker ICAM-1, and reduced the infiltration of macrophages, supposedly via enhancement of NO generation (Qian et al. 2002, *Circ Res* 91:1063-1069). In another study, in rat aortic smooth muscle cells in vitro, CNP augmented the transcriptional activation of iNOS induced by inflammatory cytokines (interleukin-1 and tumour necrosis factor-$\alpha$) and hence the production of NO (Marumo et al. 1995, *Endocrinology.* 136:2135-2142). CNP infusion in rats with an acute experimental myocarditis led to a reduction of CD68-positive inflammatory cell infiltration, and lowered myocardial and serum levels of monocyte chemoattractant protein-1 (Obata et al. 2007, *Biochem Biophys Res Commun.* 356:60-66). By selectively attenuating the expression of P-selectin, CNP suppressed leukocyte rolling induced by IL-1l3 or histamine in a rapid, reversible, and concentration-dependent manner in mice (Scotland et al. 2005, *Proc Natl Acad Sci USA.* 102:14452-14457). In a model of bleomycin-induced pulmonary fibrosis in mice, infusion of CNP markedly reduced bronchoalveolar lavage fluid IL-1$\beta$ levels (Murakami et al. 2004, *Am J Physiol Lung Cell Mol Physiol.* 287:L1172-1177).

9. Pathological Leukocyte Adhesion to Endothelium and Diapedesis into Tissue In mouse mesenteric postcapillary venules in vivo in animals with high basal leukocyte activation (endothelial nitric oxide synthase knockout mice) or under acute inflammatory conditions (induced by IL-1β or histamine), CNP suppressed basal leukocyte rolling in a rapid, reversible, and concentration-dependent manner. CNP was also able to inhibit platelet-leukocyte interactions (Scotland et al. 2005, *Proc Natl Acad Sci USA*. 102:14452-14457). In a model of bleomycin-induced pulmonary fibrosis in mice, infusion of CNP for 14 days significantly inhibited infiltration of macrophages into the alveolar and interstitial regions (Murakami et al. 2004, *Am J Physiol Lung Cell Mol Physiol*. 287:L1172-1177). CNP is also known to lower the expression of cell adhesion molecules such as ICAM-1 (Qian et al. 2002, *Circ Res* 91:1063-1069), and P-Selectin (Scotland et al. 2005, *Proc Natl Acad Sci USA*. 102:14452-14457), further strengthening its role in adhesion molecule modulation.

10. Kidney Disease, Especially Renal Insufficiency, Renal Failure Due to Reduced Renal Perfusion, Glomerulonephritis and Kidney Fibrosis Local CNP production and CNP receptor expression have previously been demonstrated in glomeruli (Terada et al. 1994, *Am J Physiol*. 267:F215-222, Lohe et al. 1995, *J Am Soc Nephrol*. 6:1552-1558, Mattingly et al. 1994, *Kidney Int*. 46:744-747, Dean et al. 1994, *Am J Physiol*. 266:F491-496), in kidney cells (Zhao et al. 1994, *Kidney Int*. 46:717-725) and in mesangial cells (Suga et al. 1992, *Hypertension*. 19:762-765), suggesting a role in kidney physiology. In several conditions CNP levels in plasma or urine are altered. CNP in plasma and urine was increased in nephrotic syndrome (Cataliotti et al. 2002, *Am J Physiol Renal Physiol* 283:F464-472), CNP was increased in urine in cirrhosis with renal impairment (Gulberg et al. 2000, *Gut*. 47:852-857), renal and urine levels of CNP were increased in experimental diabetes (Shin et al. 1998, *J Endocrinol*. 158:35-42), and NP levels were elevated in chronic kidney disease, but decreased after hemodialysis or transplantation (Horl 2005, *J Investig Med* 53:366-370).

The benefit from using CNP in indications such as renal insufficiency, and renal failure, comes from its ability to relax smooth muscles in conduit arteries (Drewett et al. 1995, *J Biol Chem*. 270:4668-4674, Madhani et al. 2003, *Br J Pharmacol*. 139:1289-1296), venodilation (Chen and Burnett 1998, *J Cardiovasc Pharmacol*. 32 Suppl 3:S22-28, Wei et al. 1993, *J Clin Invest*. 92:2048-2052), and dilation of both, afferent and efferent arterioles in glomeruli, as shown in the hydronephrotic rat kidney (Endlich and Steinhausen 1997, *Kidney Int*. 52:202-207).

Glomerulopathies like glomerulonephritis are typically associated with mesangial cell proliferation, and leukocyte infiltration (Buschhausen et al. 2001, *Cardiovasc Res*. 51:463-469). The inhibitory effect of CNP on leukocyte infiltration via downregulation of ICAM-1 has been shown before (Qian et al. 2002, *Circ Res* 91:1063-1069, Buschhausen et al. 2001, *Cardiovasc Res*. 51:463-469). In addition, all NPs show anti-proliferative effects on mesangial cells in vitro on rat cells (Suganami et al. 2001, *J Am Soc Nephrol* 12:2652-2663). In vivo, CNP infusion improved immune mediated glomerulonephritis in a rat mesangioproliferative anti-Thy 1.1 model (Canaan-Kuhl et al. 1998, *Kidney Int* 53:1143-1151). In yet another study CNP inhibited glomerular mesangial cell proliferation, MCP-1 secretion, and reduced collagen IV production from mesangial cells (Osawa et al. 2000, *Nephron*. 86:467-472).

The inhibitory effect of CNP on the proliferation of glomerular mesangial cells (Suganami et al. 2001, *J Am Soc Nephrol* 12:2652-2663, Canaan-Kuhl et al. 1998, *Kidney Int* 53:1143-1151, Osawa et al. 2000, *Nephron*. 86:467-472) suggests its use in the treatment of kidney fibrosis.

11. Liver Diseases, Especially Portal Vein Hypertension, Liver Cirrhosis, Liver Ascites, Liver Fibrosis and Hepatorenal Syndrome Evidence for a local natriuretic peptide system in the human liver comes from mRNA analysis; specific transcripts for all three NPRs, namely NPR-A, B, and C, could be detected, along with mRNA for ANP and CNP, but not BNP (Vollmar et al. 1997, *Gut*. 40:145-150). During chronic liver diseases, hepatic stellate cells, believed to play a role in the pathogenesis of liver fibrosis and portal hypertension (Friedman 1993, *N Engl J Med*. 328:1828-1835), acquire a myofibroblastic phenotype, proliferate, and synthetize components associated with fibrosis. Activation of NPR-B by CNP in myofibroblastic hepatic stellate cells was shown to inhibit both growth and contraction (Tao et al. 1999, *J Biol Chem*. 274:23761-23769), suggesting that during chronic liver diseases, CNP may counteract both liver fibrogenesis and associated portal hypertension.

Liver cirrhosis is the result of a chronic liver disease characterized by replacement of liver tissue by fibrous scar tissue. The presence of CNP in the human kidney and urine (Mattingly et al. 1994, *Kidney Int*. 46:744-747) suggests a role for CNP in fluid and electrolyte homeostasis, and thus possibly a role in renal function disturbances in patients with cirrhosis of the liver. CNP in the urine of cirrhotic patients with impaired renal function was increased, while plasma levels were normal (Gulberg et al. 2000, *Gut*. 47:852-857). In cirrhotic patients, ANP infusion reduced the portal pressure and increased the hepatic blood flow, indicative of a lowering of intra-hepatic resistance to portal flow (Brenard et al. 1992, *J Hepatol*. 14:347-356). Administration of pharmacological doses of CNP to cirrhotic rats significantly decreased portal pressure and peripheral vascular resistance, and increased cardiac output (Komeichi et al. 1995, *J Hepatol*. 22:319-325).

Many disorders can cause ascites, but cirrhosis is the most common Hence, treatment of disorders such as liver cirrhosis will eventually help in the avoidance of ascites.

According to the vasodilation theory, the hepatorenal syndrome is the result of the effect of vasoconstrictor systems acting on the renal circulation. Due to this increased activity of the vasoconstrictor systems, renal perfusion and glomerular filtration rate are markedly reduced, while tubular function is preserved. Any substance that increases renal perfusion and/or glomerular filtration rate is thus suited to be used against the hepatorenal syndrome.

12. Lung Diseases, Especially Pulmonary Hypertension, Asthma and Pulmonary Fibrosis CNP was shown to be locally synthesized in pulmonary tissues and therefore might have action on airway patency (Suga et al. 1992, *Circ Res*. 71:34-39). In vitro CNP was one order of magnitude more potent than ANP in cGMP production in cultured aortic smooth muscle cells.

Pulmonary hypertension is a progressive disease, characterized by an elevated pressure in the pulmonary arterial system. Common treatment is the use of vasodilatory substances. The ability to relax arteries, probably via direct interaction with the VSMCs, has been shown before in isolated pig coronary arteries (Marton et al. 2005, *Vascul Pharmacol.* 43:207-212). More specifically, CNP was able to ameliorate monocrotaline-induced pulmonary hypertension in rats and to improve survival (Itoh et al. 2004, *Am J Respir Crit Care Med.* 170:1204-1211), even if treatment with CNP started 3 weeks after the onset of symptoms.

In an ovalbumin-induced asthmatic guinea pig model CNP was able to significantly inhibit the bronchoconstriction and microvascular leakage in a dose-dependent manner (Ohbayashi et al. 1998, *Eur J Pharmacol.* 346:55-64). In vivo in asthmatics Fluge et al. could demonstrate dose-dependent bronchodilating properties of intravenous natriuretic peptide (Fluge et al. 1995, *Regul Pept.* 59:357-370).

In a model of bleomycin-induced pulmonary fibrosis in mice, infusion of CNP markedly attenuated the fibrosis, as indicated by significant decreases in Ashcroft score and lung hydroxyproline content (Murakami et al. 2004, *Am J Physiol Lung Cell Mol Physiol.* 287:L1172-1177) Immunohistochemistry on lung sections revealed a significantly reduced infiltration of macrophages into the alveolar and interstitial regions. The markedly decreased number of Ki-67-positive cells in fibrotic lesions of the lung further supports the notion of CNP's anti-proliferative effects on pulmonary fibrosis.

13. Male and Female Fertility Problems, Especially Erectile Dysfunction, Stimulation of Male Fertility and Stimulation of Female Fertility Penile erection depends on relaxation of the smooth muscle of the corpus cavernosum, one of the sponge-like regions of erectile tissue. The presence of NPR-B in rat and rabbit cavernosal membrane was shown by Kim et al. (Kim et al. 1998, *J Urol.* 159:1741-1746). They also showed that CNP could trigger the production of cGMP in this tissue, and that CNP was much more potent than BNP and ANP in doing so. NPR-B was also shown to be located in the human corpus cavernosum penis; in organ bath studies with corpus cavernosum muscle strips CNP at concentrations of 0.1 nM to 1 µM led to smooth muscle relaxation from 5% to 40% (Kuthe et al. 2003, *J Urol.* 169:1918-1922); further support for a role of CNP in erectile dysfunction comes from a recent study, showing that CNP levels are associated with the presence, severity, and duration of erectile dysfunction (Vlachopoulos et al. 2008, *Eur Urol.* in press).

The rationale for using CNP to stimulate male fertility is based on its potential function in testicular blood supply, the modulation of germ cell development and spermatozoan motility, and its role in penile erection (as described above). CNP has been found in seminal plasma of several species (Hosang and Scheit 1994, *DNA Cell Biol.* 13:409-417, Chrisman et al. 1993, *J Biol Chem.* 268:3698-3703); human Leydig cells, located adjacent to the seminiferous tubules in the testicle, contain both, CNP and the NPR-B receptor (Middendorff et al. 1996, *J Clin Endocrinol Metab.* 81:4324-4328). CNP was able to increase testosterone levels in vitro in purified mouse Leydig cells (Khurana and Pandey 1993, *Endocrinology.* 133:2141-2149), as well as in vivo in the spermatic vein in men (Foresta et al. 1991, *J Clin Endocrinol Metab.* 72:392-395). Because testosterone activates the initiation, processing and maintenance of spermatogenesis, CNP has thus an immediate influence on spermatogenesis. Local injection of natriuretic peptides in vivo in rats caused a dose-related increase in testicular blood flow (Collin et al. 1997, *Int J Andra* 20:55-60).

A function of CNP in fertilization, pregnancy and embryonic development was first proposed after the detection of CNP in porcine seminal plasma (Chrisman et al. 1993, *J Biol Chem.* 268:3698-3703). Further studies showed expression of NPR-A and -B receptors in human placenta (Itoh et al. 1994, *Biochem Biophys Res Commun.* 203:602-607), and their modulation in rat ovary and uterus by the estrous cycle (Huang et al. 1996, *Am J Physiol.* 271:H1565-1575, Dos Reis et al. 1995, *Endocrinology.* 136:4247-4253, Noubani et al. 2000, *Endocrinology.* 141:551-559). In mice, uterine CNP mRNA concentrations increased during pregnancy, whereas in the ovaries these levels decreased compared to non-pregnant controls (Stepan et al. 2001, *Regul Pept.* 102:9-13). In human placenta and myometrium CNP is expressed with no dependency on gestational age in the third trimester. Pregnancies with intra-uterine growth retardation showed an opposite regulation of CNP in placenta and myometrium, indicating an organ-specific function of the peptide in human reproductive tissue (Stepan et al. 2002, *Fetal Diagn Ther.* 17:37-41). This could be substantiated by studying NPR-B knock-out mice; female mice were infertile due to the failure of the female reproductive tract to develop (Tamura et al. 2004, *Proc Natl Acad Sci USA.* 101:17300-17305).

14. Pre-Eclampsia and/or Preterm Labor

Pre-eclampsia, a hypertensive disorder of pregnancy, is usually associated with raised blood pressure, and affects about 2-8% of pregnancies. Inadequate blood supply to the placenta leads to endothelial dysfunction, eventually resulting in damage to the maternal endothelium and kidney and liver. In severe pre-eclampsia BNP levels are elevated, which might reflect ventricular stress and/or subclinical cardiac dysfunction associated with the condition (Resnik et al. 2005, *Am J Obstet Gynecol.* 193:450-454). Pregnancies with intra-uterine growth retardation or pre-eclampsia showed an opposite regulation of CNP, with a decrease in the placenta and an increase in the myometrium compared with normal pregnancies (Stepan et al. 2002, *Fetal Diagn Ther.* 17:37-41), while maternal CNP plasma levels remained constant; this could indicate a compensatory or causative organ-specific function of the peptide in human reproductive tissue under these pathophysiological conditions, suggesting that application of CNP may have benefits.

15. Skeletal Growth Disturbances, Especially Decreased Body Height (Dwarfism)

Dwarfism can be caused by over 200 separate medical conditions. C-type natriuretic peptide, acting through its receptor, NPR-B, plays a critical role in longitudinal bone growth (Olney 2006, *Growth Horm IGF Res.* 16 Suppl A:S6-14), as it stimulates endochondrial ossification (Tamura et al. 2004, *Proc Natl Acad Sci USA.* 101:17300-17305, Miyazawa et al. 2002, *Endocrinology.* 143:3604-3610). A spontaneous autosomal recessive point mutation in the CNP gene, called long bone abnormality (lbab), causes severe dwarfism in mice (Yoder et al. 2008, *Peptides.* 29:1575-1581, Tsuji et al. 2008, *Biochem Biophys Res Commun.* 376:186-190). Complete absence of CNP in mice resulted in dwarfism and early death (Chusho et al. 2001, *Proc Natl Acad Sci USA.* 98:4016-4021).

16. Defects of FGF-R (Fibroblast Derived Growth Factor Receptor) Signalling, Especially Overactivity of FGF-R, or Deficiency of CNP or Osteocrin, or Reduced Level of CNP or Osteocrin in the Growth Plates of Long Bones In vitro and ex vivo studies showed that CNP acts within the growth plate. CNP, most likely synthetised by proliferating chondrocytes (Chusho et al. 2001, *Proc Natl Acad Sci USA*. 98:4016-4021), acts locally to stimulate further proliferation. As opposing element, the FGF/FGFR-3 pathway is known to negatively regulate endochondral ossification via activation of the Erk MAP kinase pathway, thus inhibiting chondrocyte proliferation and cartilage matrix production (Krejci et al. 2005, *J Cell Sci*. 118:5089-5100). The targeted overexpression of CNP in chondrocytes offset dwarfism in a mouse model of achondroplasia with activated fibroblast growth factor receptor 3 in the cartilage, suggesting a direct interaction of their signaling pathways (Yasoda et al. 2004, *Nat Med*. 10:80-86). Moreover, Ozasa et al. found that CNP was able to antagonize the activation of the MAPK cascade by FGFs, making the CNP/NPR-B pathway attractive as a novel therapeutic target in the treatment of achondroplasia (Ozasa et al. 2005, Bone. 36:1056-1064). CNP also partially antagonized the FGF2-induced expression, release and activation of several matrix-remodeling molecules including several matrix metalloproteinases. Independent of FGF signaling, CNP stimulated the upregulation of matrix production (Krejci et al. 2005, *J Cell Sci*. 118:5089-5100).

Osteocrin is a specific ligand of the natriuretic peptide clearance receptor NPR-C that modulates bone growth (Thomas et al. 2003, *J Biol Chem*. 278:50563-50571). By blocking the clearance function of NPR-C, it causes the local elevation of CNP levels, resulting in the proliferation of chondrocytes (Moffatt et al. 2007, *J Biol Chem*. 282:36454-36462).

In summary, there is a strong rationale to use CNP in order to compensate for overactive FGF receptors, and for deficiencies or reduced levels of CNP or osteocrin.

17. Arthritis, Especially Degenerative Diseases of Cartilage Tissue, Osteoarthritis and Cartilage Degeneration and Arthritis in Response to Traumatic Cartilage Injury The rationale for the use of natriuretic peptides for the treatment and/or prevention of arthritic diseases comes from the observation that CNP is involved in the skeletal growth, especially in the generation of cartilage extracellular matrix (Chusho et al. 2001, *Proc Natl Acad Sci USA*. 98:4016-4021, Yasoda et al. 2004, *Nat Med*. 10:80-86), which is able to stabilize damaged cartilage.

CNP depletion was shown to result in impaired bone growth, like that observed in achondroplastic bones, with a similar histological picture of decreased width in both the proliferative and hypertrophic chondrocyte layers of the growth plate (Chusho et al. 2001, *Proc Natl Acad Sci USA*. 98:4016-4021). The targeted overexpression of CNP in chondrocytes counteracted dwarfism in a mouse model of achondroplasia with activated fibroblast growth factor receptor 3 in the cartilage. CNP corrected the decreased extracellular matrix synthesis in the growth plate through inhibition of the MAPK pathway of FGF signaling, resulting in the stimulation of glucosaminoglycans and cartilage collagen (type II) synthesis (Yasoda et al. 2004, *Nat Med*. 10:80-86).

In rat chondrosarcoma chondrocytes, after FGF2-mediated growth arrest, CNP mediated the inhibition of MMP induction, and stimulated extracellular matrix synthesis (Krejci et al. 2005, *J Cell Sci*. 118:5089-5100, Ozasa et al. 2005, Bone. 36:1056-1064), both effects resulting in a net increase in cartilage extracellular matrix (Krejci et al. 2005, *J Cell Sci*. 118:5089-5100).

18. Tissue Engineering and Cartilage Regeneration, Especially for the Ex Vivo Expansion of Cartilage Cells to a Cell Number Sufficient to Transplant Cells Back into a Patient CNP has stimulatory activity on glucosaminoglycan and cartilage collagen (type II) synthesis in chondrocytes (Krejci et al. 2005, *J Cell Sci*. 118:5089-5100, Yasoda et al. 2004, *Nat Med*. 10:80-86), a feature that is beneficial for in vivo regeneration of cartilage. To produce ex vivo tissue from the limited number of cells that can be extracted from an individual for therapeutic purposes, it is also necessary to have a stimulation of cell proliferation. In a key publication, Waldman et al. reported, that in high-density 3D cultures low doses of CNP (10 to 100 pM) elicited chondrocyte proliferation of up to 43% increase in cellularity at the highest dose. Higher doses of CNP (10 nM) predominantly stimulated matrix deposition without affecting tissue cellularity (Waldman et al. 2008, *Tissue Eng Part A*. 14:441-448). CNP is thus suitable as a modulator of both chondrocyte proliferation and ECM deposition during in vitro cartilage growth.

19. Tissue Engineering and Bone Regeneration, Especially for the Acceleration of Bone Healing or for the Improvement of Regenerating Bone Tissue The role of the NPR-B/CNP system as an important regulator of bone growth has been established by several publications: NPR-B knock-out mice displayed reduced bone growth (Tamura et al. 2004, *Proc Natl Acad Sci USA*. 101:17300-17305, Pfeifer et al. 1996, Science. 274:2082-2086); mice with a deletion of the CNP gene also showed reduced bone growth, and this phenotype could be rescued by the overexpression of CNP in chondrocytes (Chusho et al. 2001, *Proc Natl Acad Sci USA*. 98:4016-4021); overexpression of BNP in mice resulted in skeletal overgrowth (Suda et al. 1998, *Proc Natl Acad Sci USA*. 95:2337-2342). More specifically, CNP was able to promote chondrocyte proliferation and matrix formation (Krejci et al. 2005, *J Cell Sci*. 118:5089-5100, Ozasa et al. 2005, Bone. 36:1056-1064). Using an organ culture of fetal mouse tibias, an in vitro model of endochondral ossification, longitudinal bone growth was stimulated by CNP (Yasoda et al. 1998, *J Biol Chem*. 273:11695-11700).

In summary, the experimental evidence strongly supports the use of CNP in bone regenerating applications.

20. Modulation of Neuronal Activity, Especially for Replacement of CNP in its "Central Nervous Function"

The extensive distribution of the NPR-C receptor in the brainstem suggests an involvement of NPR-C in the neuromodulatory effect of natriuretic peptides (Abdelalim et al. 2008, Neuroscience. 155:192-202), which were shown to evoke a variety of peripheral effects when applied to the brain (Puurunen and Ruskoaho 1987, *Eur J Pharmacol*. 141:493-495, Bianciotti et al. 2001, Regul Pept. 102:127-133). Intra-cerebroventricular administration of atrial natriuretic peptide in anaesthetized rats, for example, resulted in the stimulation of gastric acid secretion, that was totally abolished by vagotomy, suggesting vagus nerve involvement (Puurunen and Ruskoaho 1987, *Eur J Pharmacol*. 141:493-495). In two studies by Sabbatini et al., the cerebroventricular administration of CNP in rats dose-dependently enhanced the exocrine pancreatic fluid output through the activation of the NPR-C receptor and the vago-vagal reflex (Sabbatini et al. 2005, *Eur J Pharmacol.* 524:67-74, Sabbatini et al. 2007, *Eur J Pharmacol.* 577:192-202), thus mimicking the effect of endogenous CNP.

21. Cancer, Through Inhibition of Proliferation of Tumor Cells, Especially Glioma Cells, Neuroblastoma Cells, Adenocarcinoma Cells, Adenocarcinoma Cells in Breast Pancreas and Prostate, Melanoma Cells and Renal Carcinoma Cells Several publications have shown the presence of natriuretic peptide receptors on tumor cells, suggesting a potential to affect the proliferation of those cells via application of CNP, as has been shown in a range of other cell types.

Early in vitro data from cultered rat glioma cells demonstrated the presence of receptors on those cells, that showed strongest activation by CNP, i.e. cGMP production (Eguchi et al. 1992, *Eur J Pharmacol.* 225:79-82). In another cell line, a AtT-20 pituitary tumor cell line, the only natriuretic receptor present on the cell surface was the NPR-B receptor. cGMP production in these AtT-20 cells was stimulated up to 200-fold by CNP (Gilkes et al. 1994, *Biochem J.* 299 (Pt 2):481-487).

Western immunoblotting identified NPR-A and -C receptors in human colon adenocarcinoma cells. Application of 1 mM ANP to these cells resulted in a decrease of up to 97% in cell number within 24 h, suggesting an anti-proliferative activity (Gower et al. 2005, *Int J Gastrointest Cancer.* 36:77-87).

CNP caused a 39% decrease in the number of small-cell lung cancer cells at 100 nM. The mechanism of growth inhibition supposedly is based on the inhibition of DNA synthesis, mediated in part by cGMP (Vesely et al. 2005, *Eur J Clin Invest.* 35:388-398).

In yet another cell type, in human renal carcinoma cells, CNP also decreased the cell number, at a concentration of 100 μM by 10%. This effect was sustained without any proliferation of the cells occurring for three days after treatment with CNP. All three types of natriuretic peptide receptors, NPR-A, -B, and -C, were identified on renal cancer cells (Vesely et al. 2006, *Eur J Clin Invest.* 36:810-819).

22. Fibrosis, Especially Pulmonary Fibrosis, Renal Fibrosis, Cardiac Fibrosis, Hepatic Fibrosis or Systemic Fibrosis/Sclerosis Several studies, investigating fibrotic events in different organ systems, have shown that the application of natriuretic peptides, in particular of CNP, has a beneficial effect on disease progression. A more general effect of CNP-mediated cGMP generation in fibroblasts is the block of the activation of the mitogen-activated protein kinase cascade (Chrisman and Garbers 1999, *J Biol Chem.* 274:4293-4299), which could be exploited to treat any kind of fibrosis, in particular the multiorgan systemic fibrosis/sclerosis; treatment of single organ fibrosis with CNP is supported by the following data:

In a model of bleomycin-induced pulmonary fibrosis in mice, infusion of CNP markedly reduced bronchoalveolar lavage fluid levels of inflammatory IL-1β, inhibited infiltration of macrophages into the alveolar and interstitial regions, and markedly attenuated the fibrosis, as indicated by significant decreases in Ashcroft score and lung hydroxyproline content (Murakami et al. 2004, *Am J Physiol Lung Cell Mol Physiol.* 287:L1172-1177).

With regard to kidney fibrosis, it was described that CNP had an inhibitory effect on the proliferation of glomerular mesangial cells (Suganami et al. 2001, *J Am Soc Nephrol* 12:2652-2663, Canaan-Kuhl et al. 1998, *Kidney Int* 53:1143-1151, Osawa et al. 2000, *Nephron.* 86:467-472). In particular, CNP inhibited also MCP-1 secretion, and reduced collagen IV production from glomerular mesangial cells (Osawa et al. 2000, *Nephron.* 86:467-472).

Cardiac fibrosis, characterized by the proliferation of interstitial fibroblasts and the biosynthesis of extracellular matrix components in the ventricles of the heart, is a consequence of remodeling processes. Soeki et al. showed that the application of CNP improved cardiac function and protected against cardiac remodeling after myocardial infarct in rats (Soeki et al. 2005, *J Am Coll Cardiol* 45:608-616). In vitro, in cardiac fibroblasts, CNP had a suppressive effect on fibroblast proliferation and extracellular matrix production, the effect being stronger than by ANP or BNP (Horio et al. 2003, *Endocrinology.* 144:2279-2284).

During chronic liver diseases, hepatic stellate cells, believed to play a role in the pathogenesis of liver fibrosis and portal hypertension (Friedman 1993, *N Engl J Med.* 328:1828-1835), acquired a myofibroblastic phenotype, proliferated, and synthesized components associated with fibrosis. The activation of NPR-B by CNP in myofibroblastic hepatic stellate cells was shown to inhibit both growth and contraction (Tao et al. 1999, *J Biol Chem.* 274:23761-23769), suggesting that during chronic liver diseases, CNP may counteract fibrogenesis.

C. PHARMACEUTICAL PREPARATIONS

Other embodiments of the present invention are directed to pharmaceutical compositions, comprising at least one novel NPR-B agonist described herein, directed to the treatment or prevention of a disease in a subject that is associated with elevated TOP, glaucoma, ocular hypertension, and/or retinal ganglion cell loss.

1. Effective Amount

As used herein, the term "effective amount," or "therapeutically effective amount," refers to an amount of the agent that will activate the function and/or activity of a type B natriuretic peptide receptor. The novel NPR-B agonists described herein lower intraocular pressure or treat ocular hypertension in a patient having elevated TOP or ocular hypertension. Thus, an effective amount is an amount sufficient to detectably and repeatedly ameliorate, reduce, minimize or limit the extent of any disease associated with elevated intraocular pressure or ocular hypertension, such as any of those diseases discussed above.

Treatment and/or prevention methods will involve treating an individual with an effective amount of a composition containing a therapeutically effective amount of at least one NPR-B agonist of the invention. A therapeutically effective amount is described, generally, as that amount that is known to be or suspected to be of benefit in the reduction of the signs or symptoms of a disease. In some embodiments of the present invention, an effective amount is generally an amount that is known or suspected to be of benefit in reducing the signs or symptoms of glaucoma and associated optic nerve or retinal damage in a subject. It is envisioned that the treatment with the NPR-B agonists hereof will stabilize or improve visual function (as measured by visual acuity, visual field, or other method known to those of ordinary skill in the art).

In some embodiments, an effective amount of a NPR-B agonist that may be administered to a subject includes a dose from about 1 microgram/kg/body weight to about 500 microgram/kg/body weight or more per administration, and any range derivable therein.

2. Formulations

Regarding the methods set forth herein, a NPR-B agonist can be formulated in any manner known to those of ordinary skill in the art. In the compositions set forth herein, the concentration of a NPR-B agonist can be any concentration known or suspected by those of ordinary skill in the art to be of benefit in the treatment and/or prevention of ophthalmic disease associated with elevated intraocular pressure or ocular hypertension.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain non-limiting embodiments, the ophthalmic pharmaceutical compositions may comprise, for example, at least about 0.1%, by weight or volume, of an active ingredient. In other embodiments, the active ingredient may comprise between about 0.001% to about 75% of the weight or volume of the unit, or between about 0.01% to about 60%, and any range derivable therein. In more particular embodiments, the pharmaceutical composition may comprise between about 0.03% to about 2.0% by weight or volume, of an active ingredient. In more particular embodiments, the composition comprises between about 0.05% to about 1.5% by weight or volume of an active ingredient. In further embodiments, the composition comprises between about 0.05% to about 1.2% by weight or volume of an active ingredient.

A dose may be any amount of pharmaceutical composition that is known or suspected to be of therapeutic benefit. For example, a dose may be about 1 microgram/kg/body weight to about 500 microgram/kg/body weight or more per administration, and any range derivable therein. A dose may be repeated as necessary as determined by one of ordinary skill in the art to achieve a desired therapeutic effect. For example, a dose may be repeated once, twice, three times, and so forth. In some embodiments, a dose is administered twice a day, three times a day, four times a day, or more often. In further embodiments, a dose is administered every other day, twice a week, once a month, or at a longer interval.

In certain embodiments of the present invention, the compositions set forth herein can include more than one NPR-B agonist. One of ordinary skill in the art would be familiar with preparing and administering pharmaceutical compositions that include more than one therapeutic agent. In some embodiments, the composition includes one or more additional therapeutic agents that are not NPR-B agonists.

In addition to the NPR-B agonists, the compositions of the present invention optionally comprise one or more excipients. Excipients commonly used in pharmaceutical compositions include, but are not limited to, carriers, tonicity agents, preservatives, chelating agents, buffering agents, surfactants and antioxidants.

A person of ordinary skill will recognize that the compositions of the present invention can include any number of combinations of ingredients (e.g., active agent, polymers, excipients, etc.). It is also contemplated that that the concentrations of these ingredients can vary. In non-limiting aspects, the percentage of each ingredient in the composition can be calculated by weight or volume of the total composition. A person of ordinary skill in the art would understand that the concentrations can vary depending on the addition, substitution, and/or subtraction of ingredients in a given composition.

In some embodiments of the invention, a specific amount of a NPR-B agonist is administered via the compositions described herein.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient.

Any of a variety of carriers may be used in the formulations of the present invention including water, mixtures of water and water-miscible solvents, such as $C_{1-7}$-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, mixtures of those polymers. The concentration of the carrier is, typically, from 1 to 100000 times the concentration of the active ingredient.

Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present invention optionally comprise an additional active agent.

In particular embodiments, the compositions are suitable for application to mammalian eyes. For example, for ophthalmic administration, the formulation may be a solution, a suspension, a gel, or an ointment.

In preferred aspects, the compositions that include NPR-B agonists will be formulated for topical application to the eye in aqueous solution in the form of drops. The term "aqueous" typically denotes an aqueous composition wherein the carrier is to an extent of >50%, more preferably >75% and in particular >90% by weight water.

These drops may be delivered from a single dose ampoule which may preferably be sterile and thus rendering bacteriostatic or bacteriocidal components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

The compositions of the present invention may also be formulated as solutions that undergo a phase transition to a gel upon administration to the eye.

In addition to the one or more NPR-B agonists, the compositions of the present invention may contain other ingredients as excipients. For example, the compositions may include one or more pharmaceutically acceptable buffering agents, preservatives (including preservative adjuncts), non-ionic tonicity-adjusting agents, surfactants, solubilizing agents, stabilizing agents, comfort-enhancing agents, polymers, emollients, pH-adjusting agents and/or lubricants.

For topical formulations to the eye, the formulations are preferably isotonic, or slightly hypotonic in order to combat any hypertonicity of tears caused by evaporation and/or disease. The compositions of the present invention generally have an osmolality in the range of 220-320 mOsm/kg, and preferably have an osmolality in the range of 235-260 mOsm/kg. The compositions of the invention have a pH in the range of 5-9, preferably 6.5-7.5, and most preferably 6.9-7.4.

The formulations set forth herein may comprise one or more preservatives. Examples of preservatives include quaternary ammonium compounds, such as benzalkonium chloride or benzoxonium chloride. Other examples of preservatives include alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, or sorbic acid.

In certain embodiments, the NPR-B agonists are formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. The formulation of the present invention may be used with contact lenses or other ophthalmic products.

In some embodiments, the compositions set forth herein have a viscosity of 0.5-10 cps, preferably 0.5-5 cps, and most preferably 1-2 cps. This relatively low viscosity insures that the product is comfortable, does not cause blurring, and is easily processed during manufacturing, transfer and filling operations.

3. Route of Administration

Administration of the compositions of the invention can be by any method known to those of ordinary skill in the art, however, local administration is preferred. It is contemplated that all local routes to the eye may be used including topical, subconjunctival, periocular, retrobulbar, subtenon, intracameral, intravitreal, intraocular, subretinal, juxtascleral and suprachoroidal administration. Systemic or parenteral administration may be feasible including but not limited to intravenous, subcutaneous, intramuscular and oral delivery. The most preferred method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel formulation.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

D. SECONDARY FORMS OF THERAPY

In certain embodiments of the present invention, the subject is receiving one or more secondary forms of therapy directed to treatment or prevention of a particular eye disease.

A NPR-B agonist-containing ophthalmic composition of the present invention may be administered along with another agent or therapeutic method. For example, administration of the NPR-B agonist-containing composition of the present invention to a human subject may precede, follow, or be concurrent with other therapies for glaucoma, elevated intraocular pressure or ocular hypertension. In some embodiments, the NPR-B agonist is formulated in the same composition as the secondary form of therapy. In other embodiments, the NPR-B agonist is formulated separately from the secondary form of therapy. One of ordinary skill in the art would be familiar with protocols for administering more than one form of pharmacological therapy to a subject with a disease, and would be familiar with methods of formulating more than one pharmacological agent in the same composition.

Examples of secondary therapeutic agents include, but are not limited to: anti-glaucoma agents, such as beta-blockers including timolol, betaxolol, levobetaxolol, carteolol, miotics including pilocarpine, carbonic anhydrase inhibitors, prostaglandins, seretonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as nerve growth factor (NGF), basic fibroblast growth factor (bFGF), brain-derived neurotrophic factor (BDNF), ciliary neutrophic factor (CNTF); immunosuppressant agents; and anti-allergic agents including olopatadine. Information pertaining to olopatadine formulations can be found in U.S. Pat. No. 6,995,186, U.S. Patent App. Pub. No. 2005/0158387, and U.S. Patent App. Pub. No. 2003/0055102, each of which is hereby specifically incorporated by reference. The ophthalmic drug may be present in the form of a pharmaceutically acceptable salt, such as timolol maleate, brimonidine tartrate or sodium diclofenac.

Other examples of a secondary therapeutic agent include a receptor tyrosine kinase (RTK) inhibitor. Exemplary RTK inhibitors are described in U.S. Patent App. Pub. No. 20060189608, and U.S. Pat. No. 7,297,709, both of which are hereby specifically incorporated by reference. In preferred embodiments, the receptor tyrosine kinase inhibitor is N-[4-[3-amino-1H-indazol-4-yl]phenyl]-N'-(2-fluoro-5-methylphenyl)urea.

In other particular embodiments, the secondary therapeutic agent is a prostaglandin or a prostaglandin analog. For example, the prostaglandin analog may be latanoprost, bimatoprost, unoprostone or travoprost.

In particular embodiments, the secondary therapeutic agent is a steroid. For example, the steroid may be a glucocorticoid, a progestin, a mineralocorticoid, or a corticosteroid. Exemplary corticosteroids include cortisone, hydrocortisone, prednisone, prednisolone, methylprednisone, triamcinolone, fluoromethalone, dexamethasone, medrysone, betamethasone, loteprednol, fluocinolone, flumethasone, or mometasone. Other examples of steroids include androgens, such as testosterone, methyltestosterone, or danazol. The secondary therapeutic agent may also be a glucocorticoid that is devoid of typical glucocorticoid side-effects, such as a cortisene. Preferred cortisenes for use in the methods of the invention include anecortave acetate and anecortave desacetate. Often steroids are administered as ester, acetal, or ketal prodrugs, many of which are water-insoluble. The secondary therapeutic agents may be directed to treatment or prevention of a single disease, or can be directed to treatment or prevention of two or more diseases.

In addition to pharmacological agents, surgical procedures can be performed in combination with the administration of the NPR-B agonists. One such surgical procedure can include laser trabeculoplasty or trabeculectomy. In laser trabeculoplasty, energy from a laser is applied to a number of noncontiguous spots in the trabecular meshwork. It is believed that the laser energy stimulates the metabolism of the trabecular cells, and changes the extracellular material in the trabecular meshwork.

Another surgical procedure may include filtering surgery. With filtering surgery, a hole is made in the sclera near the angle. This hole allows the aqueous fluid to leave the eye through an alternate route. The most commonly performed filtering procedure is a trabeculectomy. In a trabeculectomy, a conjunctiva incision is made, the conjunctiva being the transparent tissue that covers the sclera. The conjunctiva is moved aside, exposing the sclera at the limbus. A partial thickness scleral flap is made and dissected half-thickness into the cornea. The anterior chamber is entered beneath the scleral flap and a section of deep sclera and/or trabecular meshwork is excised. The scleral flap is loosely sewn back into place. The conjunctival incision is tightly closed. Postoperatively, the aqueous fluid passes through the hole, beneath the scleral flap which offers some resistance and collects in an elevated space beneath the conjunctiva called a bleb. The fluid then is either absorbed through blood vessels in the conjunctiva or traverses across the conjunctiva into the tear film.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

The materials and methods as well as general methods are further illustrated by the following examples:

Solvents:

Solvents were used in the specified quality without further purification.

Acetonitrile (Gradient grade, J.T. Baker); dichloromethane (for synthesis, VWR); diethylether (for synthesis, VWR); N,N-dimethylformamide (LAB, VWR); dioxane (for synthesis, Aldrich); methanol (for synthesis, VWR).

Water: Milli-Q Plus, Millipore, demineralized.

Reagents:

The used reagents were purchased from Advanced ChemTech (Bamberg, Germany), Sigma-Aldrich-Fluka (Deisenhofen, Germany), Bachem (Heidelberg, Germany), J.T. Baker (Phillipsburg, USA), Iris Biotech (Marktredwitz, Germany), Lancaster (Griesheim, Germany), VWR (Darmstadt, Germany), NeoMPS (Strasbourg, France), Novabiochem (Bad Soden, Germany, from 2003 on Merck Biosciences, Darmstadt, Germany) and Acros (Geel, Belgium, distributor Fisher Scientific GmbH, Schwerte, Germany), Peptech (Cambridge, Mass., USA), Synthetech (Albany, Oreg., USA), Pharmacore (High Point, N.C., USA), Anaspec (San Jose, Calif., USA) and used in the specified quality without further purification.

Non commercially available non-conventional amino acids were prepared according to standard protocols either as building blocks for solid phase synthesis or by derivatization of commercially available amino acids during solid phase synthesis.

If not stated differently, concentrations are given as percent by volume.

Analysis of Peptides According to the Present Invention:

The analyses of peptides were performed with analytical HPLC methods followed by either ESI-MS or MALDI-MS detection. For analytic chromatography a Hewlett Packard 1100-system together with an ESI-MS (Finnigan LCQ ion trap mass spectrometer) was used. Helium was used as impact gas in the ion trap. For chromatographic separation a RP-18-column (Vydac (Merck) at 30° C. was used. A binary gradient was applied for all chromatograms (5-95% B, linear, A: 0.1% TFA in water and B: 0.1% TFA in $CH_3CN$). UV detection was at $\lambda=220$ nm.

Analyses by means of HPLC/MS was performed using a linear gradient from 95:5 to 5:95 (A: 0.1% TFA in water and B: 0.1% TFA in acetonitrile), RP columns were from the companies Phenomenex or Waters (Typ Luna C-18, 3 μm, 2.00×50 mm, Symmetry C18 Column MV Kit, 5 μm, 4.6×250 mm, respectively); For ESI-MS measurements a mass spectrometer ThermoFinnigan Advantage and/or LCQ Classic (both iontrap) was used. For ESI ionization helium served as impact gas in the ion trap. In case of MALDI-MS analyses an Applied Biosystems Voyager RP MALDI mass spectrometer was used with α-Cyano-4-hydroxycinnamic acid as internal calibration matrix.

Purification of Peptides with Preparative HPLC:

Preparative HPLC separations were performed using Varian PLRP-S (10 μm, 100 Å) columns (150×25 mm or 150×50 mm) with the following gradient solvents: 0.05% TFA in $H_2O$ and B: 0.05% TFA in $CH_3CN$

TABLE 4

| Abbreviations: | |
|---|---|
| AAV | general procedure |
| Ac | acetyl |
| Acm | Acetamidomethyl |
| DCM | dichloromethane |
| DIC | diisopropylcarbodiimide |
| DIPEA | N,N-diisopropylethylamine |
| DMF | N,N-dimethylformamide |
| DMSO | dimethylsulfoxide |
| eq. | equivalent(s) |
| ESI | Electrospray ionisation |
| FIG. | figure |
| Fmoc | 9-fluorenylmethyloxycarbonyl |
| H | hour(s) |
| HATU | O-(7-azabenzotriazol-1-yl)-1,1,3,3-tetramethyluronium-hexafluorophosphate |
| HBTU | O-(benzotriazol-1-yl)-1,1,3,3-tetramethyluronium-hexafluorophosphate |
| HOBt | 1-hydroxybenzotriazole |
| HPLC | high-pressure liquid chromatography |
| MALDI | Matrix Assisted Laser Desorption/Ionization |
| Me | methyl |
| Min | minute(s) |
| Ml | milliliter |
| MS | Mass spectrometry |
| MW | Molecular weight |
| NMP | N-methylpyrrolidone |
| Ph | phenyl |
| RP | Reversed phase |
| $^t$Bu | tert-butyl |
| THF | tetrahydrofuran |
| TIPS | Triisopropyl silane |
| TFA | trifluoroacetic acid |
| UV | Ultraviolet |

Example 2

Synthesis of Peptides

Linear peptides were synthesized using the Fmoc-$^t$Bu-strategy. The synthesis was done either manually in polypropylene syringes or via an automatic synthesizer (Syro from Multisyntech, Witten or Sophas from Zinsser-Analytic, Frankfurt).

For the preparation of peptides carrying a C-terminal carboxylic acid, the C-terminal amino acid was either attached to a tritylchloride resin (approx. 100 mg resin; loading of reactive groups approx. 1.5 mmol/g; coupling with 0.8 eq. Fmoc-amino acid and 3.0 eq. DIPEA in $CH_2Cl_2$ for 2 h; loading of the first amino acid approx. 0.2-0.4 mmol/g) or to Wang resin (100-200 mg resin; loading of reactive groups approx. 0.6 mmol/g; coupling with 4 eq. Fmoc-amino acid, 4 eq. DIC and 3 eq. NMI in DMF for 3 h; loading of the first amino acid approx. 0.2-0.6 mmol/g).

For the preparation of peptides carrying a C-terminal carboxylic amide, the first amino acid was attached to the resin via Fmoc deprotection of the Fmoc-Rink amide resin (ca. 100 mg resin, ca. 0.5 mmol/g loading; Fmoc deprotection with 20% piperidine in DMF for 20 min) and subsequent coupling of the Fmoc amino acid (reaction with 5 eq. Fmoc amino acid; 5 eq. HBTU or 5 eq. HATU and 10 eq. DIPEA in NMP for 30-60 min and this step was optionally repeated).

For the preparation of peptides carrying a C-terminal cysteamine (Cea), a trityl resin preloaded with cysteamine was used (ca. 120 mg resin, ca 0.4 mmol/g loading) and the first amino acid was attached by subsequent coupling of the Fmoc amino acid (reaction with 5 eq. Fmoc amino acid; 5 eq. HBTU or 5 eq. HATU and 10 eq. DIPEA in NMP for 30-60 min and this step was optionally repeated).

After the coupling of the first amino acid, the synthesis of the peptide was done via a repeated sequence of steps, as necessary, consisting of Fmoc deprotection and coupling of the corresponding Fmoc amino acid or carboxylic acid. For the Fmoc deprotection the resin was treated with 20% piperidine in DMF for 20 min. The coupling of the amino acids was carried out via reaction with 5 eq. of the amino acid, 5 eq. HBTU or 5 eq. HATU and 10 eq. DIPEA in DMF for 30-60 min. Each coupling step was optionally repeated.

For the introduction of the N-terminal acetyl group, the N-terminal free peptide, bound to the resin, was incubated with a solution of 10% acetic acid anhydride and 20% DIPEA in DMF for 20 min. For the introduction of the N-terminal sulfonyl group, the N-terminal free peptide, bound to the resin, was incubated with a solution of 2 eq. of the corresponding sulfonyl chloride and 4 eq. DIPEA in DMF or DCM for 30 min and this treatment was repeated once.

For the cleavage of the peptide from the resin and its side chain protecting groups, a mixture of 95% TFA, 2.5% $H_2O$, 2.5% TIPS or a similar solution was added. Finally the crude peptide was isolated either by evaporation of TFA using a rotary evaporator or by precipitation with the aid of methyl-$^t$butyl-ether at 0° C.

These crude peptides were directly used for the cyclization according to AAV2.

General Procedure (AAV) 2: Cyclization of Peptides Carrying Two Cysteines

Peptides with Unprotected Cysteines:

The crude peptide was dissolved in acetic acid (1-5 mg crude peptide per ml) and 10 eq. of iodine solution (0.5 mM in methanol) were added. After stirring for 1-5 h the reaction mixture was diluted with water (10 times of the reaction volume) and concentrated by solid phase extraction (Varian Bondesil-ENV, 125 nm). The eluate of the crude disulfide was freeze-dried.

Alternatively the peptides with unprotected cysteines were in some cases cyclized by a Pt reagent [Shi and Rabenstein, 2000, *J Am Chem Soc* 122:6809-6815].

Peptides with Acm-Protected Cysteines:

The crude peptide was dissolved in acetic acid (1-5 mg crude peptide per ml), 10 eq. of iodine solution (0.5 mM in methanol) and water (25% of the volume of acetic acid) were added. After stirring for 1-5 h the reaction mixture was diluted with water (10 times the reaction volume) and concentrated by solid phase extraction (Varian Bondesil-ENV, 125 nm). The eluate of the crude disulfide was freeze-dried.

Example 3

Synthesis of H-Met-cyclo(Cys-His-Phe-Gly-Leu-Lys-Leu-Asp-Arg-Ile-Ser-Cys)-NH$_2$ (SEQ ID NO:9)

After linear peptide synthesis, following AAV1, cyclization, following AAV2, and subsequent purification via HPLC, 12 mg of the desired product H-Met-cyclo(Cys-His-Phe-Gly-Leu-Lys-Leu-Asp-Arg-Ile-Ser-Cys)-NH$_2$ (SEQ ID NO:9) were obtained as white solid.

MW (calc)=1518.73, MS (ESI): m/z (found)=1519.8 [(M+H)$^+$], 760.4 [(M+2H)$^{2+}$]. According to the procedure described above (example 3) the listed peptides (table 5) were synthesized, subsequently purified and obtained as white solids.

TABLE 5

Analytical data of selected compounds according to the present invention.

| Compound | amount in [mg] | SEQ ID NO: | Calculated mass vs. found in [amu] ESI-MS (M + H)$^+$ and (M + 2H)$^{2+}$/2 or MALDI-MS |
|---|---|---|---|
| H-met-cyclo(Cys-His-Phe-Gly-Leu-Lys-Leu-Asp-Arg-Ile-Ser-Cys)-NH$_2$ | 7.1 | 10 | 1519.86 MALDI-MS: 1521.0 |
| H-Met-cyclo(cys-His-Phe-Gly-Leu-Lys-Leu-Asp-Arg-Ile-Ser-Cys)-NH$_2$ | 7.6 | 11 | 1519.86 MALDI-MS: 1521.0 |
| H-Met-cyclo(Cys-his-Phe-Gly-Leu-Lys-Leu-Asp-Arg-Ile-Ser-Cys)-NH$_2$ | 6.4 | 12 | 1519.86 MALDI-MS: 1521.0 |
| H-Met-cyclo(cys-His-Phe-Gly-Leu-Lys-Leu-Asp-Arg-Ile-Ser-cys)-NH$_2$ | 5.2 | 13 | 1519.86 MALDI-MS: 1521.0 |
| Ac-Met-cyclo(Cys-His-Phe-Gly-Leu-Lys-Leu-Asp-Arg-Ile-Ser-Cys)-NH$_2$ | 6.0 | 14 | 1560.74 ESI-MS: 1561.8 and 781.9 |
| H-Nle-cyclo(Cys-His-Phe-Gly-Leu-Lys-Leu-Asp-Arg-Ile-Ser-Cys)-NH$_2$ | 6.0 | 16 | 1500.77 ESI-MS: 1501.9 and 751.9 |
| H-Met-cyclo(Cys-Gly-Phe-Gly-Leu-Lys-Leu-Asp-Arg-Ile-Ser-Cys)-NH$_2$ | 6.0 | 17 | 1438.69 ESI-MS: 1439.9 and 720.8 |
| H-Nle-cyclo(Cys-Gly-Phe-Gly-Leu-Lys-Leu-Asp-Arg-Ile-Ser-Cys)-NH$_2$ | 4.6 | 33 | 1521.73 MALDI-MS: 1523.1 |
| H-Met-cyclo(Cys-Gly-Phe-ala-Leu-Lys-Leu-Asp-Arg-Ile-Ser-Cys)-NH$_2$ | 3.2 | 34 | 1452.70 MALDI-MS: 1454.3 |
| H-Met-cyclo(Cys-his-Phe-ala-Leu-Lys-Leu-Asp-Arg-Ile-Ser-Cys)-NH$_2$ | 6.0 | 35 | 1532.74 ESI-MS: 1533.6 and 767.8 |
| H-Met-cyclo(Cys-pro-Phe-Gly-Leu-Lys-Leu-Asp-Arg-Ile-Ser-Cys)-NH$_2$ | 6.1 | 37 | 1479.83 MALDI-MS: 1481.7 |
| H-Met-cyclo(Cys-ala-Phe-Gly-Leu-Lys-Leu-Asp-Arg-Ile-Ser-Cys)-NH$_2$ | 5.2 | 38 | 1453.80 MALDI-MS: 1454.8 |
| H-Met-cyclo(Cys-his-Phe-Gly-Leu-Pro-Leu-Asp-Arg-Ile-Ser-Cys)-NH$_2$ | 5.9 | 41 | 1488.80 MALDI-MS: 1489.8 |
| H-Met-cyclo(Cys-his-Phe-Gly-Leu-Lys-Leu-Asp-Arg-Tbg-Ser-Cys)-NH$_2$ | 6.0 | 43 | 1518.73 ESI-MS: 1519.7 and 760.6 |
| H-Met-cyclo(Cys-his-Phe-Gly-Leu-Nmk-Leu-Asp-Arg-Ile-Ser-Cys)-NH$_2$ | 8.0 | 46 | 1532.74 ESI-MS: 1533.6 and 767.6 |
| H-Met-cyclo(Cys-his-Phe-Gly-Leu-Lys-Nml-Asp-Arg-Ile-Ser-Cys)-NH$_2$ | 7.0 | 47 | 1532.74 ESI-MS: 1533.4 and 767.6 |
| H-Met-cyclo(Cys-his-Phe-Gly-Leu-Lys-Leu-Asp-Nmr-Ile-Ser-Cys)-NH$_2$ | 7.0 | 48 | 1532.74 ESI-MS: 1533.4 and 767.6 |
| H-Met-cyclo(Cys-ala-Phe-Gly-Leu-Pro-Leu-Asp-Arg-Ile-Ser-Cys)-NH$_2$ | 5.3 | 49 | 1421.66 ESI-MS: 1423.9 and 712.2 |
| H-Met-cyclo(Cys-ala-Phe-Gly-Leu-Lys-Ile-Asp-Arg-Ile-Ser-Cys)-NH$_2$ | 5.3 | 53 | 1453.80 ESI-MS: 1455.0 and 727.8 |
| Hex-cyclo(Cys-ala-Phe-Gly-Leu-Lys-Leu-Asp-Arg-Ile-Ser-Cys)-NH$_2$ | 4.2 | 65 | 1419.74 ESI-MS: 1420.6 and 711.2 |
| Occ-cyclo(Cys-ala-Phe-Gly-Leu-Lys-Leu-Asp-Arg-Ile-Ser-Cys)-NH$_2$ | 1.0 | 68 | 1447.77 ESI-MS: 1448.6 and 725.1 |
| Hex-cyclo(Cys-ala-Mcf-Gly-Leu-Lys-Leu-Asp-Arg-Ile-Ser-Cys)-NH$_2$ | 0.9 | 77 | 1453.70 ESI-MS: 1454.4 and 728.1 |
| Hex-cyclo(Cys-aze-Phe-Gly-Leu-Lys-Leu-Asp-Arg-Ile-Ser-Cys)-NH$_2$ | 6.1 | 79 | 1431.74 ESI-MS: 1432.5 and 717.1 |
| Hex-cyclo(Cys-thz-Phe-Gly-Leu-Lys-Leu-Asp-Arg-Ile-Ser-Cys)-NH$_2$ | 1.1 | 80 | 1463.71 ESI-MS: 1464.4 and 733.1 |
| Hex-cyclo(Cys-pip-Phe-Gly-Leu-Lys-Leu-Asp-Arg-Ile-Ser-Cys)-NH$_2$ | 1.3 | 81 | 1459.77 ESI-MS: 1460.5 and 731.1 |
| Hex-cyclo(Cys-ala-Phe-Gly-Leu-Hpr-Leu-Asp-Arg-Ile-Ser-Cys)-NH$_2$ | 4.9 | 86 | 1404.69 ESI-MS: 1405.6 and 703.5 |
| Hex-cyclo(Cys-ala-Phe-Gly-Leu-Lys-Ile-Asp-Arg-Ile-Ser-Cys)-NH$_2$ | 1.3 | 87 | 1419.74 ESI-MS: 1420.4 and 711.1 |
| Hex-cyclo(Cys-ala-Phe-Gly-Leu-Pro-Ile-Asp-Arg-Ile-Ser-Cys)-NH$_2$ | 17.0 | 88 | 1388.69 ESI-MS: 1389.5 and 695.5 |
| Hex-cyclo(Cys-pro-Phe-Gly-Leu-Pro-Ile-Asp-Arg-Ile-Ser-Cys)-NH$_2$ | 14.3 | 89 | 1414.71 ESI-MS: 1415.5 and 708.5 |
| Hex-cyclo(Cys-pro-Phe-Gly-Leu-Lys-Leu-Asp-Arg-Ile-Ser-Cys)-NH$_2$ | 8.1 | 90 | 1445.75 ESI-MS: 1446.4 and 724.1 |
| Hex-cyclo(Cys-pro-Phe-Gly-Leu-Pro-Leu-Asp-Arg-Ile-Ser-Cys)-NH$_2$ | 13.6 | 91 | 1414.71 ESI-MS: 1415.4 and 708.5 |
| Hex-cyclo(Cys-pro-Phe-Gly-Leu-Lys-Ile-Asp-Arg-Ile-Ser-Cys)-NH$_2$ | 4.9 | 92 | 1445.75 ESI-MS: 1446.4 and 724.1 |
| Hex-cyclo(Cys-ala-Phe-Gly-Leu-Pro-Leu-Asp-Arg-Ile-Ser-Cys)-NH$_2$ | 13.3 | 93 | 1388.69 ESI-MS: 1389.5 and 695.4 |

TABLE 5-continued

Analytical data of selected compounds according to the present invention.

| Compound | amount in [mg] | SEQ ID NO: | Calculated mass vs. found in [amu] ESI-MS (M + H)+ and (M + 2H)²⁺/2 or MALDI-MS |
|---|---|---|---|
| Hex-cyclo(Cys-ala-Phe-Gly-Leu-Lys-Npg-Asp-Arg-Ile-Ser-Cys)-NH₂ | 1.2 | 95 | 1433.75 ESI-MS: 1434.6 and 718.1 |
| Hex-cyclo(Cys-ala-Phe-Gly-Leu-Lys-Leu-Asp-Orn-Ile-Ser-Cys)-NH₂ | 23.0 | 96 | 1377.71 ESI-MS: 1378.5 and 690.1 |
| Hex-cyclo(Cys-ala-Mff-Gly-Leu-Lys-Leu-Asp-Arg-Ile-Ser-Cys)-NH₂ | 10.8 | 103 | 1437.73 ESI-MS: 1438.6 and 720.2 |
| Hex-cyclo(Cys-ala-Mmf-Gly-Leu-Lys-Leu-Asp-Arg-Ile-Ser-Cys)-NH₂ | 8.9 | 104 | 1433.75 ESI-MS: 1434.6 and 718.1 |
| Hex-cyclo(Cys-ala-Phe-Gly-Leu-Pro-Leu-Asp-Fhz-Ile-Ser-Cys)-NH₂ | 13.4 | 113 | 1372.69 ESI-MS: 1373.6 and 687.6 |

Example 4

NPR-B Induced Production of Cyclic GMP in Cultured Transformed Human Trabecular Meshwork Cells (GTM-3 Cells)

The efficacy and potency of compounds to activate NPR-B were evaluated in a functional assay using endogenously NPR-B expressing GTM-3 cells (Pang et al. 1994, Curr Eye Res 13:51-63). In this assay the dose dependent production of cyclic GMP (cGMP) is determined and Emax (maximum activation) and $EC_{50}$ values are calculated. The natural occurring ligand for NPR-B, i.e. CNP is used as an internal control and to determine the maximal cGMP production of the cells, which allows the calculation of activation values of the tested compounds relative to CNP.

Preparation of Cells:

In a 96 well white optical bottom tissue culture plate (Nunc, Germany) $3 \times 10^4$ cells/well are seeded in Dulbecco's MEM (DMEM, Biochrom) supplemented with Gentamycin (0.056 mg/ml) and incubated for 18 h with 10% $CO_2$ in a humidified atmosphere.

Stimulation of Cells:

The cell culture medium is aspirated and each well is washed with 200 μl DMEM/Ham's F12=Medium (Gibco). Then, 200 μl Medium supplemented with 1 mM IBMX (3-Isobutyl-1-methyl-xanthin, Sigma) is added to each well and incubated for 15 min. at room temperature. 25 μl of compound dilution is added and the cells are stimulated for 15 min. at room temperature. The stimulation is stopped by aspiration of the medium and addition of 20 μl of Lysis buffer (reagent included in cGMP Assay Kit).

Determination of cGMP:

The amount of produced cGMP in the cells is determined using HitHunter™ cGMP Assay kit (DiscoveRX) according to manufacturer's instructions.

Dilution of compounds: For Emax and $EC_{50}$ determinations, duplicate wells are stimulated with a serial dilution of a 10 mM DMSO compound stock solution. Dilutions are prepared in Medium supplemented with IBMX (1 mM). Final compound concentrations are in the range from 45 μM to 20 nM. Highly active compounds, e.g. CNP are used for stimulation at concentrations ranging from 5 μM to 64 pM.

Example 5

NPR-A Induced Production of Cyclic GMP in Stably Transfected Cell

To assess the specificity of compounds for NPR activation, human 293-T cells transfected with NPR-A (Potter and Garbers 1992, J Biol Chem. 267:14531-14534) are used in stimulation experiments.

In this homogenous assay, the cells are stimulated in suspension with the test compound and the production of cyclic GMP (cGMP) is determined, from which $EC_{50}$ values are calculated. ANP, the naturally occurring ligand of NPR-A is used as an internal control and to determine the maximal cGMP production of the cells, which allows the calculation of activation values of the tested compounds relative to ANP.

Preparation of Cells:

NPR-A transfected 293-T cells are washed once with phosphate buffered saline (PBS) and detached from a 75 cm² tissue culture flask by addition of 3 ml of non enzymatic cell dissociation solution (Sigma-Aldrich) and incubation for 10 min. at room temperature. Detached cells are harvested in 20 ml PBS and centrifuged for 10 min at 200×g at room temperature. The cells are resuspended in DMEM/Ham's F12 mix supplemented with 1 mM IBMX (Medium) and adjusted to a density of $1.25 \times 10^5$ cells/ml and incubated for 15 min. at room temperature.

Stimulation of Cells:

20 μl of cells ($2.5 \times 10^3$ cells) are added to each well of a 96 well white optical bottom tissue culture plate (Nunc, Germany). 10 μl of compound dilution is added and the cells are stimulated for 25 min. at room temperature. The stimulation is stopped by addition of 20 μl of Lysis buffer (reagent included in cGMP Assay Kit).

Determination of cGMP: The amount of produced cGMP in the cells is determined using HitHunter™ cGMP Assay kit (DiscoveRX) according to manufacturer's instructions.

Dilution of Compounds:

For $EC_{50}$ determinations, duplicate wells are stimulated with a serial dilution of a 10 mM DMSO compound stock solution. Dilutions are prepared in Medium supplemented with IBMX (1 mM). The final compound concentration in the assay is in the range from 45 μM to 20 nM. The internal standard compound ANP is used at concentrations ranging from 5 μM to 310 pM.

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

All references cited herein, to the extent that they provide exemplary procedural or other details supplementary to those set forth herein, are specifically incorporated herein by reference.

What is claimed is:

1. A compound of the Formula:

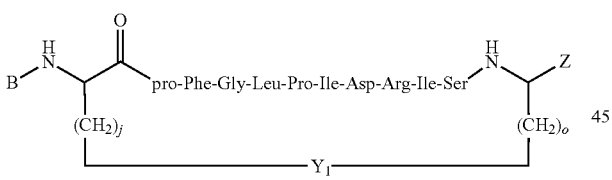

wherein $Y_1$ is selected from the group consisting of —S—, —O—, —S—S—, —CO—NH—, and —NH—CO—;

j and o are, independently, 1 or 2;

B is H, $C_{1-10}$alkyl; alkanoyl; sulfanoyl; alkylcycloalkyl; or aralkyl;

Z is H, —CH$_2$—OH, and —C(=O)—X$^{11}$, wherein X$^{11}$ is selected from the group consisting of OH, —NR$^{11}$R$^{13}$, and —OR$^{14}$;

wherein R$^{11}$ and R$^{13}$ are, independently, selected from the group consisting of H and $C_{1-6}$alkyl; and R$^{14}$ is selected from the group consisting of H, $C_{1-10}$alkyl, and alkylcycloalkyl.

2. The compound of claim 1, wherein $Y_1$ is —S—S—.

3. The compound of claim 1, wherein j is 1 and o is 1.

4. The compound of claim 1, wherein B is a moiety of Formula (XV):

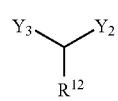

wherein $Y_2$ is selected from the group consisting of —CH$_2$—, —C(=O)—, and —SO$_2$—;

$Y_3$ is absent or, if present, is selected from the group consisting of H, —NH$_2$, and —NHC(=O)—CH$_3$; and R$^{12}$ is selected from the group consisting of $C_{1-8}$alkyl, alkylcycloalkyl, aryl, aralkyl, and alkylsulfide.

5. The compound of claim 1, wherein

B is selected from the group consisting of Met, Nle, Hgl, met, nle, hgl, a N-acetylated derivative of any of the preceding amino acids, Hex, and Occ;

$Y_1$ is —S—S—;

j is 1;

o is 1; and

Z is —C(=O)—NR$^{11}$R$^{13}$, wherein R$^{11}$ and R$^{13}$ are, independently, selected from the group consisting of H and $C_{1-6}$alkyl.

6. The compound of claim 1, wherein the compound is Hex-cyclo(Cys-pro-Phe-Gly-Leu-Pro-Ile-Asp-Arg-Ile-Ser-Cys)-NH$_2$ (SEQ ID NO:89).

7. A compound of Formula XII:

Xaa$_1$-cyclo(Cys-Xaa$_2$-Xaa$_3$-Gly-Leu-Xaa$_4$-Xaa$_5$-Asp-Arg-Ile-Ser-Xaa$_6$)-Z     (XII)

wherein
Xaa₁ is selected from the group consisting of Met, Hex, iPrEtCO, iPrPrCO, Occ, PhEtCO, and PhPrCO, provided that when Xaa₁ is iPrEtCO, iPrPrCO, Occ, PhEtCO, or PhPrCO then Xaa₂ is ala, Xaa₃ is Phe, Xaa₄ is Lys, Xaa₅ is Leu, Xaa₆ is Cys, and Z is NH₂;

Xaa₂ is selected from the group consisting of ala, aze, thz, pip and pro, provided that when Xaa₂ is aze, thz, pip or pro then Xaa₁ is Hex;

Xaa₃ is selected from the group consisting of Phe, Mcf and Mmf, provided that when Xaa₃ is Mcf or Mmf then Xaa₁ is Hex;

Xaa₄ is selected from the group consisting of Pro, Lys, Hpa and Hpr, provided that when Xaa₄ is Hpa or Hpr then Xaa₁ is Hex;

Xaa₅ is selected from the group consisting of Leu, Ile, Nle, and Npg, provided that when Xaa₅ is Nle or Npg then Xaa₁ is Hex;

Xaa₆ is selected from the group consisting of Cys and Cea, provided that when Xaa₆ is Cea then Xaa₁ is Met or Hex and Z is H; and Z is selected from the group consisting of NH₂ and H.

8. The compound of claim 7, wherein the compound is selected from the group consisting of:

H-Met-cyclo(Cys-ala-Phe-Gly-Leu-Pro-Leu-Asp-Arg-Ile-Ser-Cys)-NH₂ (SEQ ID NO:49); H-Met-cyclo(Cys-ala-Phe-Gly-Leu-Lys-Ile-Asp-Arg-Ile-Ser-Cys)-NH₂ (SEQ ID NO:53); H-Met-cyclo(Cys-ala-Phe-Gly-Leu-Lys-Leu-Asp-Arg-Ile-Ser-Cea) (SEQ ID NO:61); iPrEtCO-cyclo(Cys-ala-Phe-Gly-Leu-Lys-Leu-Asp-Arg-Ile-Ser-Cys)-NH₂ (SEQ ID NO:64); Hex-cyclo(Cys-ala-Phe-Gly-Leu-Lys-Leu-Asp-Arg-Ile-Ser-Cys)-NH₂ (SEQ ID NO:65); iPrPrCO-cyclo(Cys-ala-Phe-Gly-Leu-Lys-Leu-Asp-Arg-Ile-Ser-Cys)-NH₂ (SEQ ID NO:67); Occ-cyclo(Cys-ala-Phe-Gly-Leu-Lys-Leu-Asp-Arg-Ile-Ser-Cys)-NH₂ (SEQ ID NO:68); PhEtCO-cyclo(Cys-ala-Phe-Gly-Leu-Lys-Leu-Asp-Arg-Ile-Ser-Cys)-NH₂ (SEQ ID NO:70); PhPrCO-cyclo(Cys-ala-Phe-Gly-Leu-Lys-Leu-Asp-Arg-Ile-Ser-Cys)-NH₂ (SEQ ID NO:72); Hex-cyclo(Cys-ala-Mcf-Gly-Leu-Lys-Leu-Asp-Arg-Ile-Ser-Cys)-NH₂ (SEQ ID NO:77); Hex-cyclo(Cys-aze-Phe-Gly-Leu-Lys-Leu-Asp-Arg-Ile-Ser-Cys)-NH₂ (SEQ ID NO:79); Hex-cyclo(Cys-thz-Phe-Gly-Leu-Lys-Leu-Asp-Arg-Ile-Ser-Cys)-NH₂ (SEQ ID NO:80); Hex-cyclo(Cys-pip-Phe-Gly-Leu-Lys-Leu-Asp-Arg-Ile-Ser-Cys)-NH₂ (SEQ ID NO:81); Hex-cyclo(Cys-ala-Phe-Gly-Leu-Lys-Nle-Asp-Arg-Ile-Ser-Cys)-NH₂ (SEQ ID NO:83); Hex-cyclo(Cys-ala-Phe-Gly-Leu-Hpa-Leu-Asp-Arg-Ile-Ser-Cys)-NH₂ (SEQ ID NO:85); Hex-cyclo(Cys-ala-Phe-Gly-Leu-Hpr-Leu-Asp-Arg-Ile-Ser-Cys)-NH₂ (SEQ ID NO:86); Hex-cyclo(Cys-ala-Phe-Gly-Leu-Lys-Ile-Asp-Arg-Ile-Ser-Cys)-NH₂ (SEQ ID NO:87); Hex-cyclo(Cys-ala-Phe-Gly-Leu-Pro-Ile-Asp-Arg-Ile-Ser-Cys)-NH₂ (SEQ ID NO:88); Hex-cyclo(Cys-pro-Phe-Gly-Leu-Pro-Ile-Asp-Arg-Ile-Ser-Cys)-NH₂ (SEQ ID NO:89); Hex-cyclo(Cys-pro-Phe-Gly-Leu-Lys-Leu-Asp-Arg-Ile-Ser-Cys)-NH₂ (SEQ ID NO:90); Hex-cyclo(Cys-pro-Phe-Gly-Leu-Pro-Leu-Asp-Arg-Ile-Ser-Cys)-NH₂ (SEQ ID NO:91); Hex-cyclo(Cys-pro-Phe-Gly-Leu-Lys-Ile-Asp-Arg-Ile-Ser-Cys)-NH₂ (SEQ ID NO:92); Hex-cyclo(Cys-ala-Phe-Gly-Leu-Pro-Leu-Asp-Arg-Ile-Ser-Cys)-NH₂ (SEQ ID NO:93); Hex-cyclo(Cys-ala-Phe-Gly-Leu-Lys-Npg-Asp-Arg-Ile-Ser-Cys)-NH₂ (SEQ ID NO:95); Hex-cyclo(Cys-ala-Mmf-Gly-Leu-Lys-Leu-Asp-Arg-Ile-Ser-Cys)-NH₂ (SEQ ID NO: 104); and Hex-cyclo(Cys-ala-Phe-Gly-Leu-Lys-Leu-Asp-Arg-Ile-Ser-Cea) (SEQ ID NO: 120).

9. A compound of Formula XIV:

Xaa₁-cyclo(Cys-Xaa₂-Xaa₃-Gly-Xaa₄-Lys-Leu-Asp-Xaa₅-Xaa₆-Ser-Cys)-Z  (XIV)

Wherein
Xaa₁ is selected from the group consisting of Met, Hex, Nle and H, provided that when Xaa₁ is Nle then Xaa₂ is His, Xaa₃ is Phe, Xaa₄ is Leu, Xaa₅ is Arg, Xaa₆ is Ile, and Z is NH₂, and when Xaa₁ is H, then Xaa₂ is ala, Xaa₃ is Phe, Xaa₄ is Leu, Xaa₅ is Arg, Xaa₆ is Ile, and Z is NH₂;

Xaa₂ is selected from the group consisting of His, Gab, phe and ala, provided that when Xaa₂ is Gab or phe then Xaa₁ is Met;

Xaa₃ is selected from the group consisting of Phe, Pcf, Pff, and Mtf, provided that when Xaa₃ is Pcf, or Pff then Xaa₁ is Met, and when Xaa₃ is Mtf then Xaa₁ is Hex;

Xaa₄ is selected from the group consisting of Leu and Ala, provided that when Xaa₄ is Ala then Xaa₁ is Met;

Xaa₅ is selected from the group consisting of Arg, Bmr, Aof, and Nar, provided that when Xaa₅ is Bmr, Aof or Nar then Xaa₁ is Hex, Xaa₂ is ala, Xaa₃ is Phe, Xaa₄ is Leu, Xaa₆ is Ile and Z is NH₂;

Xaa₆ is selected from the group consisting of Ile, Atp and Att, provided that when Xaa₆ is Atp or Att then Xaa₁ is Hex, Xaa₂ is ala, Xaa₃ is Phe, Xaa₄ is Leu, Xaa₅ is Arg and Z is NH₂; and Z is selected from the group consisting of NH₂, Trp-Arg-NH₂, His-Arg-NH₂, OH, and Tyr-Ser-NH₂, provided that when Z is anything other than NH₂ then Xaa₁ is Met, Xaa₂ is His, Xaa₃ is Phe, Xaa₄ is Leu, Xaa₅ is Arg, and Xaa₆ is Ile.

10. The compound of claim 9, wherein the compound is selected from the group consisting of:

iPrEtCO-cyclo(Cys-ala-Phe-Gly-Leu-Lys-Leu-Asp-Arg-Ile-Ser-Cys)-NH₂ (SEQ ID NO:64); Hex-cyclo(Cys-ala-Phe-Gly-Leu-Lys-Leu-Asp-Arg-Ile-Ser-Cys)-NH₂ (SEQ ID NO:65); iPrPrCO-cyclo(Cys-ala-Phe-Gly-Leu-Lys-Leu-Asp-Arg-Ile-Ser-Cys)-NH₂ (SEQ ID NO:67); Occ-cyclo(Cys-ala-Phe-Gly-Leu-Lys-Leu-Asp-Arg-Ile-Ser-Cys)-NH₂ (SEQ ID NO:68); PhEtCO-cyclo(Cys-ala-Phe-Gly-Leu-Lys-Leu-Asp-Arg-Ile-Ser-Cys)-NH₂ (SEQ ID NO:70); and PhPrCO-cyclo(Cys-ala-Phe-Gly-Leu-Lys-Leu-Asp-Arg-Ile-Ser-Cys)-NH₂ (SEQ ID NO:72).

11. A compound of the Formula:

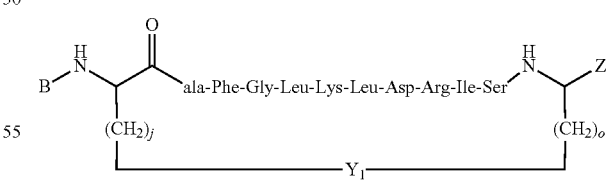

wherein
$Y_1$ is selected from the group consisting of —S—, —O—, —S—S—, —CO—NH—, and —NH—CO—; and
j and o are, independently, 1 or 2;
B is H, $C_{1-10}$alkyl; alkanoyl; sulfanoyl; alkylcycloalkyl; or aralkyl; and
Z is H, —CH₂—OH, and —C(=O)—$X^{11}$, wherein $X^{11}$ is selected from the group consisting of OH, —NR¹¹R¹³, or —OR¹⁴;

wherein $R^{11}$ and $R^{13}$ are, independently, selected from the group consisting of H and $C_{1-6}$alkyl; and $R^{14}$ is selected from the group consisting of H, $C_{1-10}$alkyl, and alkylcycloalkyl.

12. The compound of claim 11, wherein $Y_1$ is —S—S—.

13. The compound of claim 11, wherein j is 1 and o is 1.

14. The compound of claim 11, wherein the compound is selected from the group consisting of:

H-Met-cyclo(Cys-ala-Phe-Gly-Leu-Lys-Leu-Asp-Arg-Ile-Ser-Cea) (SEQ ID NO:61); iPrEtCO-cyclo(Cys-ala-Phe-Gly-Leu-Lys-Leu-Asp-Arg-Ile-Ser-Cys)-NH$_2$ (SEQ ID NO:64); Hex-cyclo(Cys-ala-Phe-Gly-Leu-Lys-Leu-Asp-Arg-Ile-Ser-Cys)-NH$_2$ (SEQ ID NO:65); iPrPrCO-cyclo(Cys-ala-Phe-Gly-Leu-Lys-Leu-Asp-Arg-Ile-Ser-Cys)-NH$_2$ (SEQ ID NO:67); Occ-cyclo(Cys-ala-Phe-Gly-Leu-Lys-Leu-Asp-Arg-Ile-Ser-Cys)-NH$_2$ (SEQ ID NO:68); PhEtCO-cyclo(Cys-ala-Phe-Gly-Leu-Lys-Leu-Asp-Arg-Ile-Ser-Cys)-NH$_2$ (SEQ ID NO:70); and PhPrCO-cyclo(Cys-ala-Phe-Gly-Leu-Lys-Leu-Asp-Arg-Ile-Ser-Cys)-NH$_2$ (SEQ ID NO:72).

15. A compound of the Formula:

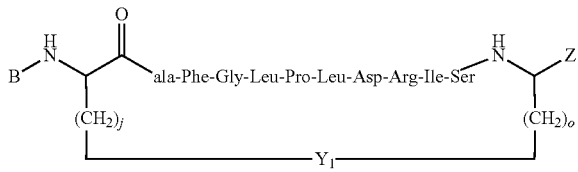

wherein
$Y_1$ is selected from the group consisting of —S—, —O—, —S—S—, —CO—NH—, and —NH—CO—; and
j and o are, independently, 1 or 2;
B is H, $C_{1-10}$alkyl; alkanoyl; sulfanoyl; alkylcycloalkyl; or aralkyl; and
Z is H, —CH$_2$—OH, and —C(=O)—X$^{11}$, wherein X$^{11}$ is selected from the group consisting of OH, —NR$^{11}$R$^{13}$, or —OR$^{14}$;

wherein $R^{11}$ and $R^{13}$ are, independently, selected from the group consisting of H and $C_{1-6}$alkyl; and
$R^{14}$ is selected from the group consisting of H, $C_{1-10}$alkyl, and alkylcycloalkyl.

16. The compound of claim 15, wherein $Y_1$ is —S—S—.

17. The compound of claim 15, wherein the compound is H-Met-cyclo(Cys-ala-Phe-Gly-Leu-Pro-Leu-Asp-Arg-Ile-Ser-Cys)-NH$_2$ (SEQ ID NO:49); or Hex-cyclo(Cys-ala-Phe-Gly-Leu-Pro-Leu-Asp-Arg-Ile-Ser-Cys)-NH$_2$ (SEQ ID NO:93).

18. A compound of the Formula:

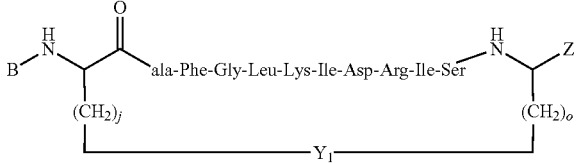

wherein
$Y_1$ is selected from the group consisting of —S—, —O—, —S—S—, —CO—NH—, and —NH—CO—; and
j and o are, independently, 1 or 2;
B is H, $C_{1-10}$alkyl; alkanoyl; sulfanoyl; alkylcycloalkyl; or aralkyl; and
Z is H, —CH$_2$—OH, and —C(=O)—X$^{11}$, wherein X$^{11}$ is selected from the group consisting of OH, —NR$^{11}$R$^{13}$, or —OR$^{14}$;
wherein $R^{11}$ and $R^{13}$ are, independently, selected from the group consisting of H and $C_{1-6}$alkyl; and
$R^{14}$ is selected from the group consisting of H, $C_{1-10}$alkyl, and alkylcycloalkyl.

19. The compound of claim 18, wherein $Y_1$ is —S—S—.

20. The compound of claim 18, wherein the compound is H-Met-cyclo(Cys-ala-Phe-Gly-Leu-Lys-Ile-Asp-Arg-Ile-Ser-Cys)-NH$_2$ (SEQ ID NO:53); or Hex-cyclo(Cys-ala-Phe-Gly-Leu-Lys-Ile-Asp-Arg-Ile-Ser-Cys)-NH$_2$ (SEQ ID NO:87).

* * * * *

SEQUENCE LISTING

<160> NUMBER OF SEQ ID NOS: 121

<210> SEQ ID NO 1
<211> LENGTH: 28
<212> TYPE: PRT
<213> ORGANISM: Homo sapiens
<220> FEATURE:
<221> NAME/KEY: DISULFID
<222> LOCATION: (7)..(23)

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Homo sapiens
<220> FEATURE:
<221> NAME/KEY: DISULFID
<222> LOCATION: (10)..(26)

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 3
<211> LENGTH: 22
<212> TYPE: PRT
<213> ORGANISM: Homo sapiens
<220> FEATURE:
<221> NAME/KEY: DISULFID
<222> LOCATION: (6)..(22)

<400> SEQUENCE: 3

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 4
<211> LENGTH: 15
<212> TYPE: PRT
<213> ORGANISM: Homo sapiens
<220> FEATURE:
<221> NAME/KEY: DISULFID
<222> LOCATION: (2)..(13)

<400> SEQUENCE: 4

Met Cys His Phe Gly Gly Arg Met Asp Arg Ile Ser Cys Tyr Arg
1               5                   10                  15

<210> SEQ ID NO 5
<211> LENGTH: 15
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

```
<400> SEQUENCE: 5

Met Cys His Phe Gly Leu Lys Leu Asp Arg Ile Ser Cys Tyr Arg
1               5                   10                  15

<210> SEQ ID NO 6
<211> LENGTH: 14
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 6

Met Cys His Phe Gly Leu Lys Leu Asp Arg Ile Ser Cys Tyr
1               5                   10

<210> SEQ ID NO 7
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 7

Met Cys His Phe Gly Leu Lys Leu Asp Arg Ile Ser Cys
1               5                   10

<210> SEQ ID NO 8
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 8

Met Cys Ala Phe Gly Leu Lys Leu Asp Arg Ile Ser Cys
1               5                   10

<210> SEQ ID NO 9
<211> LENGTH: 13
<212> TYPE: PRT
<213> ORGANISM: Homo sapiens
<220> FEATURE:
<221> NAME/KEY: DISULFID
<222> LOCATION: (2)..(13)

<400> SEQUENCE: 9

Met Cys His Phe Gly Ala Lys Leu Asp Arg Ile Ser Cys
1               5                   10

<210> SEQ ID NO 10
<211> LENGTH: 13
<212> TYPE: PRT
<213> ORGANISM: Homo sapiens
```

```
<220> FEATURE:
<223> OTHER INFORMATION: N-term H
<220> FEATURE:
<221> NAME/KEY: MISC_FEATURE
<222> LOCATION: (1)..(1)
<223> OTHER INFORMATION: D-form of amino acid at this position
<220> FEATURE:
<221> NAME/KEY: DISULFID
<222> LOCATION: (2)..(13)
<220> FEATURE:
<223> OTHER INFORMATION: C-term NH2

<400> SEQUENCE: 10

Met Cys His Phe Gly Leu Lys Leu Asp Arg Ile Ser Cys
1               5                   10

<210> SEQ ID NO 11
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (2)..(2)
<223> OTHER INFORMATION: D-form of amino acid at this position

<400> SEQUENCE: 11

Met Cys His Phe Gly Leu Lys Leu Asp Arg Ile Ser Cys
1               5                   10

<210> SEQ ID NO 12
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D-form of amino acid at this position
<220> FEATURE:
<223> OTHER INFORMATION: C-term NH2

<400> SEQUENCE: 12

Met Cys His Phe Gly Leu Lys Leu Asp Arg Ile Ser Cys
1               5                   10

<210> SEQ ID NO 13
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (2)..(2)
<223> OTHER INFORMATION: D-form of amino acid at this position
<220> FEATURE:
<221> NAME/KEY: MISC_FEATURE
<222> LOCATION: (13)..(13)
<223> OTHER INFORMATION: D-form of amino acid at this position

<400> SEQUENCE: 13

Met Cys His Phe Gly Leu Lys Leu Asp Arg Ile Ser Cys
1               5                   10
```

```
<210> SEQ ID NO 14
<211> LENGTH: 13
<212> TYPE: PRT
<213> ORGANISM: Homo sapiens
<220> FEATURE:
<223> OTHER INFORMATION: N-term Ac
<220> FEATURE:
<221> NAME/KEY: MISC_FEATURE
<222> LOCATION: (1)..(1)
<223> OTHER INFORMATION: Xaa = Ac-Met
<220> FEATURE:
<221> NAME/KEY: DISULFID
<222> LOCATION: (2)..(13)
<220> FEATURE:
<223> OTHER INFORMATION: C-term NH2

<400> SEQUENCE: 14

Xaa Cys His Phe Gly Leu Lys Leu Asp Arg Ile Ser Cys
1               5                   10

<210> SEQ ID NO 15
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (13)..(13)
<223> OTHER INFORMATION: Xaa = Cys-OH

<400> SEQUENCE: 15

Met Cys His Phe Gly Leu Lys Leu Asp Arg Ile Ser Xaa
1               5                   10

<210> SEQ ID NO 16
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = (S)-norleucine
<220> FEATURE:
<221> NAME/KEY: DISULFID
<222> LOCATION: (2)..(13)
<220> FEATURE:
<221> NAME/KEY: DISULFID
<222> LOCATION: (3)..(14)

<400> SEQUENCE: 16

Xaa Met Cys His Phe Gly Leu Lys Leu Asp Arg Ile Ser Cys
1               5                   10

<210> SEQ ID NO 17
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 17

Met Cys Gly Phe Gly Leu Lys Leu Asp Arg Ile Ser Cys
1               5                   10
```

```
<210> SEQ ID NO 18
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 18

Met Cys Ser Phe Gly Leu Lys Leu Asp Arg Ile Ser Cys
1               5                   10

<210> SEQ ID NO 19
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 19

Met Cys His Phe Gly Asp Lys Leu Asp Arg Ile Ser Cys
1               5                   10

<210> SEQ ID NO 20
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 20

Met Cys His Phe Gly His Lys Leu Asp Arg Ile Ser Cys
1               5                   10

<210> SEQ ID NO 21
<211> LENGTH: 15
<212> TYPE: PRT
<213> ORGANISM: Homo sapiens
<220> FEATURE:
<221> NAME/KEY: DISULFID
<222> LOCATION: (2)..(13)

<400> SEQUENCE: 21

Met Cys His Phe Gly Leu Lys Leu Asp Arg Ile Ser Cys Trp Arg
1               5                   10                  15

<210> SEQ ID NO 22
<211> LENGTH: 15
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
```

<223> OTHER INFORMATION: C-term NH2

<400> SEQUENCE: 22

Met Cys His Phe Gly Leu Lys Leu Asp Arg Ile Ser Cys Asn Arg
1               5                   10                  15

<210> SEQ ID NO 23
<211> LENGTH: 15
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 23

Met Cys His Phe Gly Leu Lys Leu Asp Arg Ile Ser Cys Leu Arg
1               5                   10                  15

<210> SEQ ID NO 24
<211> LENGTH: 15
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 24

Met Cys His Phe Gly Leu Lys Leu Asp Arg Ile Ser Cys Ser Arg
1               5                   10                  15

<210> SEQ ID NO 25
<211> LENGTH: 15
<212> TYPE: PRT
<213> ORGANISM: Homo sapiens
<220> FEATURE:
<221> NAME/KEY: DISULFID
<222> LOCATION: (2)..(13)

<400> SEQUENCE: 25

Met Cys His Phe Gly Leu Lys Leu Asp Arg Ile Ser Cys His Arg
1               5                   10                  15

<210> SEQ ID NO 26
<211> LENGTH: 15
<212> TYPE: PRT
<213> ORGANISM: Homo sapiens
<220> FEATURE:
<221> NAME/KEY: DISULFID
<222> LOCATION: (2)..(13)

<400> SEQUENCE: 26

Met Cys His Phe Gly Leu Lys Leu Asp Arg Ile Ser Cys Tyr Ser
1               5                   10                  15

<210> SEQ ID NO 27
<211> LENGTH: 15
<212> TYPE: PRT
<213> ORGANISM: Homo sapiens
<220> FEATURE:
<223> OTHER INFORMATION: N-term H
<220> FEATURE:

<221> NAME/KEY: DISULFID
<222> LOCATION: (2)..(13)
<220> FEATURE:
<223> OTHER INFORMATION: C-term NH2

<400> SEQUENCE: 27

Met Cys His Phe Gly Leu Lys Leu Asp Arg Ile Ser Cys Tyr Asn
1               5                   10                  15

<210> SEQ ID NO 28
<211> LENGTH: 15
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<223> OTHER INFORMATION: C-term NH2

<400> SEQUENCE: 28

Met Cys His Phe Gly Leu Lys Leu Asp Arg Ile Ser Cys Tyr His
1               5                   10                  15

<210> SEQ ID NO 29
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (4)..(4)
<223> OTHER INFORMATION: Xaa = (S)-para-chloro-phenylalanine

<400> SEQUENCE: 29

Met Cys His Xaa Gly Leu Lys Leu Asp Arg Ile Ser Cys
1               5                   10

<210> SEQ ID NO 30
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (4)..(4)
<223> OTHER INFORMATION: Xaa = (S)-para-fluoro-phenylalanine

<400> SEQUENCE: 30

Met Cys His Xaa Gly Leu Lys Leu Asp Arg Ile Ser Cys
1               5                   10

<210> SEQ ID NO 31
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: Xaa = beta-alanine
<220> FEATURE:

```
<223> OTHER INFORMATION: C-term NH2

<400> SEQUENCE: 31

Met Cys Xaa Phe Gly Leu Lys Leu Asp Arg Ile Ser Cys
1               5                   10

<210> SEQ ID NO 32
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: Xaa = 4-amino-butyric acid

<400> SEQUENCE: 32

Met Cys Xaa Phe Gly Leu Lys Leu Asp Arg Ile Ser Cys
1               5                   10

<210> SEQ ID NO 33
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: MISC_FEATURE
<222> LOCATION: (1)..(1)
<223> OTHER INFORMATION: Xaa = (S)-norleucine
<220> FEATURE:
<221> NAME/KEY: DISULFID
<222> LOCATION: (2)..(13)
<220> FEATURE:
<223> OTHER INFORMATION: C-term NH2

<400> SEQUENCE: 33

Xaa Cys Gly Phe Gly Leu Lys Leu Asp Arg Ile Ser Cys
1               5                   10

<210> SEQ ID NO 34
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (5)..(5)
<223> OTHER INFORMATION: D form of amino acid at this position
<220> FEATURE:
<223> OTHER INFORMATION: C-term NH2

<400> SEQUENCE: 34

Met Cys Gly Phe Ala Leu Lys Leu Asp Arg Ile Ser Cys
1               5                   10

<210> SEQ ID NO 35
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
```

```
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: D form of amino acid at this position
<220> FEATURE:
<223> OTHER INFORMATION: C-term NH2

<400> SEQUENCE: 35

Met Cys His Phe Ala Leu Lys Leu Asp Arg Ile Ser Cys
1               5                   10

<210> SEQ ID NO 36
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = 2-amino-isobutyric acid
<220> FEATURE:
<223> OTHER INFORMATION: C-term NH2

<400> SEQUENCE: 36

Met Cys His Phe Xaa Leu Lys Leu Asp Arg Ile Ser Cys
1               5                   10

<210> SEQ ID NO 37
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 37

Met Cys Pro Phe Gly Leu Lys Leu Asp Arg Ile Ser Cys
1               5                   10

<210> SEQ ID NO 38
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
```

<223> OTHER INFORMATION: C-term NH2

<400> SEQUENCE: 38

Met Cys Ala Phe Gly Leu Lys Leu Asp Arg Ile Ser Cys
1               5                   10

<210> SEQ ID NO 39
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 39

Met Cys Ser Phe Gly Leu Lys Leu Asp Arg Ile Ser Cys
1               5                   10

<210> SEQ ID NO 40
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 40

Met Cys Asn Phe Gly Leu Lys Leu Asp Arg Ile Ser Cys
1               5                   10

<210> SEQ ID NO 41
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 41

Met Cys His Phe Gly Leu Pro Leu Asp Arg Ile Ser Cys
1               5                   10

<210> SEQ ID NO 42
<211> LENGTH: 13
<212> TYPE: PRT
<213> ORGANISM: Homo sapiens
<220> FEATURE:

```
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 42

Met Cys His Phe Gly Leu Arg Leu Asp Arg Ile Ser Cys
1               5                   10

<210> SEQ ID NO 43
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (S)-alpha-tert-butylglycine
<220> FEATURE:
<223> OTHER INFORMATION: C-term NH2

<400> SEQUENCE: 43

Met Cys His Phe Gly Leu Lys Leu Asp Arg Xaa Ser Cys
1               5                   10

<210> SEQ ID NO 44
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: Xaa = (R)--2-thienyl-alanine
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 44

Met Cys Xaa Phe Gly Leu Lys Leu Asp Arg Ile Ser Cys
1               5                   10

<210> SEQ ID NO 45
<211> LENGTH: 13
<212> TYPE: PRT
<213> ORGANISM: Homo sapiens
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
```

<223> OTHER INFORMATION: D form of amino acid at this position

<400> SEQUENCE: 45

Met Cys Phe Phe Gly Leu Lys Leu Asp Arg Ile Ser Cys
1               5                   10

<210> SEQ ID NO 46
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-lysine
<220> FEATURE:
<223> OTHER INFORMATION: C-term NH2

<400> SEQUENCE: 46

Met Cys His Phe Gly Leu Xaa Leu Asp Arg Ile Ser Cys
1               5                   10

<210> SEQ ID NO 47
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-N-methyl-leucine
<220> FEATURE:
<223> OTHER INFORMATION: C-term NH2

<400> SEQUENCE: 47

Met Cys His Phe Gly Leu Lys Xaa Asp Arg Ile Ser Cys
1               5                   10

<210> SEQ ID NO 48
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = (S)-N-methyl-arginine
<220> FEATURE:
<223> OTHER INFORMATION: C-term NH2

<400> SEQUENCE: 48

Met Cys His Phe Gly Leu Lys Leu Asp Xaa Ile Ser Cys
1               5                   10

<210> SEQ ID NO 49
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 49

Met Cys Ala Phe Gly Leu Pro Leu Asp Arg Ile Ser Cys
1               5                   10

<210> SEQ ID NO 50
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-2,4-diaminobutyric acid
<220> FEATURE:
<223> OTHER INFORMATION: C-term NH2

<400> SEQUENCE: 50

Met Cys Ala Phe Gly Leu Xaa Leu Asp Arg Ile Ser Cys
1               5                   10

<210> SEQ ID NO 51
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-ornithine
<220> FEATURE:
<223> OTHER INFORMATION: C-term NH2

<400> SEQUENCE: 51

Met Cys Ala Phe Gly Leu Xaa Leu Asp Arg Ile Ser Cys
1               5                   10

```
<210> SEQ ID NO 52
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-homo-lysine
<220> FEATURE:
<223> OTHER INFORMATION: C-term NH2

<400> SEQUENCE: 52

Met Cys Ala Phe Gly Leu Xaa Leu Asp Arg Ile Ser Cys
1               5                   10

<210> SEQ ID NO 53
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 53

Met Cys Ala Phe Gly Leu Lys Ile Asp Arg Ile Ser Cys
1               5                   10

<210> SEQ ID NO 54
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 54

Met Cys Ala Phe Gly Leu Lys Val Asp Arg Ile Ser Cys
1               5                   10

<210> SEQ ID NO 55
<211> LENGTH: 13
<212> TYPE: PRT
<213> ORGANISM: Homo sapiens
<220> FEATURE:
<223> OTHER INFORMATION: N-term H
<220> FEATURE:
```

```
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (R)-cysteic acid
<220> FEATURE:
<223> OTHER INFORMATION: C-term NH2

<400> SEQUENCE: 55

Met Cys Ala Phe Gly Leu Lys Leu Xaa Arg Ile Ser Cys
1               5                   10

<210> SEQ ID NO 56
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 56

Met Cys Ala Phe Gly Leu Lys Leu Asp Arg Leu Ser Cys
1               5                   10

<210> SEQ ID NO 57
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 57

Met Cys Ala Phe Gly Leu Lys Leu Asp Arg Val Ser Cys
1               5                   10

<210> SEQ ID NO 58
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (12)..(12)
```

```
<223> OTHER INFORMATION: Xaa = beta-alanine
<220> FEATURE:
<223> OTHER INFORMATION: C-term NH2

<400> SEQUENCE: 58

Met Cys Ala Phe Gly Leu Lys Leu Asp Arg Ile Xaa Cys
1               5                   10

<210> SEQ ID NO 59
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (2)..(2)
<223> OTHER INFORMATION: Xaa = (S)-homo-cysteine
<220> FEATURE:
<221> NAME/KEY: MISC_FEATURE
<222> LOCATION: (3)..(3)
<223> OTHER INFORMATION: D form of amino acid at this position
<220> FEATURE:
<223> OTHER INFORMATION: C-term NH2

<400> SEQUENCE: 59

Met Xaa Ala Phe Gly Leu Lys Leu Asp Arg Ile Ser Cys
1               5                   10

<210> SEQ ID NO 60
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (2)..(2)
<223> OTHER INFORMATION: Xaa = (S)-homo-cysteine
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (13)..(13)
<223> OTHER INFORMATION: Xaa = (S)-homo-cysteine
<220> FEATURE:
<223> OTHER INFORMATION: C-term NH2

<400> SEQUENCE: 60

Met Xaa Ala Phe Gly Leu Lys Leu Asp Arg Ile Ser Xaa
1               5                   10

<210> SEQ ID NO 61
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
```

```
<220> FEATURE:
<221> NAME/KEY: MISC_FEATURE
<222> LOCATION: (13)..(13)
<223> OTHER INFORMATION: Xaa = 2-aminoethanethiol

<400> SEQUENCE: 61

Met Cys Ala Phe Gly Leu Lys Leu Asp Arg Ile Ser Xaa
1               5                   10

<210> SEQ ID NO 62
<211> LENGTH: 12
<212> TYPE: PRT
<213> ORGANISM: Homo sapiens
<220> FEATURE:
<223> OTHER INFORMATION: N-term EtCO
<220> FEATURE:
<221> NAME/KEY: DISULFID
<222> LOCATION: (1)..(12)
<220> FEATURE:
<221> NAME/KEY: MISC_FEATURE
<222> LOCATION: (1)..(2)
<223> OTHER INFORMATION: D form of amino acid at this position
<220> FEATURE:
<223> OTHER INFORMATION: C-term NH2

<400> SEQUENCE: 62

Cys Ala Phe Gly Leu Lys Leu Asp Arg Ile Ser Cys
1               5                   10

<210> SEQ ID NO 63
<211> LENGTH: 12
<212> TYPE: PRT
<213> ORGANISM: Homo sapiens
<220> FEATURE:
<223> OTHER INFORMATION: N-term iPrCH2CO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 63

Cys Ala Phe Gly Leu Lys Leu Asp Arg Ile Ser Cys
1               5                   10

<210> SEQ ID NO 64
<211> LENGTH: 12
<212> TYPE: PRT
<213> ORGANISM: Homo sapiens
<220> FEATURE:
<223> OTHER INFORMATION: N-term iPrEtCO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 64

Cys Ala Phe Gly Leu Lys Leu Asp Arg Ile Ser Cys
1               5                   10

<210> SEQ ID NO 65
<211> LENGTH: 12
```

```
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 65

Cys Ala Phe Gly Leu Lys Leu Asp Arg Ile Ser Cys
1               5                   10

<210> SEQ ID NO 66
<211> LENGTH: 12
<212> TYPE: PRT
<213> ORGANISM: Homo sapiens
<220> FEATURE:
<223> OTHER INFORMATION: N-term PhCO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 66

Cys Ala Phe Gly Leu Lys Leu Asp Arg Ile Ser Cys
1               5                   10

<210> SEQ ID NO 67
<211> LENGTH: 12
<212> TYPE: PRT
<213> ORGANISM: Homo sapiens
<220> FEATURE:
<223> OTHER INFORMATION: N-term iPrPrCO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 67

Cys Ala Phe Gly Leu Lys Leu Asp Arg Ile Ser Cys
1               5                   10

<210> SEQ ID NO 68
<211> LENGTH: 12
<212> TYPE: PRT
<213> ORGANISM: Homo sapiens
<220> FEATURE:
<223> OTHER INFORMATION: N-term Occ
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2
```

<400> SEQUENCE: 68

Cys Ala Phe Gly Leu Lys Leu Asp Arg Ile Ser Cys
1               5                   10

<210> SEQ ID NO 69
<211> LENGTH: 12
<212> TYPE: PRT
<213> ORGANISM: Homo sapiens
<220> FEATURE:
<223> OTHER INFORMATION: N-term PhCH2CO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 69

Cys Ala Phe Gly Leu Lys Leu Asp Arg Ile Ser Cys
1               5                   10

<210> SEQ ID NO 70
<211> LENGTH: 12
<212> TYPE: PRT
<213> ORGANISM: Homo sapiens
<220> FEATURE:
<223> OTHER INFORMATION: N-term PhEtCO
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 70

Cys Ala Phe Gly Leu Lys Leu Asp Arg Ile Ser Cys
1               5                   10

<210> SEQ ID NO 71
<211> LENGTH: 12
<212> TYPE: PRT
<213> ORGANISM: Homo sapiens
<220> FEATURE:
<223> OTHER INFORMATION: N-term ButSO2
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 71

Cys Ala Phe Gly Leu Lys Leu Asp Arg Ile Ser Cys
1               5                   10

<210> SEQ ID NO 72
<211> LENGTH: 12
<212> TYPE: PRT
<213> ORGANISM: Homo sapiens
<220> FEATURE:
<223> OTHER INFORMATION: N-term PhPrCO

```
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 72

Cys Ala Phe Gly Leu Lys Leu Asp Arg Ile Ser Cys
1               5                   10

<210> SEQ ID NO 73
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position

<400> SEQUENCE: 73

Cys Ala Phe Gly Leu Lys Leu Asp Arg Ile Ser Cys
1               5                   10

<210> SEQ ID NO 74
<211> LENGTH: 13
<212> TYPE: PRT
<213> ORGANISM: Homo sapiens
<220> FEATURE:
<223> OTHER INFORMATION: N-term H
<220> FEATURE:
<221> NAME/KEY: DISULFID
<222> LOCATION: (2)..(13)
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (R)-alpha-methyl-proline
<220> FEATURE:
<223> OTHER INFORMATION: C-term NH2

<400> SEQUENCE: 74

Met Cys Ala Phe Gly Leu Xaa Leu Asp Arg Ile Ser Cys
1               5                   10

<210> SEQ ID NO 75
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (S)-azetidine-2-carboxylic acid
<220> FEATURE:
<223> OTHER INFORMATION: C-term NH2
```

<400> SEQUENCE: 75

Cys Ala Phe Gly Leu Xaa Leu Asp Arg Ile Ser Cys
1               5                   10

<210> SEQ ID NO 76
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-ortho-chloro-phenylalanine
<220> FEATURE:
<223> OTHER INFORMATION: C-term NH2

<400> SEQUENCE: 76

Cys Ala Xaa Gly Leu Lys Leu Asp Arg Ile Ser Cys
1               5                   10

<210> SEQ ID NO 77
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-chloro-phenylalanine
<220> FEATURE:
<223> OTHER INFORMATION: C-term NH2

<400> SEQUENCE: 77

Cys Ala Xaa Gly Leu Lys Leu Asp Arg Ile Ser Cys
1               5                   10

<210> SEQ ID NO 78
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = Eau
<220> FEATURE:
<223> OTHER INFORMATION: C-term NH2

<400> SEQUENCE: 78

Cys Ala Xaa Gly Leu Lys Leu Asp Arg Ile Ser Cys
1               5                   10

<210> SEQ ID NO 79
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (2)..(2)
<223> OTHER INFORMATION: Xaa = (R)-azetidine-2-carboxylic acid
<220> FEATURE:
<223> OTHER INFORMATION: C-term NH2

<400> SEQUENCE: 79

Cys Xaa Phe Gly Leu Lys Leu Asp Arg Ile Ser Cys
1               5                   10

<210> SEQ ID NO 80
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (2)..(2)
<223> OTHER INFORMATION: Xaa = (R)-thiazolidine-4-carboxylic acid
<220> FEATURE:
<223> OTHER INFORMATION: C-term NH2

<400> SEQUENCE: 80

Cys Xaa Phe Gly Leu Lys Leu Asp Arg Ile Ser Cys
1               5                   10

<210> SEQ ID NO 81
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<223> OTHER INFORMATION: C-term NH2

<400> SEQUENCE: 81

```
Cys Xaa Phe Gly Leu Lys Leu Asp Arg Ile Ser Cys
1               5                   10
```

<210> SEQ ID NO 82
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-homo-arginine
<220> FEATURE:
<223> OTHER INFORMATION: C-term NH2

<400> SEQUENCE: 82

```
Cys Ala Phe Gly Leu Lys Leu Asp Xaa Ile Ser Cys
1               5                   10
```

<210> SEQ ID NO 83
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-norleucine
<220> FEATURE:
<223> OTHER INFORMATION: C-term NH2

<400> SEQUENCE: 83

```
Cys Ala Phe Gly Leu Lys Xaa Asp Arg Ile Ser Cys
1               5                   10
```

<210> SEQ ID NO 84
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-tert-butylglycine
<220> FEATURE:
<223> OTHER INFORMATION: C-term NH2

<400> SEQUENCE: 84

```
Cys Ala Phe Gly Leu Lys Xaa Asp Arg Ile Ser Cys
1               5                   10
```

<210> SEQ ID NO 85
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (S)-2-=amino-4-(N-piperidin-4-yl)-butyric
      acid
<220> FEATURE:
<223> OTHER INFORMATION: C-term NH2

<400> SEQUENCE: 85

```
Cys Ala Phe Gly Leu Xaa Leu Asp Arg Ile Ser Cys
1               5                   10
```

<210> SEQ ID NO 86
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,3S)-3-hydroxy-pyrrolidine-2-
      carboxylic acid
<220> FEATURE:
<223> OTHER INFORMATION: C-term NH2

<400> SEQUENCE: 86

```
Cys Ala Phe Gly Leu Xaa Leu Asp Arg Ile Ser Cys
1               5                   10
```

<210> SEQ ID NO 87
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 87

```
Cys Ala Phe Gly Leu Lys Ile Asp Arg Ile Ser Cys
1               5                   10
```

<210> SEQ ID NO 88
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 88

Cys Ala Phe Gly Leu Pro Ile Asp Arg Ile Ser Cys
1               5                   10

<210> SEQ ID NO 89
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 89

Cys Pro Phe Gly Leu Pro Ile Asp Arg Ile Ser Cys
1               5                   10

<210> SEQ ID NO 90
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 90

Cys Pro Phe Gly Leu Lys Leu Asp Arg Ile Ser Cys
1               5                   10

<210> SEQ ID NO 91
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)

<223> OTHER INFORMATION: D form of amino acid at this position
<220> FEATURE:
<223> OTHER INFORMATION: C-term NH2

<400> SEQUENCE: 91

Cys Pro Phe Gly Leu Pro Leu Asp Arg Ile Ser Cys
1               5                   10

<210> SEQ ID NO 92
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 92

Cys Pro Phe Gly Leu Lys Ile Asp Arg Ile Ser Cys
1               5                   10

<210> SEQ ID NO 93
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 93

Cys Ala Phe Gly Leu Pro Leu Asp Arg Ile Ser Cys
1               5                   10

<210> SEQ ID NO 94
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-cyclohexylglycine
<220> FEATURE:
<223> OTHER INFORMATION: C-term NH2

<400> SEQUENCE: 94

Cys Ala Phe Gly Leu Lys Xaa Asp Arg Ile Ser Cys
1               5                   10

<210> SEQ ID NO 95
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-2-amino-4,4-dimethyl-pentanoic acid
<220> FEATURE:
<223> OTHER INFORMATION: C-term NH2

<400> SEQUENCE: 95

Cys Ala Phe Gly Leu Lys Xaa Asp Arg Ile Ser Cys
1               5                   10

<210> SEQ ID NO 96
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-ornithine
<220> FEATURE:
<223> OTHER INFORMATION: C-term NH2

<400> SEQUENCE: 96

Cys Ala Phe Gly Leu Lys Leu Asp Xaa Ile Ser Cys
1               5                   10

<210> SEQ ID NO 97
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-5-(4,5-dihydro-1H-imidazol-2-
      ylamino)-pentanoic acid
<220> FEATURE:
<223> OTHER INFORMATION: C-term NH2

<400> SEQUENCE: 97

Cys Ala Phe Gly Leu Lys Leu Asp Xaa Ile Ser Cys
1               5                   10

```
<210> SEQ ID NO 98
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-5-(N'-methyl-guanidino)-
      pentanoic acid
<220> FEATURE:
<223> OTHER INFORMATION: C-term NH2

<400> SEQUENCE: 98

Cys Ala Phe Gly Leu Lys Leu Asp Xaa Ile Ser Cys
1               5                   10

<210> SEQ ID NO 99
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-5-(N',N'-dimethyl-guanidino)-
      pentanoic acid
<220> FEATURE:
<223> OTHER INFORMATION: C-term NH2

<400> SEQUENCE: 99

Cys Ala Phe Gly Leu Lys Leu Asp Xaa Ile Ser Cys
1               5                   10

<210> SEQ ID NO 100
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 100

Cys Ala Phe Gly Thr Leu Lys Asp Arg Ile Ser Cys
1               5                   10

<210> SEQ ID NO 101
<211> LENGTH: 12
```

```
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 101

Cys Ala Phe Gly Ala Lys Leu Asp Arg Ile Ser Cys
1               5                   10

<210> SEQ ID NO 102
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<223> OTHER INFORMATION: C-term NH2

<400> SEQUENCE: 102

Cys Ala Phe Gly Gly Lys Leu Asp Arg Ile Ser Cys
1               5                   10

<210> SEQ ID NO 103
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-fluoro-phenylalanine
<220> FEATURE:
<223> OTHER INFORMATION: C-term NH2

<400> SEQUENCE: 103

Cys Ala Xaa Gly Leu Lys Leu Asp Arg Ile Ser Cys
1               5                   10

<210> SEQ ID NO 104
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
```

<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-methyl-phenylalanine
<220> FEATURE:
<223> OTHER INFORMATION: C-term NH2

<400> SEQUENCE: 104

Cys Ala Xaa Gly Leu Lys Leu Asp Arg Ile Ser Cys
1               5                   10

<210> SEQ ID NO 105
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-trifluoromethyl-phenylalanine

<400> SEQUENCE: 105

Cys Ala Xaa Gly Leu Lys Leu Asp Arg Ile Ser Cys
1               5                   10

<210> SEQ ID NO 106
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-cyano-phenylalanine
<220> FEATURE:
<223> OTHER INFORMATION: C-term NH2

<400> SEQUENCE: 106

Cys Ala Xaa Gly Leu Lys Leu Asp Arg Ile Ser Cys
1               5                   10

<210> SEQ ID NO 107
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)

```
<223> OTHER INFORMATION: Xaa = (S)-meta-nitro-phenylalanine
<220> FEATURE:
<223> OTHER INFORMATION: C-term NH2

<400> SEQUENCE: 107

Cys Ala Xaa Gly Leu Lys Leu Asp Arg Ile Ser Cys
1               5                   10

<210> SEQ ID NO 108
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-methoxy-phenylalanine
<220> FEATURE:
<223> OTHER INFORMATION: C-term NH2

<400> SEQUENCE: 108

Cys Ala Xaa Gly Leu Lys Leu Asp Arg Ile Ser Cys
1               5                   10

<210> SEQ ID NO 109
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-5-(N'-dimethyl-guanidino)-
      pentanoic acid

<400> SEQUENCE: 109

Cys Ala Phe Gly Leu Lys Leu Asp Xaa Ile Ser Cys
1               5                   10

<210> SEQ ID NO 110
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 1-amino-cyclopentane carboxylic acid
<220> FEATURE:
<223> OTHER INFORMATION: C-term NH2
```

```
<400> SEQUENCE: 110

Cys Ala Phe Gly Leu Lys Leu Asp Arg Xaa Ser Cys
1               5                   10

<210> SEQ ID NO 111
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-5-(pyridin-2-ylamino)-
      pentanoic acid
<220> FEATURE:
<223> OTHER INFORMATION: C-term NH2

<400> SEQUENCE: 111

Cys Ala Phe Gly Leu Lys Leu Asp Xaa Ile Ser Cys
1               5                   10

<210> SEQ ID NO 112
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-3-(4-carbamimidoyl-phenyl)-
      propionic acid

<400> SEQUENCE: 112

Cys Ala Phe Gly Leu Lys Leu Asp Xaa Ile Ser Cys
1               5                   10

<210> SEQ ID NO 113
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-4-N-piperidinyl)-acetic acid
<220> FEATURE:
<223> OTHER INFORMATION: C-term NH2

<400> SEQUENCE: 113

Cys Ala Phe Gly Leu Pro Leu Asp Xaa Ile Ser Cys
```

<210> SEQ ID NO 114
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-4-guanidino-butyric acid

<400> SEQUENCE: 114

Cys Ala Phe Gly Leu Lys Leu Asp Xaa Ile Ser Cys
1               5                   10

<210> SEQ ID NO 115
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 1-amino-cyclohexane carboxylic acid
<220> FEATURE:
<223> OTHER INFORMATION: C-term NH2

<400> SEQUENCE: 115

Cys Ala Phe Gly Leu Lys Leu Asp Arg Xaa Ser Cys
1               5                   10

<210> SEQ ID NO 116
<211> LENGTH: 12
<212> TYPE: PRT
<213> ORGANISM: Homo sapiens
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 4-amino-tetrahydro-pyran-4-carboxylic
      acid

<400> SEQUENCE: 116

Cys Ala Phe Gly Leu Lys Leu Asp Arg Xaa Ser Cys
1               5                   10

<210> SEQ ID NO 117
<211> LENGTH: 12
<212> TYPE: PRT
<213> ORGANISM: Homo sapiens
<220> FEATURE:

```
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 4-amino-tetrahydro-thiopyran-4-carboxylic
      acid

<400> SEQUENCE: 117

Cys Ala Phe Gly Leu Lys Leu Asp Arg Xaa Ser Cys
1               5                   10

<210> SEQ ID NO 118
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 1-amino-cyclohexane acetic acid
<220> FEATURE:
<223> OTHER INFORMATION: C-term NH2

<400> SEQUENCE: 118

Cys Ala Phe Gly Leu Lys Leu Asp Arg Xaa Ser Cys
1               5                   10

<210> SEQ ID NO 119
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = (S)-cyclohexylglycine
<220> FEATURE:
<223> OTHER INFORMATION: C-term NH2

<400> SEQUENCE: 119

Cys Ala Phe Gly Leu Lys Leu Asp Arg Xaa Ser Cys
1               5                   10

<210> SEQ ID NO 120
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
```

```
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (12)..(12)
<223> OTHER INFORMATION: Xaa = 2-aminoethanethiol

<400> SEQUENCE: 120

Cys Ala Phe Gly Leu Lys Leu Asp Arg Ile Ser Xaa
1               5                   10

<210> SEQ ID NO 121
<211> LENGTH: 12
<212> TYPE: PRT
<213> ORGANISM: Homo sapiens
<220> FEATURE:
<223> OTHER INFORMATION: N-term Hex
<220> FEATURE:
<221> NAME/KEY: DISULFID
<222> LOCATION: (1)..(12)
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-2-amino-4-(2-amino-pyrimidin-4-yl)-
      butyric acid
<220> FEATURE:
<223> OTHER INFORMATION: C-term NH2

<400> SEQUENCE: 121

Cys Ala Phe Gly Leu Lys Leu Asp Xaa Ile Ser Cys
1               5                   10
```